(12) United States Patent
Tapper et al.

(10) Patent No.: US 8,063,227 B2
(45) Date of Patent: Nov. 22, 2011

(54) SALTS AND POLYMORPHS OF DESAZADESFERRITHIOCIN POLYETHER ANALOGUES AS METAL CHELATION AGENTS

(75) Inventors: Amy E. Tapper, Boston, MA (US); Hugh Y. Rienhoff, Jr., San Carlos, CA (US); Stephan D. Parent, West Lafayette, IN (US); Patricia Andres, West Lafayette, IN (US); Jason A. Hanko, West Lafayette, IN (US); Huamin Zhang, West Lafayette, IN (US)

(73) Assignee: Ferrokin Biosciences, Inc., San Carlos, CA (US)

( * ) Notice: Subject to any disclaimer, the term of this patent is extended or adjusted under 35 U.S.C. 154(b) by 0 days.

(21) Appl. No.: 12/502,559

(22) Filed: Jul. 14, 2009

(65) Prior Publication Data

US 2010/0137383 A1    Jun. 3, 2010

Related U.S. Application Data

(60) Provisional application No. 61/080,572, filed on Jul. 14, 2008, provisional application No. 61/152,572, filed on Feb. 13, 2009.

(51) Int. Cl.
    *C07D 277/10* (2006.01)
(52) U.S. Cl. ........................................ 548/201
(58) Field of Classification Search .................. 548/201
    See application file for complete search history.

(56) References Cited

U.S. PATENT DOCUMENTS

| 2005/0101782 A1 | 5/2005 | Krich |
| 2006/0069134 A1 | 3/2006 | Maruoka |
| 2008/0138440 A1 | 6/2008 | Swaminathan et al. |

FOREIGN PATENT DOCUMENTS

| WO | 2005023310 | 3/2005 |
| WO | 2005023310 A2 | 3/2005 |
| WO | 2006107626 | 10/2006 |
| WO | 2008115433 | 9/2008 |
| WO | 2008130395 | 10/2008 |
| WO | 2008130395 A2 | 10/2008 |

OTHER PUBLICATIONS

Byrn, et al. ed. "Comparing X-ray Powder Data". Solid State Chemistry of Drugs, 2$^{nd}$ edition, p. 63.*
Bergeron, RJ, Iron chelation promoted by desazadesferrithiocin analogs: An enantioselective barrier, Chirality; vol. 15, Issue 7, pp. 593-599, 2003.
Bergeron, RJ, et al, Design, Synthesis, and Testing of Non-Nephrotoxic Desazadesferrithiocin Polyether Analogues, J. Med. Chem. 2008, 51, 3913-3923.
Bergeron, RJ, et al, Polyamine-Vectored Iron Chelators: The Role of Charge, J. Med. Chem. 2005, 48, 4120-4137.
Bergeron, RJ, et al, (S)-4,5-Dihydro-2-(2-hydroxy-4-hydroxyphenyl)-4-methyl-4-thiazolecarboxylic Acid Polyethers: A Solution to Nephrotoxicity, J. Med. Chem. 2006, 49, 2772-2783.
Bergeron, RJ, et al, Impact of the 3,6,9-Trioxadecyloxy Group on Desazadesferrithiocin Analogue Iron Clearance and Organ Distribution, J. Med. Chem. 2007, 50, 3302-3313.
"EP08742093 EP Search Report and Opinion",University of Florida, USA, Dec. 27, 2010.
Bergeron, RJ; Biometals, Nov. 2010; (e-publication only) http://www.springerlink.com/content/p5254pq117818112/, Nov. 20, 2010.
WO 2008115433; ISR and WO, University of Florida, USA, Jun. 19, 2008.
WO2010009120 IPRP, FerroKin (FKB0001-401), Jan. 27, 2011.

* cited by examiner

*Primary Examiner* — Shawquia Young
(74) *Attorney, Agent, or Firm* — Dennis A. Bennett; Cynthia Hathaway

(57) ABSTRACT

Disclosed herein are new salts and polymorphs of desazadesferrithiocin polyether (DADFT-PE) analogues, as well as pharmaceutical compositions comprising them and their application as metal chelation agents for the treatment of disease. Methods of chelation of iron and other metals in a human or animal subject are also provided for the treatment of metal overload and toxicity.

1 Claim, 20 Drawing Sheets

SALTS AND POLYMORPHS OF DESAZADESFERRITHIOCIN POLYETHER ANALOGUES AS METAL CHELATION AGENTS

This application claims the benefit of priority of U.S. provisional applications No. 61/080,572, filed Jul. 14, 2008, and No. 61/152,572, filed Feb. 13, 2009, the disclosures of which are hereby incorporated by reference as if written herein in their entirety.

Disclosed herein are new salts and polymorphs of desazadesferrithiocin polyether (DADFT-PE) analogues, as well as pharmaceutical compositions comprising them and their application as metal chelation agents for the treatment of disease. Methods of chelation of iron and other metals in a human or animal subject are also provided for the treatment of metal overload and toxicity.

Metal ions are critical to the proper functioning of living systems. Ions such as $Fe^{3+}$, $Zn^{2+}$, $Cu^{2+}$, $Ca^{2+}$, and $Co^{3+}$, to name but a few, can be found in the active sites of over a third of known enzymes and other functional proteins such as RNA polymerase, DNA transcription factors, cytochromes P450s, hemoglobin, myoglobin, and coenzymes such as vitamin $B_{12}$. There, these metals serve to facilitate oxidation and reduction reactions, stabilize or shield charge distributions, and orient substrates for reactions.

However, the body has a limited ability to absorb and excrete metals, and an excess can lead to toxicity. As one example, an excess of iron, whether derived from red blood cells chronically transfused, necessary in such conditions such as beta thalassemia major, or from increased absorption of dietary iron such as hereditary hemochromatosis can be toxic through the generation by iron of reactive oxygen species such as $H_2O_2$. In the presence of $Fe^{2+}$, $H_2O_2$ is reduced to the hydroxyl radical (HO), a very reactive species, a process known as the Fenton reaction. The hydroxyl radical reacts very quickly with a variety of cellular constituents and can initiate free radicals and radical-mediated chain processes that damage DNA and membranes, as well as produce carcinogens. The clinical result is that without effective treatment, body iron progressively increases with deposition in the liver, heart, pancreas, and elsewhere. Iron accumulation may also produce (i) liver disease that may progress to cirrhosis, (ii) diabetes related both to iron-induced decreases in pancreatic β-cell secretion and increases in hepatic insulin resistance and (iii) heart disease, still the leading cause of death in beta thalassemia major and other anemias associated with transfusional iron overload.

As another example, ions with little or no endogenous function may find their way into the body and effect damage. Heavy metal ions such as $Hg^{2+}$ can replace ions such as $Zn^{2+}$ in metalloproteins and render them inactive, resulting in serious acute or chronic toxicity that can end in a patient's death or in birth defects in that patient's children. Even more significantly, radioactive isotopes of the lanthanide and actinide series can visit grave illness on an individual exposed to them by mouth, air, or skin contact. Such exposure could result not only from the detonation of a nuclear bomb or a "dirty bomb" composed of nuclear waste, but also from the destruction of a nuclear power facility.

Agents for the chelation and decorporation of metal ions in living organisms have been previously disclosed and are in clinical use. A variety of ligands have been shown to bind $Fe^{3+}$, $Pu^{4+}$, $Th^{4+}$, $Am^{4+}$, $E^{3+}$ and $U^{4+}$, for example. Traditional standard therapies include the use of agents such as deferoxamine (DFO, N'-[5-(acetyl-hydroxy-amino)pentyl]-N-[5-[3-(5-aminopentyl-hydroxy-carbamoyl)propanoylamino]pentyl]-N-hydroxy-butane diamide), a very effective metal chelator. DFO is, unfortunately, not orally bioavailable and must therefore be parenterally dosed IV, IP, or SC, and once in the bloodstream has a very short half life. Diethylene triamine pentaacetic acid (DTPA) is approved for use in the treatment of lanthanide and actinide poisoning, but also cannot be dosed orally, ideally should be given very quickly following contamination, and presents with a number of side effects. For these reasons, continuous infusion of these agents is often required, and particularly in the case of chronic disorders, patient compliance can be a problem. A thorough review of publicly available art will show that although effective chelation agents have been available for decades, oral bioavailability has historically been a desirable trait in successive next-generation agents.

More recently, orally active agents have become available for use in the treatment of metal overload. Deferiprone (3-hydroxy-1,2-dimethylpyridin-4(1H)-one) has been used in Europe and some other countries as an oral agent for the treatment of transfusional iron overload in the setting of beta thalassemia and other disorders, but the drug is not approved for use in the United States and Canada, and reported side effects including agranulocytosis have in many cases relegated it to second-line therapy. Deferasirox (Exjade, [4-[(3Z,5E)-3,5-bis(6-oxo-1-cyclohexa-2,4-dienylidene)-1,2,4-triazolidin-1-yl]benzoic acid, Novartis) is currently the only oral agent approved in the United States for chelation therapy. Even still, nephrotoxicity leading to renal failure and cytopenia have been reported by the Food and Drug Administration as side effects to Deferasirox oral suspension tablets. Moreover, neither of these agents is as efficacious a chelator as DFO. Clearly, a need still exists in the art for long-lasting, orally active metal chelators with reduced toxicity for the treatment of iron overload secondary to transfusion or excessive intestinal absorption and other metal overload disorders.

Analogues of desferrithiocin, or [(S)-4,5-dihydro-2-(3-hydroxy-2-pyridinyl)4-methyl-4-thiazo]carboxylic acid (DFT) have been shown to form 2:1 hexacoordinate complexes with $Fe^{3+}$ and $Th^{4+}$. These ligands, when administered either subcutaneously (SC) or orally (PO) to rodents, dogs, and primates, have been shown to clear iron very efficiently, and to decorporate uranium from rodents when given SC, PO, or intraperitoneally, with particularly profound effects in the kidney. Although development of DFT itself had been discontinued due to nephrotoxicity, one of these ligands (S)-2-(2,4-dihydroxyphenyl)-4,5-dihydro-4-methyl-4-thiazolecarboxylic acid, or (S)-4'-(HO)-DADFT, has proven to be an effective chelation agent with the additional benefit of being orally available, and as of the present is believed to be in clinical trials. A very recent paper discloses the design and testing of DADFT analogues substituted by a polyether group at the 3', 4', and 5' positions (Bergeron R J et al., *J Med. Chem.* 2007 Jul. 12; 50(14):3302-13). Polyether analogues had uniformly higher iron-clearing efficiencies (ICEs) than their corresponding parent ligands in rodents and in serum albumin binding studies, with the 3'-DADFT-PE analogue (S)-4,5-dihydro-2-[2-hydroxy-3-(3,6,9-trioxadecyloxy)phenyl]-4-methyl-4-thiazolecarboxylic acid showing the most promising ICE in rodents and non-human primates.

Though DADFT polyethers as a class of compounds appear promising in the search for improved metal chelation agents, much work remains to be done in the characterization, development, and selection of a compound suitable for use in humans. Room for improvement is still apparent in the design of analogues and salt forms thereof which have the optimal balance of ICE, bioavailability, favorable toxicology, and other attributes for the purpose of providing safe and effective compounds which will be easy to use by patients and clinicians alike. Additionally, many factors still influence the suitability of a compound as a pharmaceutical agent in general. To be suitable for manufacture and distribution, a compound should be capable of being produced in yield and purity, or should be capable of being purified from co-products. Such a compound should also be stable, i.e., should not degrade over time into potentially inactive or toxic compounds, or even transform into alternate crystalline forms having different and potentially quite relevant dissolution, absorption, and other properties.

Disclosed herein are novel salts and polymorphs of these polyether analogues and derivatives thereof. Pharmaceutical formulations comprising the salts and polymorphs are also disclosed, as well as methods for the treatment of diseases and conditions related to toxicity which is a result of an acute or chronic excess of metal in a human or animal body. Certain salts disclosed herein are stable, pure, and soluble, indicating likely bioavailability.

In certain embodiments are provided salts having structural Formula I:

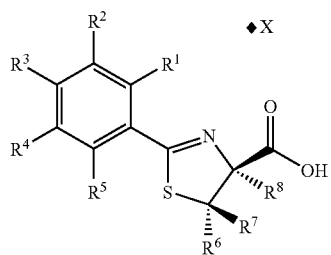

wherein:

$R^1$, $R^2$, $R^3$, $R^4$, and $R^5$ are independently chosen from hydrogen, hydroxy, alkyl, arylalkyl, alkoxy, and $CH_3O$ $((CH_2)_n-O)_m-$, any of which may be optionally substituted;

$R^6$, $R^7$, and $R^8$ are independently chosen from hydrogen, halogen, hydroxy, lower alkyl, and lower alkoxy;

m is an integer from 0 to 8;

n is an integer from 0 to 8; and

X is a counterion;

or a polymorph thereof.

Certain compounds, salts, and polymorphs disclosed herein may possess useful metal chelating activity, and may be used in the treatment or prophylaxis of a disease or condition in which metal overload or toxicity plays an active role. Thus, in broad aspect, certain embodiments also provide pharmaceutical compositions comprising one or more compounds, salts, or polymorphs disclosed herein together with a pharmaceutically acceptable carrier, as well as methods of making and using the compounds, salts, and polymorphs and their compositions. Certain embodiments provide methods for chelating metals in living systems. Other embodiments provide methods for treating disorders and symptoms relating to metal toxicity in a patient in need of such treatment, comprising administering to said patient a therapeutically effective amount of a compound or composition as disclosed herein, or a salt or polymorph thereof. Also provided is the use of certain compounds, salts, and polymorphs disclosed herein for use in the manufacture of a medicament for the treatment of a disease or condition ameliorated by the chelation or decorporation of metals.

In certain embodiments, salts of Formula I are solid.

In further embodiments, salts of Formula I are crystalline.

In certain embodiments, X is chosen from betaine, choline hydroxide, diethanolamine, diethylamine, ethanolamine, hydroxyethyl morpholine, hydroxyethyl pyrrolidine, imidazole, N-methyl-d-glucamine (NMG), N,N'-dibenzyl-ethylenediamine, N,N'-diethyl-ethanolamine, piperazine, triethanolamine, tromethamine, $Ca(OH)_2$, L-lysine, L-arginine, $Mg(OH)_2$, magnesium acetate, KOH, NaOH, $Zn(OH)_2$, zinc acetate, $Zn(OH)_2/Mg(OH)_2$, EDA, L-histidine, 4-(2-hydroxyethyl morpholine), 1-(2hydroxyethyl pyrrolidine), 1-(2-hydroxyethyl)-piperidine, potassium 2-ethylhexanoate, NaOAc, sodium 2-ethylhexanoate, 1,2-EDSA, HCl, H$_2$SO$_4$, MSA, and p-TSA monohydrate.

In certain embodiments, salts have structural Formula Ia:

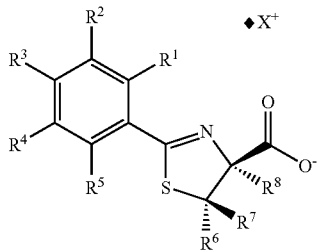

wherein:

R$^1$, R$^2$, R$^3$, R$^4$, and R$^5$ are independently chosen from hydrogen, hydroxy, alkyl, arylalkyl, alkoxy, and CH$_3$O ((CH$_2$)$_n$—O)$_m$—, any of which may be optionally substituted;

R$^6$, R$^7$, and R$^8$ are independently chosen from hydrogen, halogen, hydroxy, lower alkyl, and lower alkoxy;

m is an integer from 0 to 8;

n is an integer from 0 to 8; and

X is a counterion;

or a polymorph thereof.

In certain embodiments, salts are of Formula I wherein the counterion X is chosen from lysine, N-methyl-D-glucamine (NMG), tromethamine, calcium, magnesium, potassium, sodium, zinc, and piperazine.

In certain embodiments, R$^8$ is chosen from hydrogen and methyl.

In further embodiments, R$^6$ and R$^7$ are independently chosen from hydrogen and methoxy.

In further embodiments, R$^1$ is hydroxy.

In further embodiments, R$^2$, R$^3$, R$^4$, and R$^5$ are independently chosen from hydrogen and CH$_3$O((CH$_2$)$_n$—O)$_m$—.

In further embodiments, salts and polymorphs thereof have structural formula II:

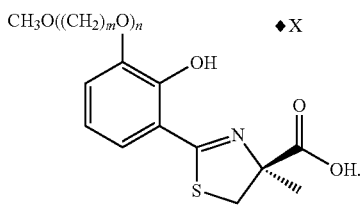

In further embodiments, salts and polymorphs thereof have structural formula IIa:

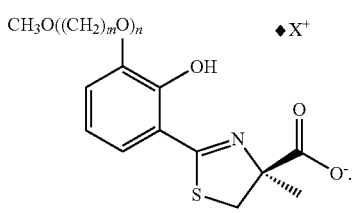

In further embodiments, the counterion X is chosen from calcium, magnesium, potassium, sodium, zinc, and piperazine.

In further embodiments, m is 2 and n is 3.

In further embodiments, the salt is the magnesium salt, or a polymorph thereof.

In further embodiments, the salt is magnesium 3'-desazadesferrithiocin polyether hydroxide or a polymorph thereof.

In further embodiments, said polymorph of magnesium 3'-desazadesferrithiocin polyether hydroxide is Form A.

Figure 7:
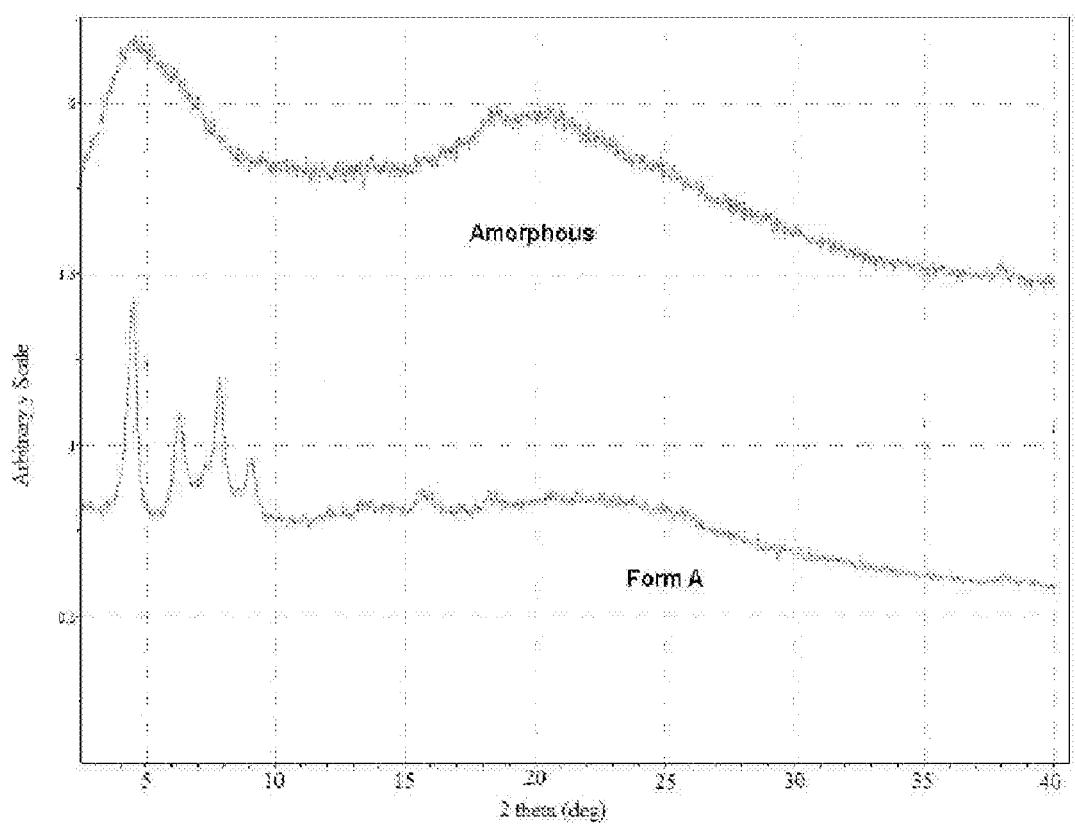
FIG. 7. XRPD Patterns of (S)-3'-(OH)-DADFT-PE magnesium salt: the amorphous form and form A (from top to bottom). Degrees θ-2θ on the abscissa are plotted against an arbitrary Y value on the ordinate.

In further embodiments, said Form A has an X-ray powder diffraction pattern which is at least 70%, at least 80%, at least 90%, or at least 95% identical to that shown in FIG. 7.

In other embodiments, said polymorph of magnesium 3'-desazadesferrithiocin polyether hydroxide is Form B.

Figure 8:
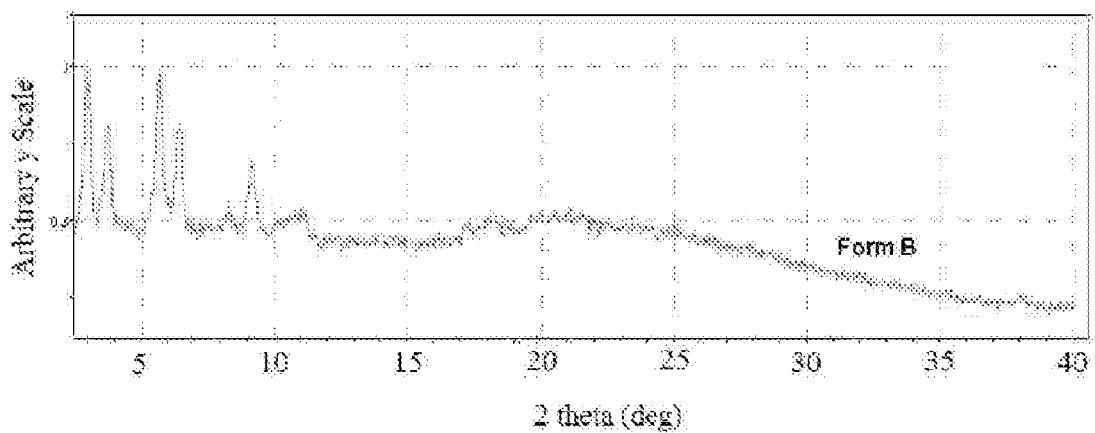
FIG. 8. XRPD Pattern of (S)-3'-(OH)-DADFT-PE magnesium salt form B. Degrees θ-2θ on the abscissa are plotted against an arbitrary Y value on the ordinate.

In further embodiments, said Form B has an X-ray powder diffraction pattern which is at least 70%, at least 80%, at least 90%, or at least 95% identical to that shown in FIG. 8.

Figure 10:
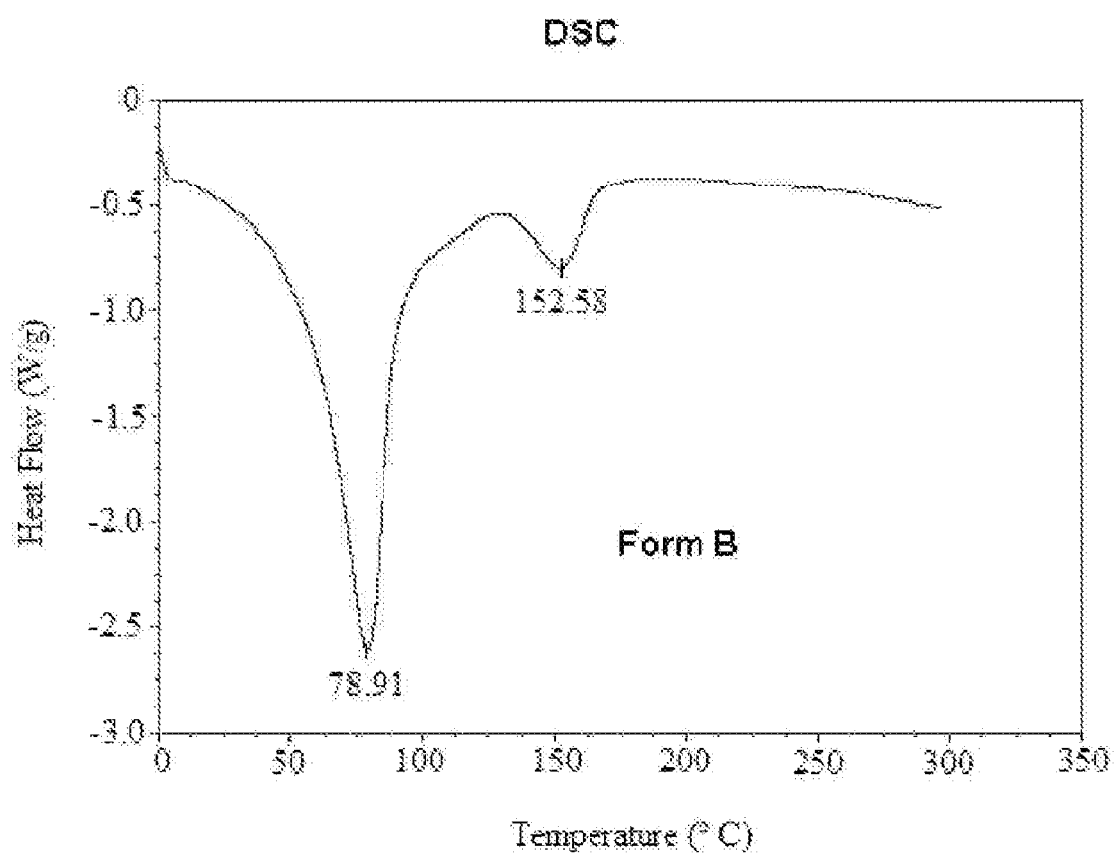

In further embodiments, said Form B has a differential scanning calorimetry (DSC) thermogram which is at least 70%, at least 80%, at least 90%, or at least 95% identical to that shown in FIG. 10.

Figure 11:
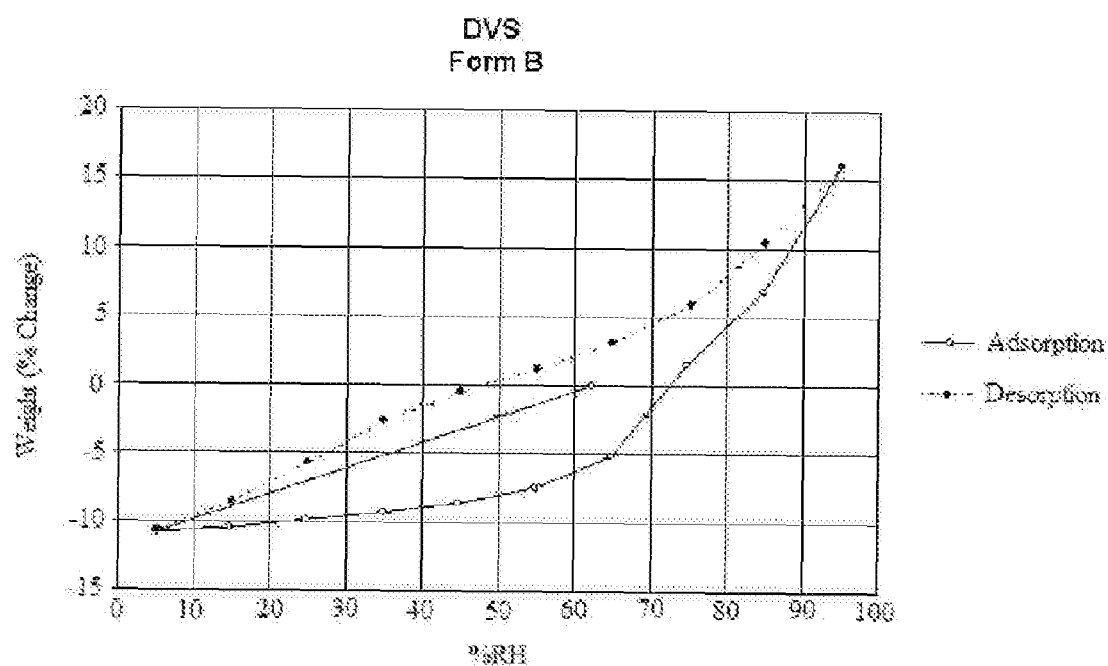
FIG. 11. Dynamic vapor sorption/desorption isotherm of (S)-3'-(OH)-DADFT-PE magnesium salt Form B.
Figure 12:
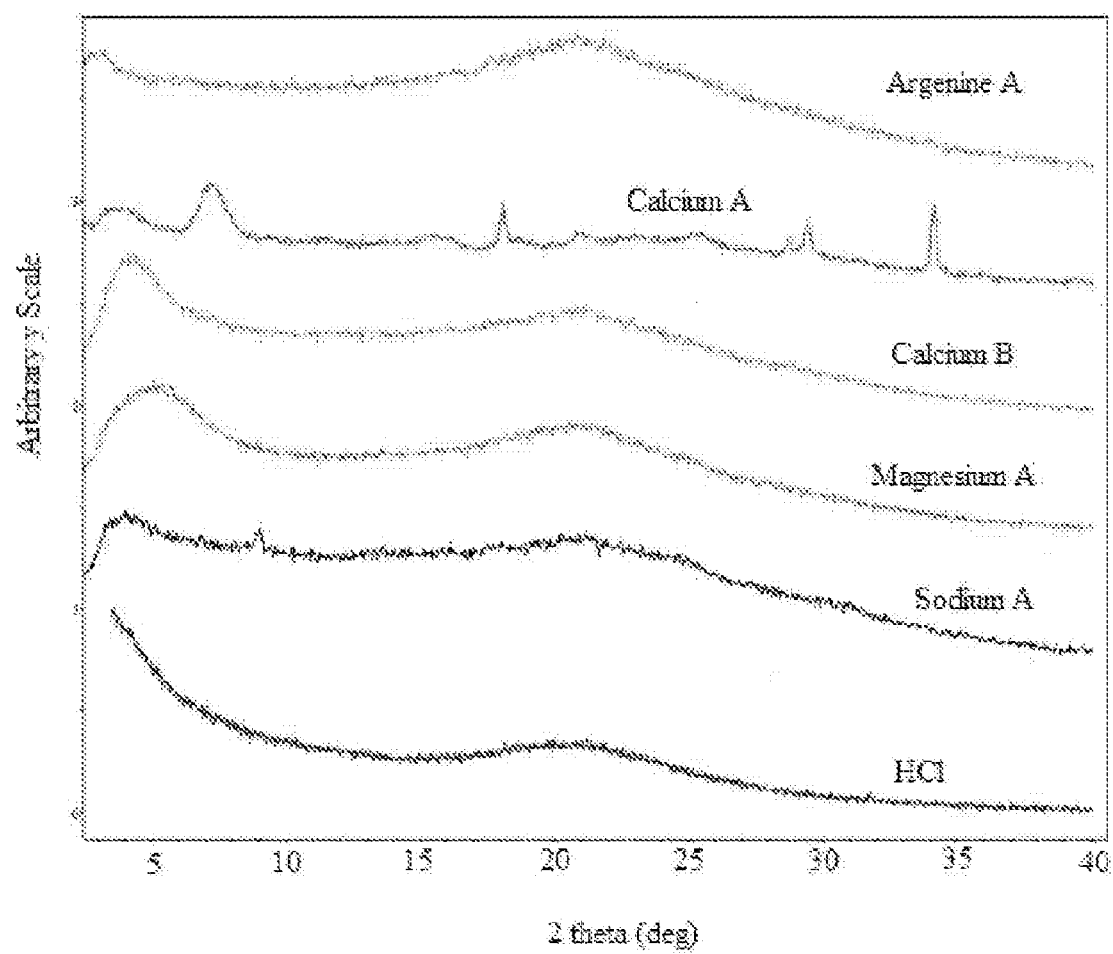
FIG. 12. XRPD Patterns of Salts of (S)-4'-(OH)-DADFT-PE: the arginine A, calcium A, calcium B, magnesium A, sodium A, and HCl salts (from top to bottom). Degrees θ-2θ on the abscissa are plotted against an arbitrary Y value on the ordinate.

In further embodiments, said Form B has a dynamic vapor sorption/desorption (DVS) spectrum which is at least 70%, at least 80%, at least 90%, or at least 95% identical to that shown in FIG. 11.

In other embodiments, said polymorph of magnesium 3'-desazadesferrithiocin polyether hydroxide is Form C.

Figure 9:
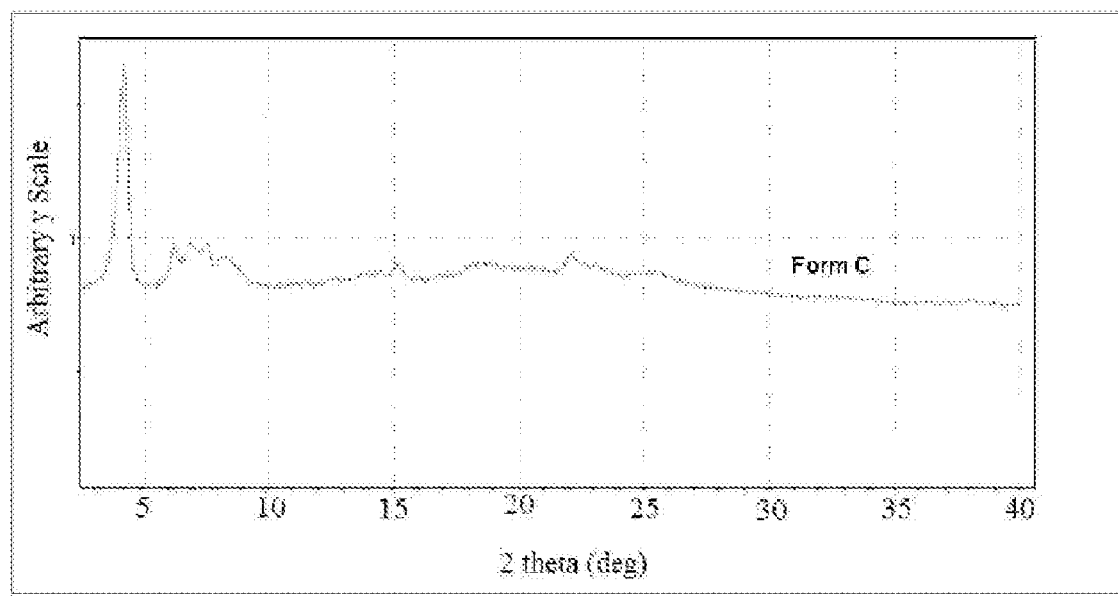
FIG. 9. XRPD Pattern of (S)-3'-(OH)-DADFT-PE magnesium salt form C. Degrees θ-2θ on the abscissa are plotted against an arbitrary Y value on the ordinate FIG. 10. DSC thermogram of (S)-3'-(OH)-DADFT-PE magnesium salt form B.

In further embodiments, said Form C has an X-ray powder diffraction pattern which is at least 70%, at least 80%, at least 90%, or at least 95% identical to that shown in FIG. 9.

In other embodiments is provided an amorphous form of magnesium 3'-desazadesferrithiocin polyether hydroxide.

In further embodiments, said amorphous form has an X-ray powder diffraction pattern which is at least 70%, at least 80%, at least 90%, or at least 95% identical to that shown in FIG. 7.

In further embodiments, the salt or polymorph thereof has an aqueous solubility at near-physiologic pH of between 0.3 mg/ml and 70 mg/ml.

In further embodiments, the salt or polymorph thereof has an aqueous solubility at near-physiologic pH of ≧40 mg/ml.

In further embodiments, the salt or polymorph thereof has an aqueous solubility at near-physiologic pH of ≧50 mg/ml.

In further embodiments, the salt or polymorph thereof has an aqueous solubility at simulated gastric pH of 0.05 mg/ml-250 mg/ml.

In further embodiments, the salt or polymorph thereof has an aqueous solubility at near-physiologic pH of between 0.3 mg/ml and 70 mg/ml and having an aqueous solubility at simulated gastric pH of 0.05 mg/ml-250 mg/ml.

In further embodiments, the salt is the potassium salt or a polymorph thereof.

Figure 1:
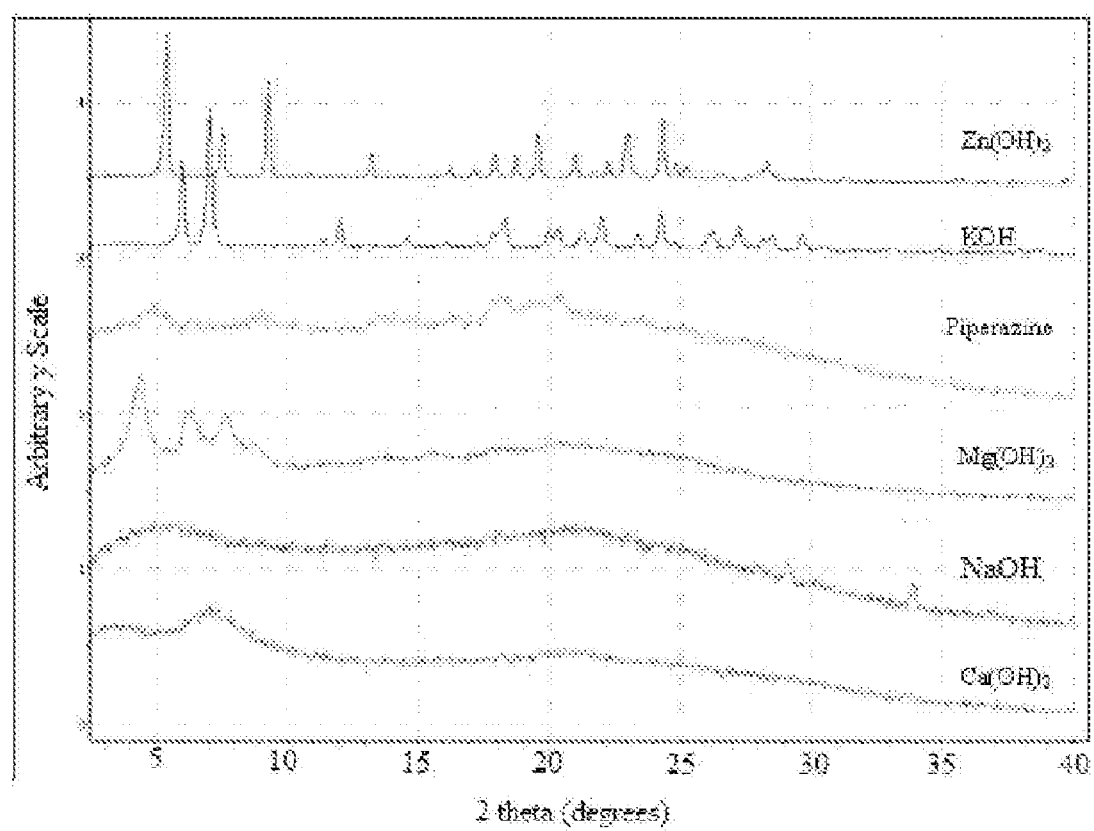
FIG. 1. XRPD Patterns of Salts of (S)-3'-(OH)-DADFT-PE: the zinc, potassium, piperazine, magnesium, sodium, and calcium salts (from top to bottom). Degrees θ-2θ on the abscissa are plotted against an arbitrary Y value on the ordinate.
Figure 2:
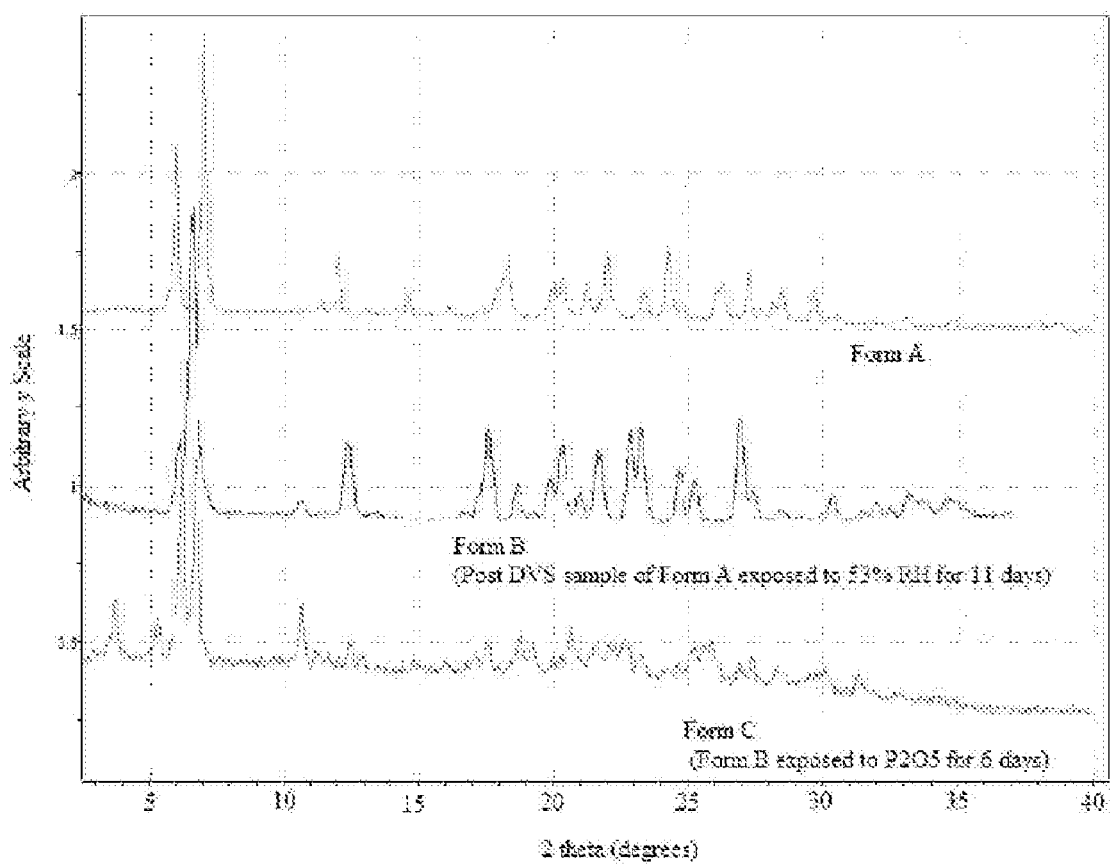
FIG. 2. Physical stability study of (S)-3'-(OH)-DADFT-PE potassium salt, isolated as the Form A polymorph (top spectrum), the Form B (middle spectrum) and the Form C (bottom spectra) salts. Degrees θ-2θ on the abscissa are plotted against an arbitrary Y value on the ordinate.

In further embodiments are provided the Form A polymorph of the potassium (S)-3'-DADFT-PE salt, having an XRPD pattern substantially similar to that shown in the upper curve of FIG. 2.

In further embodiments, the salt is the potassium salt, or a polymorph thereof.

In further embodiments, the potassium salt is characterized by an x-ray powder diffraction pattern comprising peaks at about:

6.0, 7.1, 12.0, 14.6, 20.0, 20.3, 21.3, 22.0, 23.3, 24.4, 26.3, 27.3, 28.5, and 29.6 degrees 2θ, plus or minus 0.2 degrees 2θ.

In further embodiments, the salt is potassium (S)-3'-desazadesferrithiocin polyether (KOH.(S)-3'-DADFT-PE).

In other embodiments, the salt is the zinc salt or a polymorph thereof.

In further embodiments, the salt is zinc (S)-3'-desazadesferrithiocin polyether (ZnOH.(S)-3'-DADFT-PE), or a polymorph thereof.

Figure 3:
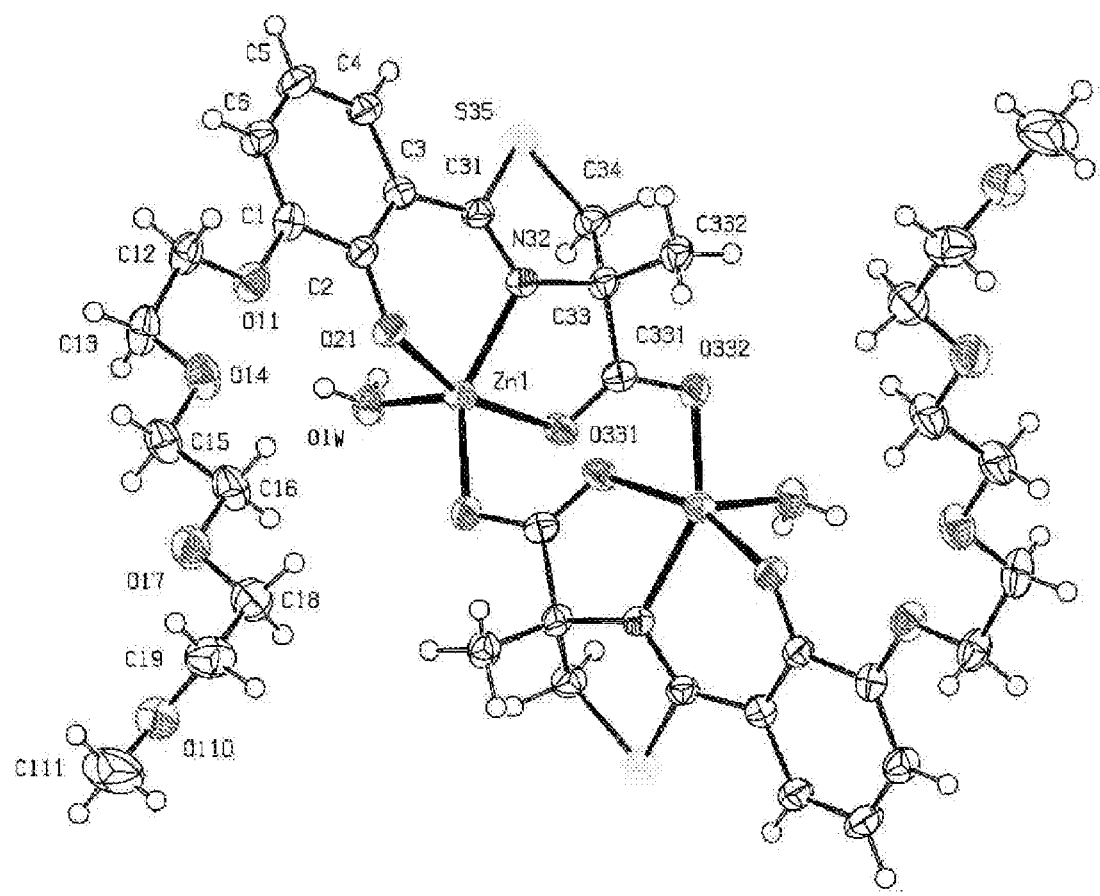
FIG. 3. ORTEP drawing of (S)-3'-(OH)-DADFT-PE Zinc salt. Atoms are represented by 50% probability anisotropic thermal ellipsoids.

In further embodiments, the salt has an SC-XRD structure characterized as in FIG. 3.

In certain embodiments, salts and polymorphs thereof have structural formula III:

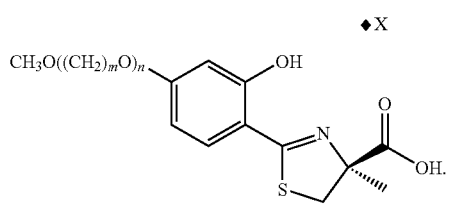

III

In further embodiments, salts and polymorphs thereof have structural formula IIIa:

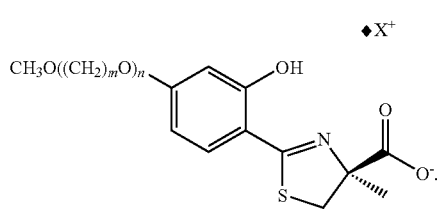

IIIa

In further embodiments, X is chosen from lysine, NMG, tromethamine, calcium, and magnesium.

In further embodiments is provided a polymorph of a salt of Formula III, wherein the polymorph is a stoichiometric hydrate of the sodium salt.

In further embodiments, said polymorph is the monohydrate.

In further embodiments, said polymorph is the dihydrate.

In further embodiments is provided tromethamine 4'-desazadesferrithiocin polyether hydroxide, or a polymorph thereof.

Figure 13:
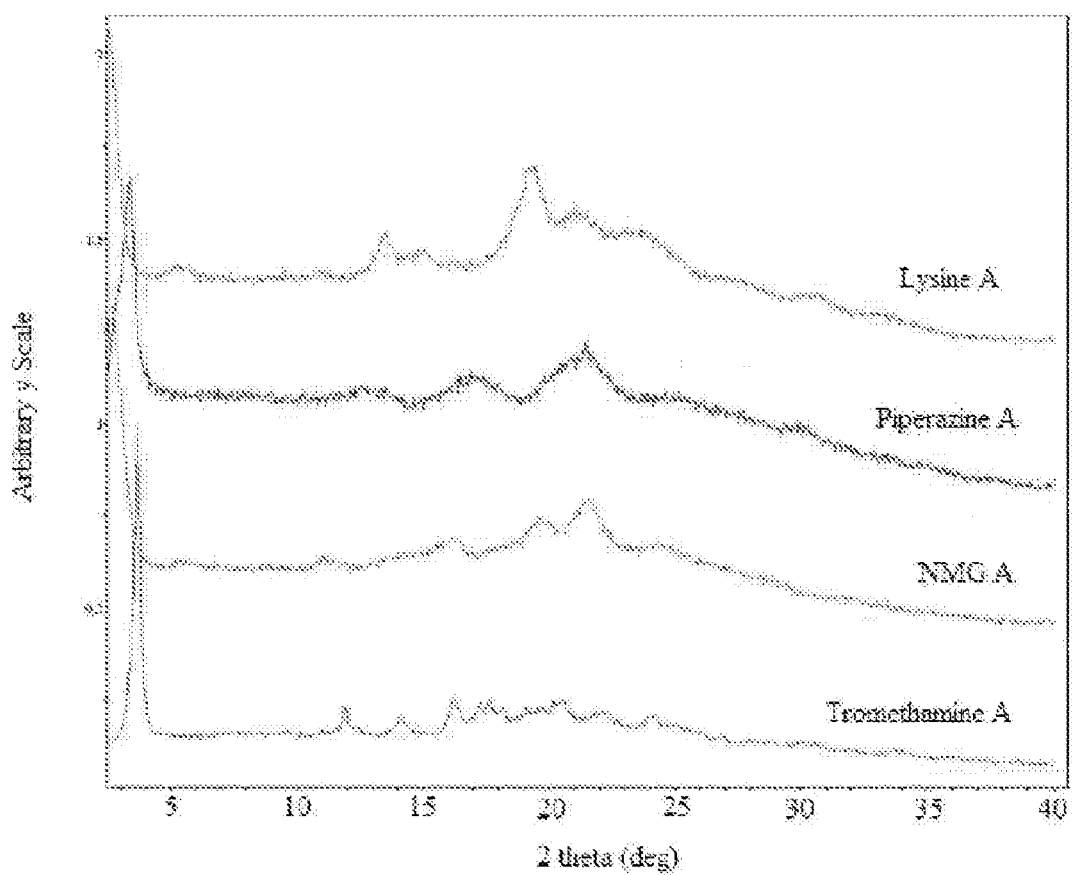
FIG. 13. XRPD Patterns of Salts of (S)-4'-(OH)-DADFT-PE: the lysine A, piperazine A, NMG A, and tromethamine A salts (from top to bottom). Degrees θ-2θ on the abscissa are plotted against an arbitrary Y value on the ordinate.
Figure 14:
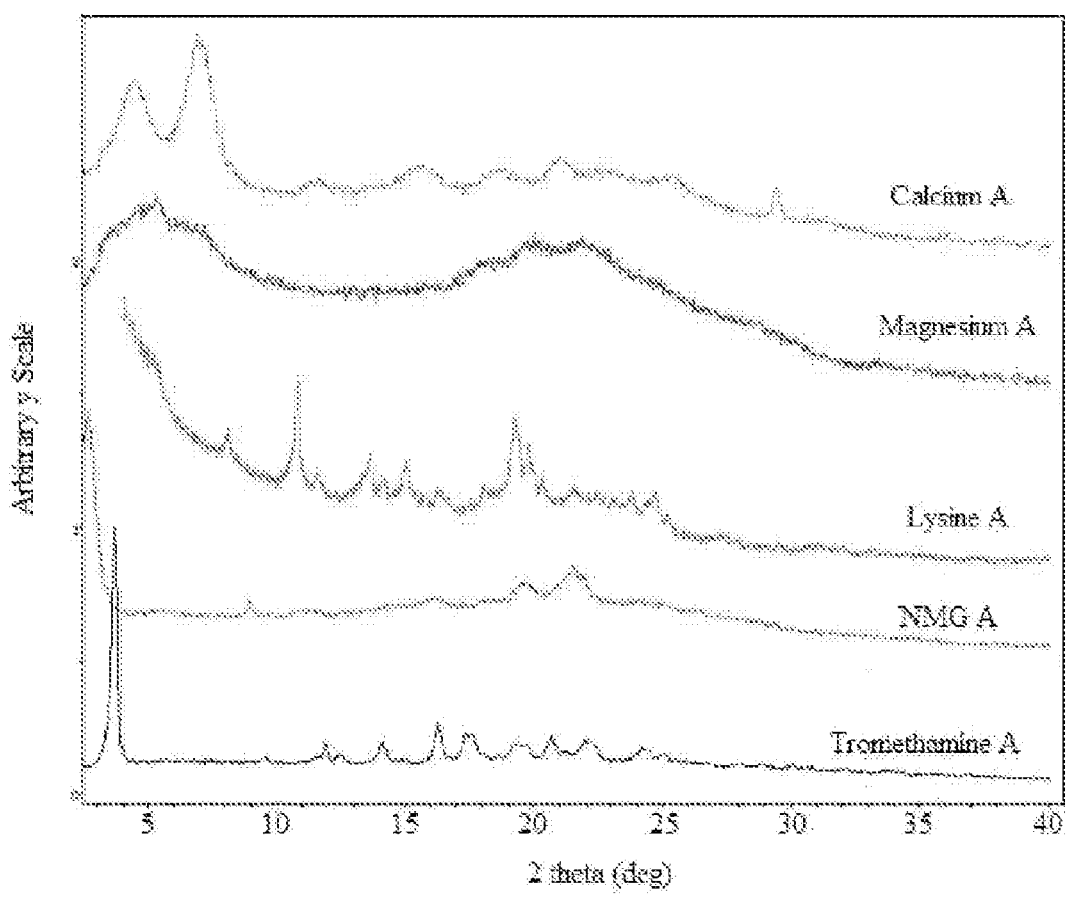
FIG. 14. XRPD Patterns of Salts of (S)-4'-(OH)-DADFT-PE: the calcium A, magnesium A, lysine A, NMG A, and tromethamine A salts (from top to bottom). Degrees θ-2θ on the abscissa are plotted against an arbitrary Y value on the ordinate.

In further embodiments, the salt of Formula III has a X-ray powder diffraction pattern which is at least 70%, at least 80%, at least 90%, or at least 95% identical to that shown in FIG. 13.

Figure 19:
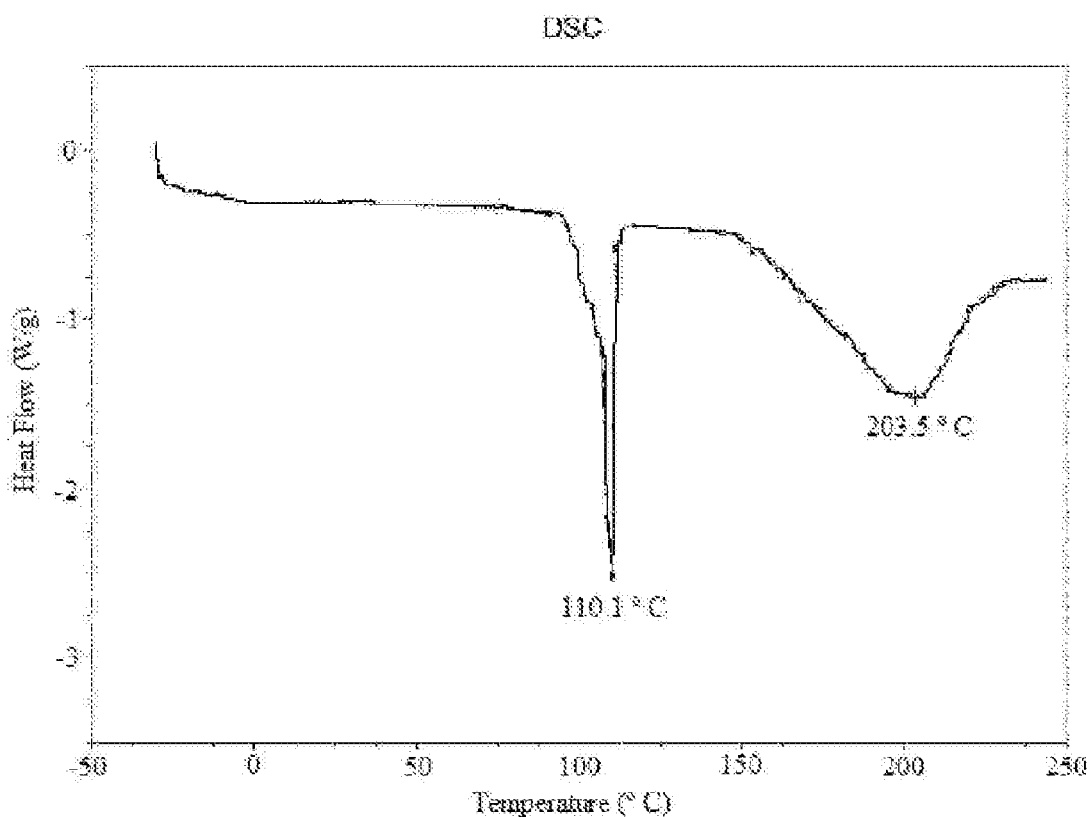
FIG. 19. DSC spectrum of (S)-4'-(OH)-DADFT-PE tromethamine salt.

In further embodiments, the salt of Formula III has a differential scanning calorimetry thermogram which is at least 70%, at least 80%, at least 90%, or at least 95% identical to that shown in FIG. 19.

Figure 20:
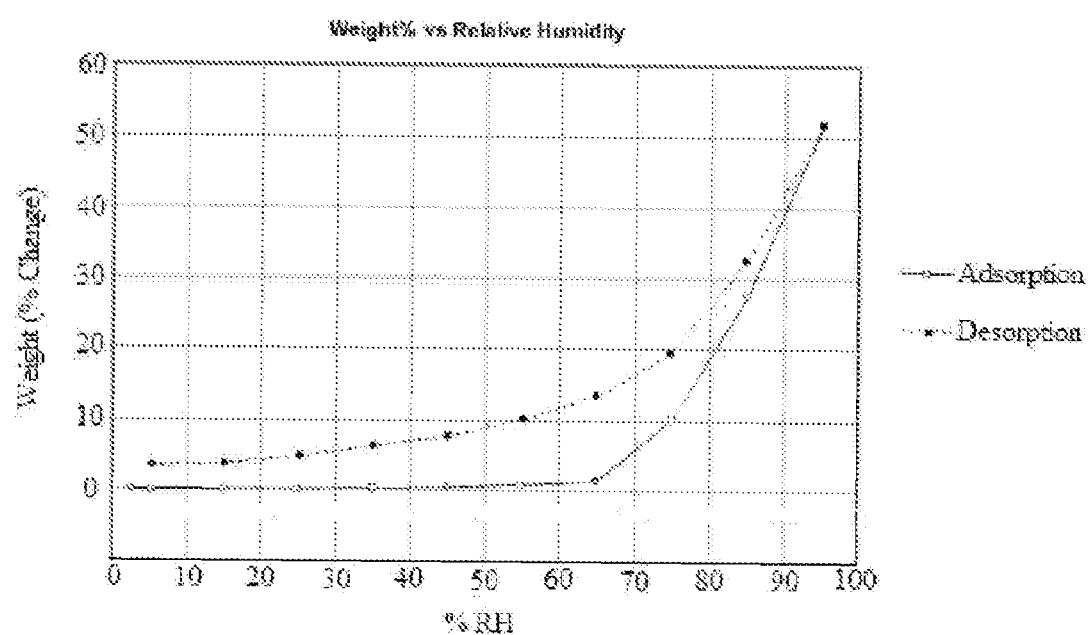
FIG. 20. Dynamic vapor sorption/desorption isotherm of (S)-4'-(OH)-DADFT-PE tromethamine salt.

In further embodiments, the salt of Formula III has a dynamic vapor sorption/desorption (DVS) spectrum which is at least 70%, at least 80%, at least 90%, or at least 95% identical to that shown in FIG. 20.

In further embodiments, the salt of Formula III has an aqueous solubility at near-physiologic pH of between 0.3 mg/ml and 150 mg/ml.

In certain embodiments, salts and polymorphs thereof have structural formula IV:

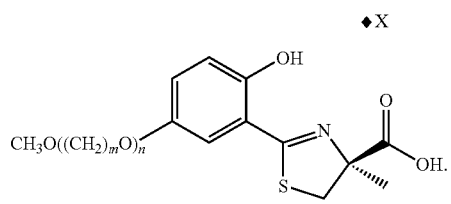

IV

In further embodiments, salts and polymorphs thereof have structural formula IVa:

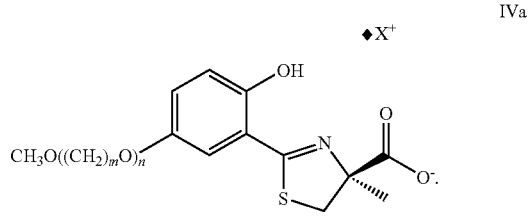

IVa

In certain embodiments, salts and polymorphs thereof have structural formula V:

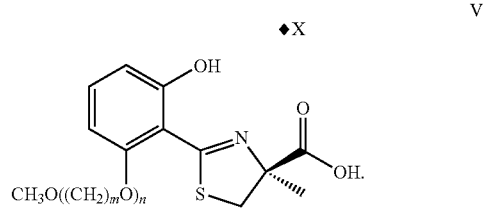

V

In further embodiments, salts and polymorphs thereof have structural formula Va:

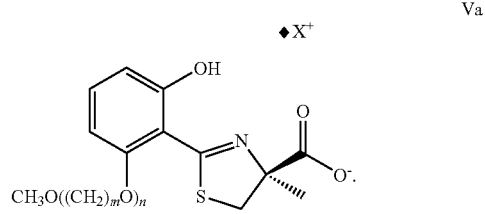

Va

In certain embodiments, salts and polymorphs thereof have structural formula VI:

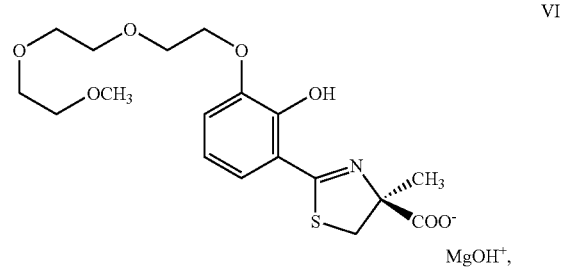

VI or, equivalently, magnesium hydroxide (S)-3'-desazadesferrithiocin polyether (Mg(OH).3'-DADFT-PE), or magnesium (S)-2-(2-hydroxy-3-(2-(2-(2-methoxyethoxy)ethoxy)ethoxy)phenyl)-4-methyl-4,5-dihydrothiazole-4-carboxylate hydroxide.

The compound of formula VI may exist in three substantially crystalline polymorphic forms referred to hereafter as Forms A-C, as well as an amorphous form, which differ from each other in their stability, physicochemical properties, and spectral characteristics.

Accordingly, the polymorphic forms can be characterized by powder X-ray diffraction (XRPD) patterns, differential vapor sorption/desorption (DVS), thermogravimetric analysis (TGA), and differential scanning calorimetry (DSC).

Also provided is a novel polymorph Form A of a compound of formula VI is provided.

In certain embodiments disclosed herein, characterizing data for Form A of a compound of formula VI as obtained by an X-ray powder diffraction (XRPD) pattern is shown in FIG. 7.

Also provided is a novel amorphous form of a compound of formula VI is provided.

In certain embodiments disclosed herein, characterizing data for the amorphous form of a compound of formula VI as obtained by an X-ray powder diffraction (XRPD) pattern is shown in FIG. 7.

Also provided is a novel polymorph Form B of a compound of formula VI is provided.

In certain embodiments disclosed herein, characterizing data for Form B of a compound of formula VI as obtained by an X-ray powder diffraction (XRPD) pattern is shown in FIG. 8.

In further embodiments, characterizing data for Form B of a compound of formula VI as obtained by a differential scanning calorimetry (DSC) thermogram is shown in FIG. 10.

In yet further embodiments, characterizing data for Form B of a compound of formula VI as obtained by a vapor sorption/desorption (DVS) spectrum is shown in FIG. 11.

Also provided is a novel polymorph Form C of a compound of formula VI is provided.

In certain embodiments disclosed herein, characterizing data for Form C of a compound of formula VI as obtained by an X-ray powder diffraction (XRPD) pattern is shown in FIG. 9.

In certain embodiments, salts and polymorphs thereof have structural formula VII:

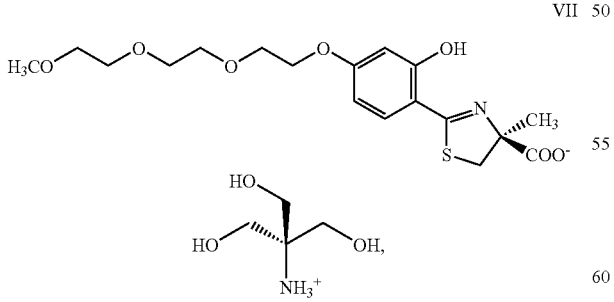

or, equivalently, tromethamine (S)-3'-desazadesferrithiocin polyether (tromethamine.4'-DADFT-PE), or 1,3-dihydroxy-2-(hydroxymethyl)propan-2-aminium (S)-2-(2-hydroxy-4-(2-(2-(2-methoxyethoxy)ethoxy)ethoxy)phenyl)-4-methyl-4,5-dihydrothiazole-4-carboxylate.

In certain embodiments, characterizing data for a compound of formula VII as obtained by X-ray powder diffraction (XRPD) is shown in FIG. 13.

In certain embodiments, characterizing data for a compound of formula VII as obtained by differential scanning calorimetry (DSC) is shown in FIG. 19.

In certain embodiments, characterizing data for a compound of formula VII as obtained by vapor sorption/desorption (DVS) is shown in FIG. 20.

In certain embodiments are provided salts of structural formula II and polymorphs thereof having an aqueous solubility at near-physiologic pH of between 0.3 mg/ml and 70 mg/ml.

In certain embodiments are provided salts of structural formula II and polymorphs thereof having an aqueous solubility at near-physiologic pH of ≧40 mg/ml.

In certain embodiments are provided salts of structural formula II and polymorphs thereof having an aqueous solubility at near-physiologic pH of ≧50 mg/ml.

In certain embodiments are provided salts of structural formula II and polymorphs thereof having an aqueous solubility at simulated gastric pH of 0.05 mg/ml-250 mg/ml.

In certain embodiments are provided salts of structural formula II and polymorphs thereof having an aqueous solubility at near-physiologic pH of between 0.3 mg/ml and 70 mg/ml and having an aqueous solubility at simulated gastric pH of 0.05 mg/ml-250 mg/ml.

In certain embodiments are provided salts of structural formula II and polymorphs thereof having an aqueous solubility at near-physiologic pH (~7.4) of between 0.3 mg/ml and 70 mg/ml and having an aqueous solubility at simulated gastric pH (~pH 1) of 0.05 mg/ml-250 mg/ml.

In certain embodiments are provided salts of structural formula III and polymorphs thereof having an aqueous solubility at near-physiologic pH (~7.4) of between 0.3 mg/ml and 150 mg/ml.

Also provided are pharmaceutical compositions comprising the salt or polymorph thereof as disclosed herein together with at least one pharmaceutically acceptable excipient.

In certain embodiments, the pharmaceutical composition comprises a salt or polymorph thereof having structural formula II

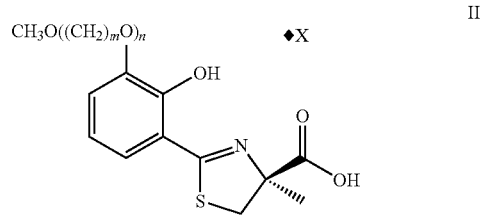

wherein
m is 2 and n is 3; and
wherein the counterion X is chosen from calcium, magnesium, potassium, sodium, zinc, and piperazine.

In further embodiments is provided a pharmaceutical composition comprising magnesium 3'-desazadesferrithiocin polyether hydroxide (Mg(OH).3'-DADFT-PE), or a polymorph thereof, together with at least one pharmaceutically acceptable excipient.

In certain embodiments, the pharmaceutical composition comprises a salt or polymorph thereof having structural formula III

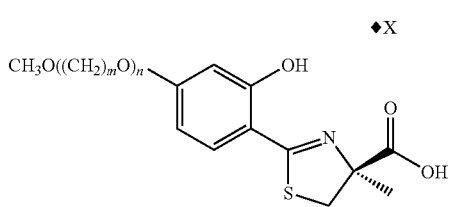

wherein
m is 2 and n is 3; and
the counterion X is chosen from lysine, NMG, tromethamine, calcium, magnesium.

In further embodiments is provided a pharmaceutical composition comprising tromethamine 4'-desazadesferrithiocin polyether hydroxide (tromethamine.4'-DADFT-PE) or a polymorph thereof, together with at least one pharmaceutically acceptable excipient.

In certain embodiments, the pharmaceutical composition comprises magnesium 3'-desazadesferrithiocin polyether hydroxide (Mg(OH).3'-DADFT-PE), or a polymorph thereof, together with at least one pharmaceutically acceptable excipient.

In certain embodiments, the pharmaceutical composition comprises tromethamine 4'-desazadesferrithiocin polyether hydroxide (tromethamine.4'-DADFT-PE) or a polymorph thereof, together with at least one pharmaceutically acceptable excipient.

In certain embodiments are provided a method of treating a pathological condition responsive to chelation, sequestration, or elimination of a trivalent metal in a subject comprising administering to the subject a therapeutically effective amount of a salt or polymorph thereof as disclosed herein 1.

In further embodiments, said trivalent metal is iron.

In further embodiments, said pathological condition is iron overload.

In further embodiments, said pathological condition is the result of mal-distribution or redistribution of iron in the body.

In further embodiments, said pathological condition is chosen from atransferrinemia, aceruloplasminemia, and Fredreich's ataxia.

In further embodiments, said pathological condition is the result of transfusional iron overload.

In further embodiments, said pathological condition is chosen from beta-thalassemia major and intermedia, sickle cell anemia, Diamond-Blackfan anemia, sideroblastic anemia, chronic hemolytic anemias, off-therapy leukemias, bone marrow transplant and myelodysplastic syndrome.

In further embodiments, said pathological condition is a hereditary condition resulting in the excess absorption of dietary iron.

In further embodiments, said pathological condition is chosen from hereditary hemochromatosis and porphyria cutanea tarda.

In further embodiments, said pathological condition is diabetes.

In further embodiments, said pathological condition is an acquired disease that results in excess dietary iron absorption.

In further embodiments, said pathological condition is a liver disease.

In further embodiments, said disease is hepatitis.

In further embodiments, said pathological condition is lanthanide or actinide overload.

In further embodiments, the therapeutically effective amount of a salt or polymorph thereof as disclosed herein that induces the bodily excretion of iron or other trivalent metal is greater than 0.2 mg/kg/d in the subject.

In further embodiments, the therapeutically effective amount of a salt or polymorph thereof as disclosed herein can be given at a dose of at least 10 mg/kg/d without clinically apparent toxic effects on the kidney, bone marrow, thymus, liver, spleen, heart or adrenal glands.

As used herein, the terms below have the meanings indicated.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkynyl," as used herein, alone or in combination, refers to a straight-chain or branched chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The terms "benzo" and "benz," as used herein, alone or in combination, refer to the divalent group C$_6$H$_4$=derived from benzene. Examples include benzothiophene and benzimidazole.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like.

"Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom chosen from O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to OH.

The term "hydroxyalkyl," as used herein, alone or in combination, refers to a hydroxy group attached to the parent molecular moiety through an alkyl group.

The phrase "in the main chain" refers to the longest contiguous or adjacent chain of carbon atoms starting at the point of attachment of a group to the compounds of any one of the formulas disclosed herein.

The term "lower," as used herein, alone or in a combination, where not otherwise specifically defined, means containing from 1 to and including 6 carbon atoms.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "chelation" as used herein means to coordinate (as in a metal ion) with and inactivate. Chelation also includes decorporation, a term which itself encompasses chelation and excretion.

The term "iron-clearing efficiency (ICE)" as used herein refers to the efficaciousness of a given concentration of chelator in clearing iron from the body or one of its organs or parts. Efficaciousness in turn concerns quantity of iron removed from a target system (which may be a whole body, an organ, or other) in a unit of time. Chelators are needed for three clinical situations: for acute iron toxicity from ingestion or infusion of iron; to reduce total body iron secondary to transfusion or excess iron absorption; for maintenance of iron balance after total body iron has been satisfactorily reduces and only daily dietary iron needs to be excreted. In practical terms, therefore, for chronic iron overload secondary to transfusion, the recommendation is that between 0.3 and 0.5 mg Fe/kg body weight of the patient per day need be excreted. For the maintenance treatment, 0.25-1 mg/kg/d is sufficient.

The term "therapeutically acceptable" refers to those compounds (or salts, polymorphs, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. Such salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, zinc, and calcium salts of the compounds disclosed herein, and the like.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium (e.g., NaOH), potassium (e.g., KOH), calcium (including $Ca(OH)_2$), magnesium (including $Mg(OH)_2$ and magnesium acetate), zinc, (including $Zn(OH)_2$ and zinc acetate) and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated.

In certain embodiments, the salts may include lysine, N-methyl glutarate (NMG), tromethamine, calcium, magnesium, potassium, sodium, zinc, and piperazine salts of compounds disclosed herein.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

When the phrase "X is a counterion" is used in structural formulas I, II, III, IV V, and VI herein, and neither the compound nor the counterion is drawn showing explicit ionic character, such ionic character may be inferred and a corresponding charges on each moiety be assumed to be present or absent. For example, if X is a monovalent cation such as $Mg(OH)^+$, it may be inferred that the coupled compound has lost a proton to form an ionic bond with X, despite Formula I being drawn to explicitly show all protons in place. Similarly, when X is an anion, the coupled compound takes on cationic character. The notation is left intentionally ambiguous as to placement and ratios of charges since without extensive physical characterization, such as X-ray crystal diffraction, it is often impossible to know with certainty where on a compound a counterion has bound. Additionally, counterions and compounds may combine in uneven molar ratios to form solid salts.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Described herein are various polymorphic forms such as Form A, Form B, form C, amorphous, and the like. These terms (Form A, Form B, etc. as the case may be) encompass polymorphs that are substantially similar to those described herein. In this context, "substantially similar" means that one of skill in the art would recognize the polymorphs differing insignificantly from those polymorphs as physically characterized herein, or those polymorphs having one or more properties described herein. By way of example, a polymorph encompassed by the term Form A could have an X-ray powder diffraction (XRPD) spectrum which is at least 70%, at least 80%, at least 90%, or at least 95% identical to that shown in the XRPD for Form A. For example, the encompassed polymorph might have at least 80% of the peaks in common with the disclosed Form A (shown in FIG. 7). Alternatively, if the XRPD spectrum is identified by only a few major peaks, the encompassed polymorph might have major peaks at least 80% identical to those shown in an XRPD spectrum. Alternatively, the encompassed polymorph might have an aqueous solubility which is within 80 to 120% that shown herein.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), thermal gravimetric analysis (TGA), dynamic vapor sorption/desorption (DVS), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent. The term "hydrate" refers to a solvate wherein the solvent is water.

The term, "desolvated solvate," as used herein, refers to a crystal form of a substance which can only be made by removing the solvent from a solvate.

The term "amorphous form," as used herein, refers to a noncrystalline form of a substance.

The term "solubility" is generally intended to be synonymous with the term "aqueous solubility," and refers to the ability, and the degree of the ability, of a compound to dissolve in water or an aqueous solvent or buffer, as might be found under physiological conditions. Aqueous solubility is, in and of itself, a useful quantitative measure, but it has additional utility as a correlate and predictor, with some limitations which will be clear to those of skill in the art, of oral bioavailability. In practice, a soluble compound is generally desirable, and the more soluble, the better. There are notable exceptions; for example, certain compounds intended to be administered as depot injections, if stable over time, may actually benefit from low solubility, as this may assist in slow release from the injection site into the plasma. Solubility is typically reported in mg/mL, but other measures, such as g/g, may be used. Solubilities typically deemed acceptable may range from 1 mg/mL into the hundreds or thousands of mg/mL.

Solubility may be measured under varying conditions. For example, it may be measured under conditions similar to those found in the body, such as at gastric pH or at physiologic or near-physiologic pH. "Gastric pH" as used herein means about pH 1. "Near-physiologic pH," as used herein refers to the typical pH of bodily tissues and fluids, such as blood and plasma, or cytoplasm, generally about 7.4.

As used herein, "solid" when referring to a salt form means relatively solid, at room temperature, and/or containing a substantial amount of solids. A solid may be amorphous in form and/or be a solvated solid with some quantity of residual or coordinated of solvent molecules. A crystalline salt is an example of a solid. By way of example, a wax could be considered a solid, whereas an oil would not be.

A "solid composition" as used herein includes a salt of a compound, or a polymorph or amorphous solid form thereof.

While it may be possible for the compounds, salts and polymorphs disclosed herein to be administered as the raw chemical, it is also possible to present them as a pharmaceutical formulation. Accordingly, provided herein are pharmaceutical formulations which comprise one or more of certain compounds, salts and polymorphs disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds, salts and polymorphs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds, salts and polymorphs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds, salts and polymorphs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds, salts and polymorphs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds, salts and polymorphs to allow for the preparation of highly concentrated solutions.

In addition to the formulations described previously, a compound, salt, or polymorph as disclosed herein may also be formulated as a depot preparation. Such long acting formulations may be administered by implantation (for example subcutaneously or intramuscularly) or by intramuscular injection. Thus, for example, the compounds, salts and polymorphs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds, salts and polymorphs may also be formulated in rectal compositions such as suppositories or retention enemas, e.g., containing conventional suppository bases such as cocoa butter, polyethylene glycol, or other glycerides.

Certain compounds, salts and polymorphs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds, salts and polymorphs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds, salts and polymorphs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, $2^{nd}$, J Neuroimmune Pharmacol. 2007 March; 2(1):81-6. Epub 2006 Sep. 15.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds, salts and polymorphs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds, salts and polymorphs which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds, salts and polymorphs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds, salts and polymorphs described herein (or a pharmaceutically acceptable salt, ester, or prodrug thereof) in combination with another therapeutic agent. By way of example only, if one of the side effects experienced by a patient upon receiving one of the compounds herein for the treatment of actinide poisoning is depletion of essential trace minerals required by the body for proper functioning, then it may be appropriate to administer a strong chelating agent in combination with supplements of essential trace minerals required by the body for proper functioning, for example zinc and magnesium, to replace those which will inadvertently be lost to chelation therapy. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for thalassemia involving administration of one of the compounds described herein, increased therapeutic benefit may result by also providing the patient with another therapeutic agent for thalassemia, for example deferoxamine. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain salts and polymorphs as disclosed herein with: deferasirox, deferiprone, deferoxamine, DTPA (diethylene triamine pentaacetic acid), EGTA (ethylene glycol tetraacetic acid), EDTA (ethylenediamine tetraacetic acid), DMSA (dimercaptosuccinic acid), DMPS (dimercapto-propane sulfonate), BAL (dimercaprol), BAPTA (aminophenoxyethane-tetraacetic acid), D-penicillamine, and alpha lipoic acid.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating disorders and symptoms relating to metal toxicity in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of disorders and symptoms relating to metal toxicity.

Specific diseases to be treated by the compounds, compositions, and methods disclosed herein include iron overload or mal-distribution or redistribution of iron in the body such as atransferrinemia, aceruloplasminemia, or Fredreich's ataxia; transfusional iron overload such as with beta-thalassemia major and intermedia, sickle cell anemia, Diamond-Blackfan anemia, sideroblastic anemia, chronic hemolytic anemias, off-therapy leukemias, bone marrow transplant or myelodysplastic syndrome; a hereditary condition resulting in the excess absorption of dietary iron such as hereditary hemochromatosis, or porphyria cutanea tarda; an acquired disease that results in excess dietary iron absorption such as hepatitis; and other liver diseases; lanthanide or actinide acute poisoning or chronic overload.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

All references, patents or applications, U.S. or foreign, cited in the application are hereby incorporated by reference as if written herein in their entireties. Where any inconsistencies arise, material literally disclosed herein controls.

General Synthetic Methods for Preparing Compounds

Certain compounds from which salts and polymorphs as disclosed herein may be formed can be synthesized as described in Bergeron, R J et al., "Design, Synthesis, and Testing of Non-Nephrotoxic Desazadesferrithiocin Polyether Analogues," *J Med. Chem.* 2008, 51(13), 3913-23.

The following methods can be used to practice the present invention.

EXPERIMENTAL METHODS

Salt Screen Experiments

Salt screens of (S)-3'-(OH)-DADFT-PE and (S)-4'-(OH)-DADFT-PE, shown below,

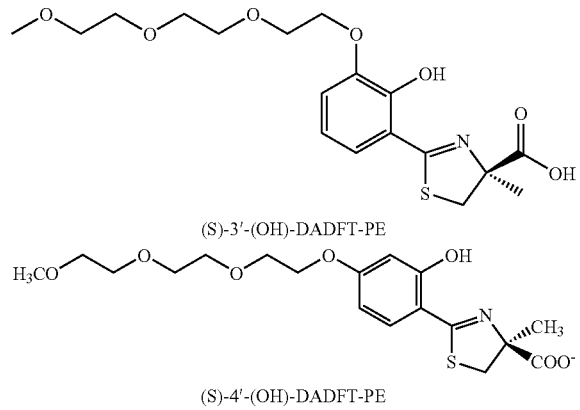

were performed manually in typical glassware. Salt screen experiments were carried out typically using a 1:1 ratio of 4'-(OH)-DADFT-PE or 3'-(OH)-DADFT-PE to salt former. A ratio of 1:2 was occasionally used, such as when calcium and magnesium hydroxides were utilized as salt formers. Experiments were conducted by direct mixing of solvent containing free acid and base. Standard techniques for the formation and isolation of salts were applied, including but not limited to: solution in and addition of different solvents at various rates, heating, stirring, cooling, slow and/or fast evaporation, optionally under N₂ atmosphere, elevated and subambient temperature, rotary evaporation, slurry formation and use of a slurry wheel, isolation and workup of supernatants, trituration, and filtration. The methods could be applied to find salts of any compound of Formula I.

Following isolation, salts were then characterized by one or more standard techniques including but not limited to x-ray powder diffraction (XRPD), single crystal x-ray diffraction (SC-XRD or XRD), nuclear magnetic resonance (NMR), solubility analys,s, and stability testing by moisture sorption/desorption stress analysis and differential scanning calorimetry (DSC).

Throughout the experimental protocols, the following abbreviations may be used. The list below is provided for convenience and is not intended to be inclusive.

| Type | Abbreviations/Acronyms | Full Name/Description |
|---|---|---|
| Solvent | ACN | Acetonitrile |
| | CHCl₃ | Chloroform |
| | DEE | Diethyl Ether |
| | EtOAc | Ethyl Acetate |
| | EtOH | Ethanol |
| | MeOH | Methanol |
| | MTBE | Methyl tert-butyl ether |
| | IPA | Isopropyl alcohol |
| | IPE | Isopropyl ether |
| | THF | Tetrahydrofuran |
| Acid/Base | EDA | Ethylenediamine |
| | 1,2-EDSA | 1,2-Ethanedisulfonic acid |
| | MSA | Methanesulfonic acid |
| | NMG | N-Methyl-D-Glucamine |
| | NaOAc | Sodium acetate |
| | p-TSA monohydrate | p-Toluenesulfonic acid, monohydrate |
| Methods | CCS | Crash Cooling of a solution |
| | FC | Fast cooling |
| | FE | Fast evaporation |
| | FPE | Fast, partial evaporation (volume reduction) |
| | RE | Rotary evaporation |
| | SC | Slow cooling |
| | SE | Slow evaporation |
| | VD | Vapor diffusion |
| Techniques | DSC | Differential scanning calorimetry |
| | NMR | Nuclear magnetic resonance spectroscopy |
| | TGA | Thermogravimetric analysis |
| | XRPD | X-ray powder diffraction |
| Other | API | Active pharmaceutical ingredient 4'-(OH)-DADFT-PE |
| | B\E | Birefringence/extinction |
| | IS | Insufficient amount for XRPD |
| | NP | No peak |
| | NS | No solids |
| | Ppt | Precipitation |
| | RH | Relative Humidity |
| | RT | Room Temperature |
| | VF | Vacuum filtration |
| | VO | Vacuum oven |

Evaporation

Solutions were generated at ambient temperature upon mixing 4'-(OH)-DADFT-PE or 3'-(OH)-DADFT-PE with salt former of specified molar concentration. The solutions were allowed to evaporate to dryness from a vial either covered with aluminum foil containing pinholes (slow evaporation, SE) or left open for fast evaporation (FE). If no solids were formed, additional crystallization techniques were used.

Rotary Evaporation

Solutions were generated at ambient temperature upon mixing 4'-(OH)-DADFT-PE or 3'-(OH)-DADFT-PE with salt former of specified molar concentration. The solvents were then removed using a rotary evaporator ($R^E$) at ambient or elevated temperature. If a film resulted, additional crystallization techniques were used.

Cooling Experiments

Solutions or suspensions were generated at ambient or elevated temperature upon mixing 4'-(OH)-DADFT-PE or 3'-(OH)-DADFT-PE with salt former of specified molar concentration. Solutions or suspensions prepared at ambient were warmed up for further treatment. Resulting mixtures were allowed to cool down to ambient by placing them on an ambient stirring plate (fast cooling, FC) or turning the heating device off (slow cooling, SC). Solids formed were isolated by vacuum filtration. If no solids were collected, additional crystallization techniques were used.

Vapor Diffusion

Solutions were generated at ambient temperature upon mixing 4'-(OH)-DADFT-PE or 3'-(OH)-DADFT-PE with salt former of specified molar concentration. The vial (typically 1 dram) with the sample solution was placed uncapped in a 20 mL scintillation vial with an appropriate antisolvent. The 20 ml vial was then capped and the sample left undisturbed for specified amount of time. If no solids were formed, additional crystallization techniques were used.

Slurry Experiments

Slurry experiments were used as an additional crystallization technique. The solvent was added and the mixture was then agitated in a sealed vial at ambient. After a given amount of time, the solids were isolated by vacuum filtration.

Approximate Solubility

Weighed samples were treated with aliquots of test solvents at room temperature. Samples were typically sonicated between additions to facilitate dissolution. Complete dissolution of the test material in each solvent was determined by visual inspection. Solubility was estimated based on the total volume of solvent used to provide complete dissolution. The actual solubility may be greater than the value calculated due to the incremental addition of solvent and kinetics of dissolution of the material. The solubility is expressed as "less than" if dissolution did not occur during the experiment. The solubility is expressed as "less than" if dissolution occurred after the addition of first aliquot. ps X-Ray Powder Diffraction (XRPD)

XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm, and the samples were analyzed for 300 seconds.

XRPD patterns were collected using a PANalytical X'Pert Pro diffractometer. An incident beam of Cu Kα radiation was produced using a ceramic tube with a long, fine-focus source and a nickel filter. The diffractometer was configured using the symmetric Bragg-Brentano geometry with a reflection stage and a manually operated spinner. Data were collected and analyzed using X'Pert Pro Data Collector software (v. 2.2b). Prior to the analysis, a silicon specimen (NIST SRM 640c) was analyzed to verify the Si 111 peak position. The specimen was prepared as a thin, circular layer centered on a silicon zero-background substrate. Anti-scatter slits were used to minimize the background generated by air scattering. Soller slits were used for the incident and diffracted beams to minimize axial divergence. Diffraction patterns were collected using a scanning position-sensitive detector (X'Celerator) located 240 mm from the specimen.

Differential Scanning Calorimetry

Differential scanning calorimetry (DSC) analyses were performed using a TA Instruments differential scanning calorimeter Q2000. Each sample was placed into an aluminum DSC pan, and the weight accurately recorded. The pan was covered with an inverted lid and crimped. The sample cell was equilibrated at −30° C. and heated under a nitrogen purge at a rate of 10° C./min, up to a final temperature of 250° C. Indium metal was used as the calibration standard.

Thermogravimetric Analysis

Thermogravimetric (TG) analyses were performed using a TA Instruments Q5000 and 2950 thermogravimetric analyzers. Each sample was placed in an aluminum sample pan and inserted into the TG furnace. The furnace was heated under nitrogen at a rate of 10° C./min, up to a final temperature of 350° C. Nickel and Alumel were used as the calibration standards.

Moisture Sorption Analysis

Moisture sorption/desorption (DVS) data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Nuclear Magnetic Resonance Spectroscopy (NMR)

Solution $_1$H-NMR spectra were acquired at SSCI with a Varian UNITYINOVA-400 spectrometer. All samples were prepared in deuterated dimethyl sulfoxide (DMSO). The data acquisition parameters are available on the first plot of the spectrum for each sample, presented in the data section.

The invention is further illustrated by the following examples.

EXAMPLE 1

Attempts to Produce Salts of (S)-3'-(OH)-DADFT-PE

The results of an initial screen of salts of a representative compound, (S)-3'-(OH)-DADFT-PE, are given below in Table 1. Approximately 52 experiments were performed.

TABLE 1

| Base (Approximate molar ratio of API/base) | Conditions | Description | XRPD Result |
|---|---|---|---|
| Betaine | API solution in MeOH was added to base solution in MeOH, SE/FE N$_2$, centrivap: yellow gel with dendridic rosettes/splinters: B/E. Let stand 5 days: no change; MeOH vapor stressed for 37 days. | Yellow tacky oil | — |
| Choline hydroxide | API solution in MeOH was added to aqueous solution of base with minimal water, SE/FE N$_2$, centrivap: clear, auburn gel. Let stand 5 days: no change. MeOH vapor stressed for 37 days. | Yellow tacky oil | — |
| Diethanolamine | API solution in EtOH was added to base, SE/FE N$_2$ to gel, ether added, refrigerated for 42 days. | Yellow oil in clear solution | — |
| Diethylamine (1:1) | API solution in MeOH was added to base, SE/FE N$_2$, centrivap: yellow gel. Let stand 5 days: no change MeOH vapor stressed for 37 days. | Yellow tacky oil | — |
| Ethanolamine (1:1) | API solution in EtOH was added to base, SE/FE N$_2$ to gel, ether added, refrigerated for 42 days. | Yellow oily drops in clear solution | — |
| Hydroxyethyl Morpholine (1:1) | API solution in MeOH was added to base, SE/FE N$_2$, centrivap: yellow gel. Let stand 5 days: no change MeOH vapor stressed for 37 days. | Yellow tacky oil | — |
| Hydroxyethyl Pyrrolidine (1:1) | SE/FE N$_2$, centrivap: yellow gel. Let stand 5 days: no change MeOH vapor stressed for 37 days. | Yellow tacky oil | — |
| Imidazole (1:1) | API solution in EtOH was added to base, SE/FE N$_2$ to gel, ether added, refrigerated for 42 days. | Yellow oily drops in clear solution | — |

TABLE 1-continued

| Base (Approximate molar ratio of API/base) | Conditions | Description | XRPD Result |
|---|---|---|---|
| N-Methyl-d-glucamine (NMG) (1:1) | API solution in MeOH was added to base slurry in MeOH, clear solution. SE/FE N$_2$, centrivap: yellow gel. Let stand 5 days: no change MeOH vapor stressed for 37 days. | Yellow tacky oil | — |
| N,N'-Dibenzyl-ethylenediamine (1:1) | 0.5 ml of API solution in MeOH was added to base. Clear solution. FE at RT. The resulting yellow oil was suspended in ether. Oil dissolved. The clear solution was evaporated under N$_2$ stream. The yellow oil was resuspended in hexane. Yellow gel formed. Placed on a slurry wheel for 13 days at RT. | Yellow oily drops in clear solvent | — |
| N,N'-Diethyl-ethanolamine (1:1) | 0.5 ml of API solution in MeOH was added to base. Clear solution. FE at RT. The resulting yellow oil was dried briefly under N$_2$ stream. Ether was added. Placed on a slurry wheel for 13 days at RT. | Yellow oily drops in clear solvent | — |
| Piperazine (1:1) | API solution in EtOH was added to base solution in EtOH, SE/FE N$_2$ | Gel, radial/dendritic clusters of wisps/needle-like particles (B/E) | Unique LC pattern |
| Triethanolamine (1:1) | API solution in EtOH was added to base in EtOH, SE/FE N$_2$ to gel, ether added, refrigerated for 42 days. | Yellow oil in clear solution | — |
|  | 0.5 ml of API solution in MeOH was added to base. Clear solution. FE at RT. The resulting yellow oil was dried briefly under N$_2$ stream. Hexane was added. Placed on a slurry wheel at RT for 13 days. | Yellow oily drops in clear solvent | — |
| Tromethamine (1:1) | API solution in EtOH was added to base in EtOH, SE/FE N$_2$ to gel, ether added, refrigerated for 42 days. | Yellow oil attached to the wall of the vial in clear solution | — |
| Ca(OH)$_2$ (1:1) | Free acid prepared as a 100 mg/mL = 0.250 mmol API/mL stock solution in MeOH. 1. Added 2.0 mL API solution to base slurry in MeOH/H$_2$O (7.3:1, v/v), agitated 16 hours. [pH value of the salt solution was tested: Dissolved aliquot of slurry sediment in H$_2$O: clear, yellow; pH 8/9 (pH paper); control: hazy, water-white; pH 12 (pH paper)]. 2. Decanted supernatant; isolated and dried solids under N$_2$. | 2.6 mg; fine, white solids (B) | Guest |
|  | 1. Centrifuged slurry of above; added 2 mL ether to 0.2 mL aliquot of supernatant. | Flocculent, white precipitate (B) | — |
| Ca(OH)$_2$ (1:1) | 1. Filtered main supernatant on 0.2-µm Teflon. 2. Very slow evaporation under N$_2$ overnight; rotary evaporation. | Cream yellow solids, B (unable to discern morphology) | Amorphous |
| L-Lysine (1:1) | Free acid prepared as a 100 mg/mL = 0.250 mmol API/mL stock solution. 1. Added 3 × 73.1 µL H$_2$O to 0.5 mmol base, sonicated to obtain solution. | Yellow tacky oil |  |

TABLE 1-continued

| Base (Approximate molar ratio of API/base) | Conditions | Description | XRPD Result |
|---|---|---|---|
| | 2. Added 2.0 mL API solution to get clear, gold solution, rotary wheel for ~3 days, very slow evaporation overnight, rotary evaporated at 20-40° C. to get dark, amber oil. 3. Added 4.0 mL ether, rotary wheel for 1 day: immiscible liquids; amber goop on bottom; FE: very viscous, dark amber oil/small aggregates of tiny acicurals above oil (B/E). 4. Added 0.5 mL EtOAc, sonicated. Rotary wheel for 5 days: immiscible liquids; dark amber oil with possible nucleation sites; decanted EtOAc, evaporated residual solvent(s) from oil in RT vacuum oven: viscous, dark amber gel. 5. MeOH vapor stressed for 35 days. | | |
| L-Arginine (1:1) | Free acid prepared as a 100 mg/mL = 0.250 mmol API/mL stock solution. 1. Added 3 × 73.1 μL $H_2O$ to 0.5 mmol base, sonicated to obtain solution. 2. Added 2.0 mL API solution to get clear, gold solution, rotary wheel for ~3 days, very slow evaporation overnight, rotary evaporated at 20-40° C. to get dark, amber oil. 3. Added 4.0 mL ether, rotary wheel for 1 day: immiscible liquids; amber goop on bottom; FE: viscous, amber oil with B particles. 4. Added 0.5 mL EtOAc, sonicated. Rotary wheel for 5 days: immiscible liquids; dark amber oil; decanted EtOAc, evaporated residual solvent(s) from oil in RT vacuum oven: viscous, dark amber gel. | Yellow tacky oil | — |
| $Mg(OH)_2$ (2:1) | Free acid prepared as a 100 mg/mL = 0.250 mmol API/mL stock solution in MeOH. 1. Added 2.0 mL API solution to base slurry in MeOH/$H_2O$ (11.3:1, v/v), agitated 16 hours. [pH value of the salt solution was tested: Dissolved aliquot of slurry sediment in $H_2O$: hazy; pH 5/6 (pH paper); control: very hazy, white; pH 8 (pH paper)]. 2. Decanted supernatant; isolated and dried solids under $N_2$. | Off-white solids | Guest |
| $Mg(OH)_2$ (2:1) | Centrifuged slurry; added 3 mL ether to 0.2 mL aliquot of supernatant. | No precipitation | — |
| $Mg(OH)_2$ (2:1) | 1. Filtered main supernatant on 0.2-μm Teflon. 2. Very slow evaporation under $N_2$ overnight, rotary evaporated to obtain thick, brown oil. 3. Added 10 mL ether, triturated 7 days on rotary wheel: soft, dark tan solids; cloudy, gray supernatant; walls have B/E where spatula made | Brown solids | Partial crystalline (Form A) |

TABLE 1-continued

| Base (Approximate molar ratio of API/base) | Conditions | Description | XRPD Result |
|---|---|---|---|
| | contact with tan film. 4. Mixed on a rotary wheel for 2 additional days, centrifuged: Vial broke in centrifuge tube. Recovered brown solids, air-dried: ~0.08 g. | | |
| Mg(OH)$_2$ (2:1) | Residue from supernatant (from air evaporation) plus MeOH rinse of broken glass: combined, filtered on 0.2-μm Teflon, N$_2$-evaporated to produce dark amber gel (0.0774 g). MeOH vapor stressed for 35 days. | Yellow tacky oil | — |
| Mg(OH)$_2$ (2:1) | 290 mg of API and 44.5 mg Mg(OH)$_2$ in 13 mL of MeOH/water. Mg(OH)$_2$ still persists. Heated to ~45° C., stirred one day. 6 mL of water added. Left to stir at ~45° C. for 3 days. Solution filtered. | Clear solution | — |
| Mg(OH)$_2$ (2:1) | 4 mg of Mg(OH)$_2$ was added to 0.25 ml of API solution (200 mg/ml) in MeOH. 0.75 ml of MeOH added, followed by 0.1 ml of water. Base remained undissolved. Slurry wheel at RT for 4 days, resulted in clear brown solution. Solvent was evaporated under a N$_2$ stream. The brown film was resuspended in ether. Placed on a slurry wheel at RT for 4 hrs. Solvent decanted, solid dried under N$_2$. | Dark yellow solid | Amorphous |
| Mg(OH)$_2$ (2:1) | 282 mg of API and 21.9 mg Mg(OH)$_2$ in 10 mL of MeOH/water. Mg(OH)$_2$ still persists. Heated to ~45° C., stirred one day. 5 mL of water added. Left to stir at ~45° C. for 3 days. Solution filtered. | Clear solution | — |
| Magnesium acetate (1:1) | 27 mg of magnesium acetate was added to 0.25 ml of API solution (200 mg/ml) in ethanol, sonicated, resulted in clear solution. Solvent was evaporated under N$_2$ stream. The remaining yellow film was resuspended in ether. Sonicated, bright yellow solid formed. Solvent was decanted, solid dried under N$_2$ stream. | Bright yellow solid | Amorphous |
| | A subsample of above. Solid was resuspended in ether. Placed on a slurry wheel at RT. | In progress | — |
| Magnesium acetate (1:1) | 27 mg of magnesium acetate was added to 0.25 ml of API solution (200 mg/ml) in IPA, sonicated, resulted in clear solution. Solvent was evaporated under N$_2$ stream. The remaining yellow gel was resuspended in ether. Sonicated, bright yellow solid formed. Solvent was decanted, solid dried under N$_2$ stream. | Bright yellow solid | Amorphous |
| KOH (1:1) | 1. Added 2.0 mL API solution in MeOH to base solution in MeOH (~10 mg base/mL), agitated 16 hours. 2. Added 10 mL ether: no precipitation. 3. Evaporated solvents under N$_2$. | Bright yellow solids, fibrous fan rosettes (B/E) | Unique pattern (Form A) |

TABLE 1-continued

| Base (Approximate molar ratio of API/base) | Conditions | Description | XRPD Result |
|---|---|---|---|
| | 4. Redissolved in 1 mL MeOH. 5. Added 10 mL ether: plumes of intense haze with a few B/E particles. Added incremental amounts of ether to a final volume of 4 mL: stable turbidity for ~3 h with dissipation/solution. 6. VSE/FE under $N_2$ for ~4 days: clear, yellow oil. 7. Triturated in ether on rotary wheel, decanted supernatant, dried solids with $N_2$. | | |
| KOH (1:1) | ~1 eq of KOH was added to the API solution in ethyl acetate. Solution turned turbid after sonication, brown oil formed in yellow cloudy solution. Solvent was evaporated under $N_2$ stream. Brown oil remained unchanged. Stirred at RT. | In progress | — |
| KOH (1:1) | ~1 eq of KOH was added to the API solution in THF. Solution turned clear after sonication. Solvent was evaporated under $N_2$ stream. The resulting light yellow film was resuspended in MTBE, sonicated, light yellow solid formed. Solvent was decanted, the remaining solid was dried under $N_2$ stream. | Light yellow solid | In progress |
| KOH (1:1) | ~1 eq of KOH was added to the API solution in IPA. Sonicated, resulted in clear yellow solution. Solvent was evaporated under $N_2$ stream. To the resulting yellow film was added MTBE. Bright yellow tacky solid formed on the bottom of the vial. Stirred at RT. | In progress | — |
| NaOH (1:1) | API solution in EtOH was added to aqueous solution of base with minimal water, SE, RT vac oven 1 day | Gel, plate-like particles, specks, elongate hexagonal plates, blades (B/E) | Amorphous pattern + NaCl |
| NaOH (1:1) | API solution in EtOH was added to aqueous solution of base with minimal water, SE/stir. (1) | Cloudy yellow liquid | — |
| | Sample (1) above was precipitated with ether to final vol. of EtOH/ether (1:40), refrigerated for 0.5 hour, decanted liquid, RT dry. (2) | Gummy glass (no B/E) | — |
| | RT slurry on an orbit shaker of (2) above. | Yellow oil | — |
| | Solution of (2) above refrig 0.5 hour. Kept in refrigerator for 42 days. | Clear yellow solution | — |
| | Film precipitated from (1) above with heptane to a final vol. of EtOH/heptane (1:50), kept in a freezer for 57 days. | Yellow oil on the bottom of the vial, clear solvent phase on top | — |
| | THF to (1) to a final vol of EtOH/THF (1:50), kept in a freezer for 57 days. | Clear yellow solution | — |
| | Toluene to (1) to a final vol. of EtOH/toluene (1:50), kept in a freezer for 57 days. | Small amount of oily precipitate in a clear yellow solution. A few birefringent specks. | — |

TABLE 1-continued

| Base (Approximate molar ratio of API/base) | Conditions | Description | XRPD Result |
|---|---|---|---|
| NaOH (1:1) | To an API solution in EtOH was added 1,4-dioxane to a final vol. of 1:50 (EtOH/1,4-dioxane), SE in a fume hood. | Yellow oil | — |
| NaOH (1:1) | To an API solution in EtOH was added ether. Refrigerated for 15 days. | Fine needles in dense rosette clusters (B) | Solid deliquesced or passed through upon filtration |
| | EtOH/ether to above, FE under N$_2$. | Yellow gel | Amorphous |
| | Base solution to above. Refrigerated for 15 days. Yellow precipitate on the bottom of the vial. Solvent decanted, solid dried under N$_2$ stream. | Glassy yellow solid | Amorphous |
| NaOH (1:1) | 1. Added 2.0 mL API solution in MeOH to base solution in MeOH (~9 mg base/mL), mixed on a rotary wheel for 16 hours.<br>2. Added 10 mL ether: no precipitation.<br>3. Evaporated solvents under N$_2$ to ~1 mL; repeated dilution with 20 mL ether: let stand overnight: clear solution with a few tiny particles (B, E). Let stand ≧15 h: no change.<br>4. Evaporated solvents under N$_2$. | Tacky, amber film | — |
| | Subjected 3.3 mg of solid from above to MeOH vapor stress. | "feather" plumes (B/E) | In progress |
| | Subjected 3.6 mg of solid from above to ether vapor stress. | Amber gel film | In progress |
| NaOH (1:1) | To 0.5 ml of API solution in MeOH was added 1 N NaOH in water. Clear solution. FE at RT. The resulting yellow oil was dried briefly under N$_2$ stream. Ether was added. Placed on a slurry wheel at RT for 13 days. Solvent was decanted, the remaining gel was dried under N$_2$. Resulted in tacky gel. | Birefringent fine needles in tacky gel (failed to collect) | — |
| NaOH (1:1) | To 0.5 ml of API solution in EtOH was added 1 equivalent of solid NaOH. Slow evaporated at RT while stirring. To the resulting turbid yellow oil was added ether. Continued to stir at RT for 3 days. Tacky yellowish brown precipitate attached to the bottom of the vial. Solvent was decanted. Ether was added, yellowish brown solid formed. Vacuum filtered. Solid deliquesced on the paper filter. Small amount of remaining solid in the vial was dried under N$_2$ stream. | Birefringent specks in yellowish brown solid | Amorphous |
| NaOH (1:1) | To 0.25 ml of API solution in MeOH was added 1 equivalent of solid NaOH, resulted in dark brown solution. The solvent was evaporated under N$_2$ stream, and the resulting brown film was suspended in ether. Yellowish brown solid formed. | Yellowish brown solid (free-flow powder) | Amorphous |

TABLE 1-continued

| Base (Approximate molar ratio of API/base) | Conditions | Description | XRPD Result |
|---|---|---|---|
| | The suspension was further mixed on a slurry wheel at RT for 1 day. Solvent was decanted, the remaining solid was dried under $N_2$ stream. | | |
| NaOH (1:1) | To 0.5 ml of API solution in THF was added 1 equivalent of solid NaOH, resulted in dark brown solution. The solvent was evaporated under $N_2$ stream, and the resulting brown film was suspended in ether. Yellowish brown solid formed. The suspension was further mixed on a slurry wheel at RT for 1 day. Solvent was decanted, the remaining solid was dried under $N_2$ stream. | Dark yellowish brown solid | Amorphous |
| NaOH (1:1) | To 0.25 ml of API solution in IPA was added 1 equivalent of solid NaOH, followed by 0.05 ml of water, resulted in clear solution. The solvent was evaporated under $N_2$ stream, and the resulting yellow film was suspended in ether. Light yellow solid formed. Solvent was decanted, and the remaining solid was dried under $N_2$ stream. | Light brown solid | Amorphous |
| NaOH (1:1) | To 0.25 ml of API solution in ACN was added 1 equivalent of solid NaOH, followed by 0.05 ml of water, resulted in clear solution. The solvent was evaporated under $N_2$ stream, and the resulting yellow film was suspended in ether. Tacky yellow gel formed. The vial was capped, slurried at RT for 1 day. Clear solvent was decanted, and the remaining gel was dried under $N_2$ stream. | Bright yellow solid | Amorphous |
| NaOH (1:1) A solution of 29.2 mg/mL of NaOH in methanol was used | lyophilization of a solution in t-butyl alcohol. (1) exposure of (1) to ambient air (~57% RH) for a few minutes evaporation of a solution of (1) in toluene slurry of (1) in pentane slurry of (1) in 1:1 ethyl ether:pentane | yellow solids solids deliquesced to a yellow oil In progress In progress In progress | — — — — — |
| NaOH (1:1) A solution of 29.2 mg/mL of NaOH in methanol was used | 1. Dissolved starting material in ethyl ether, dried with anhydrous sodium sulfate and filtered. 2. Added 1 eq. of methanolic NaOH and enough methanol to the filtrate to provide a clear solution. 3. Allowed solution to evaporate at room temp from an open vial. (1) Slurry of (1) in toluene at 40° C. | Tacky, yellow material In progress crystalline solids (B/E) embedded in yellow oil | — — |

TABLE 1-continued

| Base (Approximate molar ratio of API/base) | Conditions | Description | XRPD Result |
|---|---|---|---|
| NaOH (1:1) A solution of 292 mg/mL of NaOH in methanol was used | 1. Dissolved starting material in toluene. 2. Added 1 eq of methanolic NaOH. 3. Removed methanol and water by azeotropic distillation. 4. Added heptane to the warm toluene solution and allowed to cool | In progress | — |
| $Zn(OH)_2$ (1:1) | Added 2.0 mL API solution in MeOH to base slurry in MeOH/$H_2O$ (8:1, v/v), agitated 16 hours: clear, pale yellow liquid with ~10 small, opaque chunks (B). Let stand ~2 days; isolate solids. | Massive white solids: small acicular clusters and rosettes (B/E) | Unique pattern |
| | Main supernatant: second crop after ~4 days. | Pale yellow solids: mix of small aciculars and fibrous | Same pattern as 1st crop |
| | Added ~1 mL ether to 0.2 mL aliquot of supernatant. | Massive gel-like ppt on walls; B with areas of E | — |
| $Zn(OH)_2$ (2:1) | 6 mg of zinc hydroxide was suspended in a mixture of MeOH/water (80:20, v/v). 0.25 ml of API solution (200 mg/ml) in MeOH was added to the suspension. Solution turned clear after mixing. Kept at RT for 2 days. Solvent was evaporated under $N_2$ stream. The resulting yellow film was suspended in ether, placed on a slurry wheel at RT for 1 day. Solvent was decanted, the remaining solid was dried under $N_2$ stream. | Yellow solid | Amorphous |
| $Zn(OH)_2$ (2:1) | 0.25 ml of API solution (200 mg/ml) in EtOH was added to 7 mg of zinc hydroxide. 0.25 ml of EtOH was added subsequently. Sonicated, the resulting turbid solution was placed on a slurry wheel at RT for 1 day. Solvent was evaporated under $N_2$ stream. The resulting yellow film was suspended in ether. Clear solution decanted, the remaining solid was dried under $N_2$ stream. | Light yellow solid and dark yellow gel | Amorphous |
| $Zn(OH)_2$ (2:1) | 0.25 ml of API solution (200 mg/ml) in IPA was added to ~7 mg of zinc hydroxide. 0.25 ml of IPA and 0.05 ml of water were added subsequently. Sonicated, resulted in clear solution. FE at RT. To the resulting yellow oil was added ether. Place on a slurry wheel at RT. | In progress | — |
| $Zn(OH)_2$ (2:1) | 0.25 ml of API solution (200 mg/ml) in ACN was added to ~7 mg of zinc hydroxide. 0.25 ml of ACN and 0.05 ml of water were added subsequently. Sonicated, resulted in clear solution. SE at RT. To the resulting yellow gel was added ether. Place on a slurry wheel at RT. | In progress | — |

TABLE 1-continued

| Base (Approximate molar ratio of API/base) | Conditions | Description | XRPD Result |
|---|---|---|---|
| Zn Acetate (1:1) | 24 mg of zinc acetate was added to 0.25 ml of API solution (200 mg/ml) in MeOH. 0.25 ml of MeOH added, followed by 0.1 ml of water. Zinc acetate dissolved. The clear solution was set up for FE at RT. The resulting yellow oil was resuspended in ether. Solvent was decanted, the remaining solid dried under $N_2$. | Light yellow solid | Amorphous |
| Zn Acetate (1:1) | 12 mg of zinc acetate was added to 0.25 ml of API solution (200 mg/ml) in MeOH. Zinc acetate dissolved. The clear solution was set up for FE at RT. The resulting yellow oil was resuspended in ether. Solvent was decanted, the remaining solid dried under $N_2$. | Bright yellow solid | Amorphous |
| $Zn(OH)_2$ (2:1) $Mg(OH)_2$ (2:1) | 7 mg of zinc hydroxide and 4 mg of magnesium hydroxide were added to 0.25 ml of API solution (200 mg/ml) in MeOH. Solid remained after mixing. The suspension was further mixed on a slurry wheel for 2 days. Brown solution with small amount of precipitate on the bottom of the vial. The solvent was evaporated under $N_2$ stream. The resulting brown film was suspended in ether. Light yellow powdery solid formed. Solvent was decanted, the remaining solid was dried under $N_2$ stream. | Light yellow solid | Amorphous |
| $Zn(OH)_2$ (2:1) $Mg(OH)_2$ (2:1) | 6 mg of zinc hydroxide and 4 mg of magnesium hydroxide were added to 0.5 ml of API solution (100 mg/ml) in THF. Solution remained turbid after sonication. The mixture was further mixed on a slurry wheel at RT for 3 days, resulted in clear brown solution. The solvent was evaporated under $N_2$ stream. The resulting brown film was suspended in ether. Yellowish brown solid formed. Solvent was decanted, the remaining solid was dried under $N_2$ stream. | Yellowish brown free flow powder | Disordered Mg salt Form A |
| $Zn(OH)_2$ (2:1) $Mg(OH)_2$ (2:1) | 6 mg of zinc hydroxide and 4 mg of magnesium hydroxide were added to 0.5 ml of API solution (100 mg/ml) in ethanol. Solution remained turbid after sonication. The mixture was further mixed on a slurry wheel at RT for 3 days. White fine powdery precipitate in yellow solution. The solvent was evaporated under $N_2$ stream. The resulting yellow film was suspended in ether. Light yellow solid formed. Solvent was decanted, the remaining solid was dried under $N_2$ stream. | Yellow solid | Amorphous + $Mg(OH)_2$ peaks |

TABLE 1-continued

| Base (Approximate molar ratio of API/base) | Conditions | Description | XRPD Result |
|---|---|---|---|
| Zn(OH)$_2$ (4:1) Mg(OH)$_2$ (4:1) | 3 mg of zinc hydroxide and 2 mg of magnesium hydroxide were added to 0.5 ml of API solution (100 mg/ml) in ethanol. Solution remained turbid after sonication. The mixture was further mixed on a slurry wheel at RT for 3 days. White fine powder precipitated on the bottom of the vial. The solvent was evaporated under N$_2$ stream. The resulting yellow film was suspended in ether. Light yellow solid formed. Solvent was decanted, the remaining solid was dried under N$_2$ stream . . . | Yellow solid | Amorphous + Mg(OH)$_2$ peaks |

EXAMPLE 2

Calcium Salt of (S)-3'-(OH)-DADFT-PE

The x-ray amorphous calcium salt was generated by mixing equal molar ratio of API solution in methanol with base slurry in MeOH/H$_2$O (7.3:1, v/v). The filtered supernatant was slowly evaporated under N$_2$, followed by rotary evaporation. The calcium salt remained physically unchanged when exposed to 75% RH for 3 days; however, when it was stored at room temperature for 15 days, a color change was observed. The aqueous solubility of the calcium salt is very low, less than 2 mg/ml.

EXAMPLE 3

Magnesium Salt of (S)-3'-(OH)-DADFT-PE

The partial crystalline magnesium salt was generated by mixing equal molar ratio of API solution in methanol with base slurry in MeOH/H$_2$O (11:1, v/v). The filtered supernatant was slowly evaporated under N$_2$, followed by rotary evaporation. Solid was generated by anti-solvent precipitation in ether. A large scale preparation of the magnesium was performed by mixing equal molar ratio of API solution in methanol with base suspension in methanol/water. The filtered supernatant was fast evaporated at ambient, and then dried under N$_2$. Solid was generated by anti-solvent precipitation in ether.

The solution proton NMR spectrum of the magnesium salt is consistent with the chemical structure of the API. Significant peak shifts were observed for all the protons in the API structure, implying salt formation. A sharp peak at ~3.3 ppm was assigned to water. Solvent DMSO was also observed at ~2.5 ppm.

The magnesium salt appears to be non-hygroscopic. It did not deliquesce when exposed to 75% RH for 8 days, and the XRPD pattern remained unchanged. The salt exhibits relatively high solubility in water ($\geq$48 mg/ml).

The DSC thermogram curve of the magnesium salt Form B (FIG. 10) exhibits two broad endotherms. The major endotherm at approximately 79° C. is most likely due to the volatilization of water and is associated with a TG weight loss of ~16%. This weight loss is significantly higher than that observed for Form A. The nature of the minor endotherm at approximately 153° C. is unknown; however, it may be related to a phase transition. A TG weight loss of 2.2% is associated with this event.

The DVS data (FIG. 11) suggests that Form B is hygroscopic. The material exhibits 10.8% weight loss upon equilibrium at 5% RH. During the sorption step, the material exhibits a weight gain of 5.7% from 5% to 65% RH and an additional 21.2% weight above 65% RH without reaching equilibrium weight. This indicates that higher weight gains may be possible. A weight loss of 26.6% was observed upon desorption.

The results of an initial polymorph screen crystallization experiments of the amorphous form of the magnesium salt of (S)-3'-(OH)-DADFT-PE are given below in Table 2, wherein FE stands for fast evaporation, SE stands for slow evaporation and LC stands for low crystallinity.

TABLE 2

| Solvent | Conditions | Description | XRPD Result |
|---|---|---|---|
| Acetone | FE | Yellow solid | A (LC) |
|  | SE | Yellow film | Amorphous |
| ACN | FE | Yellow oil | — |
|  | SE | Yellow film | Amorphous |
| DCM | FE | Yellow oil | — |
|  | SE | Yellow film | Amorphous |
| 1,4-Dioxane | FE | Yellow oil | — |
|  | SE | Yellow film | Amorphous |
| EtOH | Slurry (ambient) | Clear yellow solution | — |
| EtOAc | FE | Yellow oil | — |
|  | SE | Yellow solid | A (LC) |
| Ethyl Ether | Slurry (ambient) | Yellow solid | — |
| HFIPA | FE | Yellow oil | — |
|  | SE | Yellow oil | Amorphous |
| Hexanes | Slurry (ambient) | Yellow solid | — |
| IPA | Slurry (ambient) | White and yellow solid | — |
| MeOH | FE | Yellow oil | — |
|  | SE | Yellow oil | Amorphous |
| MEK | FE | Yellow oil | — |
|  | SE | Yellow solid | A (LC) |
| THF | FE | Yellow oil | — |
|  | SE | Yellow film | Amorphous |
| Toluene | FE | Yellow film | Amorphous |
|  | SE | Yellow solid | Amorphous |
| TFE | FE | Yellow oil | — |
|  | SE | Yellow film | Amorphous |
| Water | FE | Yellow oil | — |
|  | SE | Yellow solution | — |

The results of an initial polymorph screen crystallization experiments of (S)-3'-(OH)-DADFT-PE magnesium salt form A are given below in Table 3, wherein FE stands for fast evaporation and SE stands for slow evaporation.

TABLE 3

| Solvent | Conditions | Description | XRPD Result |
|---|---|---|---|
| Heptane/MeOH | SE | Tan solid | B |
| IPA/DCM | SE | Off-white solid | A |
| IPA/MeOH | FE | Tan solid | B |

The results of antisolvent precipitation experiments of (S)-3'-(OH)-DADFT-PE magnesium salt form A are given below in Table 4.

TABLE 4

| Solvent | Antisolvent | Description | XRPD Result |
|---|---|---|---|
| MeOH | Ether | White solid | A |
| MeOH | IPA | Yellow solid | A |
| Water | IPA | Yellow solid | B |

The results of slow cool crystallization experiments of (S)-3'-(OH)-DADFT-PE magnesium salt form A are given below in Table 5, wherein SC stands for slow cool, RT stands for room temperature, LC stands for low crystallinity, and IS stands for insufficient solid.

TABLE 5

| Solvent | Conditions | Description | XRPD Result |
|---|---|---|---|
| ACN | SC (~60° C. to RT) | Yellow solid | A (LC) |
| HFIPA | SC (~60° C. to RT) | No solid | — |
| MeOH | SC (~60° C. to RT) | White solid | IS |
| TFE | SC (~60° C. to RT) | No solid | — |
| THF | SC (~60° C. to RT) | Yellow solid | A (LC) |
| Water | SC (~60° C. to RT) | No solid | — |
| H$_2$O/IPA (1:1) | SC (~60° C. to RT) | No solid | — |
| MeOH/Acetone (1:1) | SC (~60° C. to RT) | No solid | — |
| EtOH/H$_2$O (1:1) | SC (~60° C. to RT) | No solid | — |

The results of ambient solution experiments of amorphous (S)-3'-(OH)-DADFT-PE magnesium salt are given below in Table 6, wherein LC stands for low crystallinity.

TABLE 6

| Solvent | Antisolvent | Description | XRPD Result |
|---|---|---|---|
| Acetone | — | Brown oil | — |
| ACN | Hexanes | White and yellow solid | A |
|  | Ethyl Ether | White solid | A |
|  | Ethyl Ether | Yellow solid | — |
| DCM | Hexanes | Yellow solid | Amorphous |
| 1,4-Dioxane | Hexanes | White cloudy solution | — |
| EtOAc | Hexanes | White solid | A |
|  | Hexanes | Yellow solid | A |
| HFIPA | Hexanes | Yellow film | — |
| MeOH | Ethyl Ether | No solid | — |
| MEK | Hexanes | Yellow solid | A (LC) |
|  | Hexanes | Yellow solid | A (LC) |
| THF | Hexanes | Off-White solid | A (LC) |
|  | Hexanes | Yellow solid | A (LC) |
| Toluene | Hexanes | Yellow cloudy solution | — |
| TFE | Hexanes | No solid | — |

The results of slurry experiments of (S)-3'-(OH)-DADFT-PE magnesium salt form A are given below in Table 7, wherein d stands for day, and IS stands for insufficient solid.

TABLE 7

| Solvent | Temp/Time | Description | XRPD Result |
|---|---|---|---|
| Acetone | 60° C./4 d | Off-white solid | A |
| 1,4-Dioxane | 60° C./4 d | White solid | C |
| EtOAc | 60° C./4 d | White solid | A |
| IPA | 60° C./4 d | Light yellow solid | Amorphous |
| Toluene | Ambient | White solid | A |
| Water | Ambient | Yellow solid | B |
| Water | 60° C./1 d | Yellow solid | Amorphous |
| ACN/THF (1:1) | 60° C./4 d | Yellow solid | A + peaks |
| EtOH/H$_2$O (1:9) | Ambient | White solid | IS |
| EtOH/H$_2$O (1:1) | Ambient | White solid | IS |
| EtOH/H$_2$O (9:1) | Ambient | Yellow solid | A |
| Heptane/DCM (2:8) | Ambient | Yellow solid | A (LC) |
| Heptane/EtOH (2:8) | Ambient | White solid | Amorphous |
| IPA/Acetone (1:1) | Ambient | White solid | IS |
| IPA/Acetone (2:8) | Ambient | White solid | A |
| IPA/EtOAc (2:8) | Ambient | White solid | A |
| IPA/Ether (2:8) | Ambient | White solid | A |

The results of vapor stress experiments of amorphous (S)-3'-(OH)-DADFT-PE magnesium salt are given below in Table 8, wherein LC stands for low crystallinity and IS stands for insufficient solid

TABLE 8

| Solvent | Description | XRPD Result |
|---|---|---|
| Acetone | Yellow slurry | A (LC) |
| ACN | Yellow oil | — |
| DCM | Yellow solid | IS |
| 1,4-Dioxane | Yellow solid | IS |
| EtOH | Yellow oil | — |
| EtOAc | Yellow solid | IS |
| HFIPA | Yellow oil | — |
| IPA | Yellow oil | — |
| MeOH | Yellow oil | — |
| MEK | Yellow solid | IS |
| THF | Yellow oil | — |
| Toluene | Yellow oil | — |
| TFE | Yellow oil | — |
| Water | Yellow oil | — |

The results of vapor diffusion experiments of amorphous (ω-3'-(OH)-DADFT-PE magnesium salt are given below in Table 9, wherein LC stands for low crystallinity.

TABLE 9

| Solvent | Antisolvent | Description | XRPD Result |
|---|---|---|---|
| Acetone | Hexanes | Yellow solid | A (LC) |
| ACN | Ethyl Ether | Yellow solution | — |
| DCM | Hexanes | Yellow solid | A (LC) |
|  | Hexanes | Yellow solid | A (LC) |
| 1,4-Dioxane | Hexanes | White solid | — |
| EtOAc | Hexanes | White solid | A (LC) |
|  | Hexanes | Yellow solid | A (LC) |
| HFIPA | Ethyl Ether | Yellow solution | — |
| MeOH | Ethyl Ether | Fine cloudy layer of solid | — |

TABLE 9-continued

| Solvent | Antisolvent | Description | XRPD Result |
|---|---|---|---|
| MEK | Hexanes | Yellow solid | Amorphous |
| THF | Hexanes | Yellow and brown solid | A (LC) |
|  | Hexanes | Yellow solid | A (LC) |
| Toluene | Hexanes | Yellow solid | A (LC) |
| TFE | Ethyl Ether | Fine cloudy layer of solid | — |

The results of solvent grinding experiments of (S)-3'-(OH)-DADFT-PE magnesium salt form A are given below in Table 10, wherein LC stands for low crystallinity.

TABLE 10

| Solvent | Description | XRPD Result |
|---|---|---|
| Acetone | Off-white solid | A |
| ACN | Off-white solid | A |
| 1,4-Dioxane | Light purple solid | C |
| 1,4-Dioxane | Light brown solid | C |
| Ethanol | Off-white solid | A |
| EtOAc | Light purple solid | A |
| IPA | Light purple solid | A |
| THF | Light brown solid | A |
| Water | Off-white solid | B |
| Water | Light brown solid | B |
| — | Off-white solid | A (LC) |

EXAMPLE 4

Sodium Salt of (S)-3'-(OH)-DADFT-PE

The X-ray amorphous sodium salt was generated by mixing equal molar ratio of API solution in ethanol with base solution in water. Slow evaporated sample was further dried in vacuum oven.

The proton NMR spectrum of the sodium salt confirms the integrity of the API. Significant peak shifting and broadening were observed for the aromatic protons. Peak shifting was also observed for protons in the vicinity of the —COOH group, implying salt formation. A sharp peak at ~3.3 ppm was assigned to water. Solvent DMSO was also observed at ~2.5 ppm.

The sodium salt appears to be non-hygroscopic. It remained physically unchanged when exposed to 75% RH for 3 days.

EXAMPLE 5

Piperazine Salt of (S)-3'-(OH)-DADFT-PE

The low crystallinity piperazine salt was generated by mixing equal molar ratio of API solution in ethanol with base solution in ethanol, followed by slow and fast evaporation under $N_2$. The piperazine salt appears to be hygroscopic. It deliquesced when exposed to 75% RH for 3 days.

EXAMPLE 6

Potassium Salt of (S)-3'-(OH)-DADFT-PE

Form A of the potassium salt was generated by mixing equal molar ratio of API solution in methanol with base solution in methanol. Solid salt was collected by anti-solvent precipitation in ether.

The DVS data of the potassium salt Form A (FIG. 4) suggest that the potassium salt is extremely hygroscopic. The material exhibits a weigh gain of 67.7% during the sorption step from 5% to 95% RH, and weigh loss of 63.4% during the desorption step from 95% to 5% RH, resulted in hygroscopic material (tacky, yellow, gel-like solids). A plateau was observed in the absorption curve between 45 and 65% RH with an average percentage weight loss of 8.7%, corresponding to 2 moles of water per API.

Deliquescence was observed during DVS measurement. Complete deliquesce was also observed when exposed to 75% RH for 3 days. The post-DVS sample recrystallized to a new form, termed Form B, when exposed to 53% RH for 11 days.

Potassium salt Form A exhibits relatively high aqueous solubility ($\geqq$48 mg/ml) and other test solvents.

Potassium salt Form B was obtained from post-DVS sample exposed to 53% RH as described above. Form B was also obtained by exposing Form A to 53% RH for 11 days at room temperature. Form B was also generated directly from a mixture of methanol/water (54% RH) by fast cooling from RT to refrigerator or from 60° C. to RT as shown below in Table 11.

TABLE 11

| Conditions | Description | XRPD Result |
|---|---|---|
| 10 µl of MeOH/water (72:28, v/v) was added to 17 mg of potassium salt Form A. Solid dissolved. Kept in refrigerator for 1 day. | Microcrystals in yellow oil | Form B |
| 5 µl of MeOH/water (72:28, v/v) was added to 14 mg of potassium salt Form A. Sample was heated to ~60° C. on a dataplate for ~15 min. Solid dissolved. Kept at RT for 1 day. | Needle clusters B/E | Form B |

Figure 4:
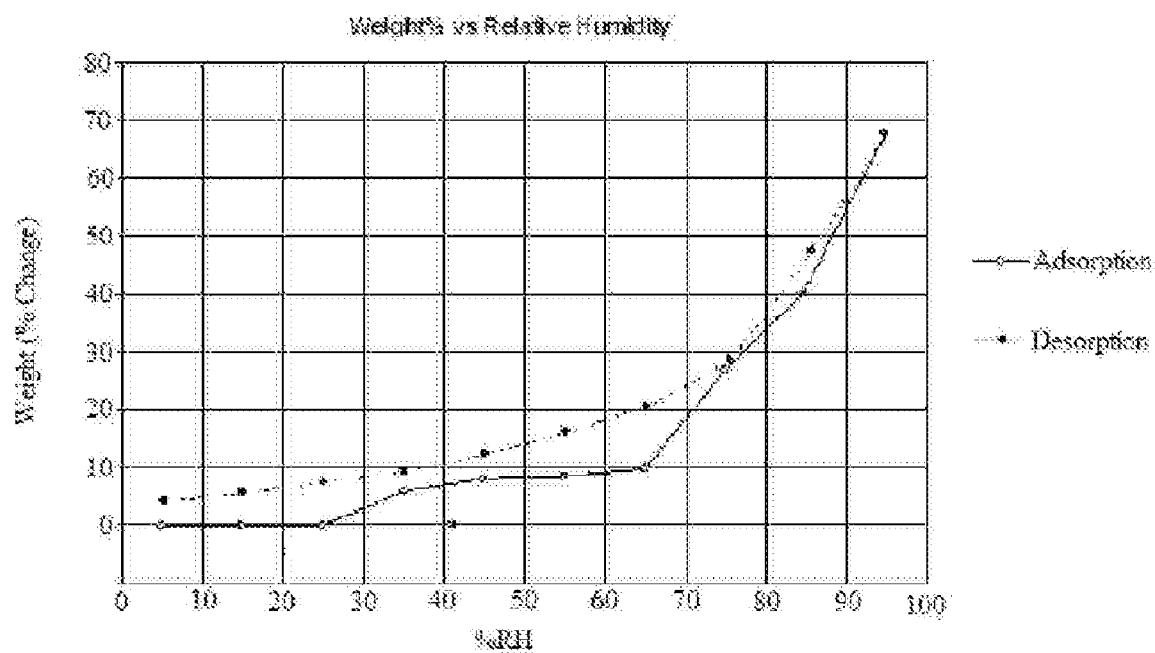
FIG. 4. Dynamic vapor sorption/desorption isotherm of (S)-3'-(OH)-DADFT-PE potassium salt Form A.
Figure 5:
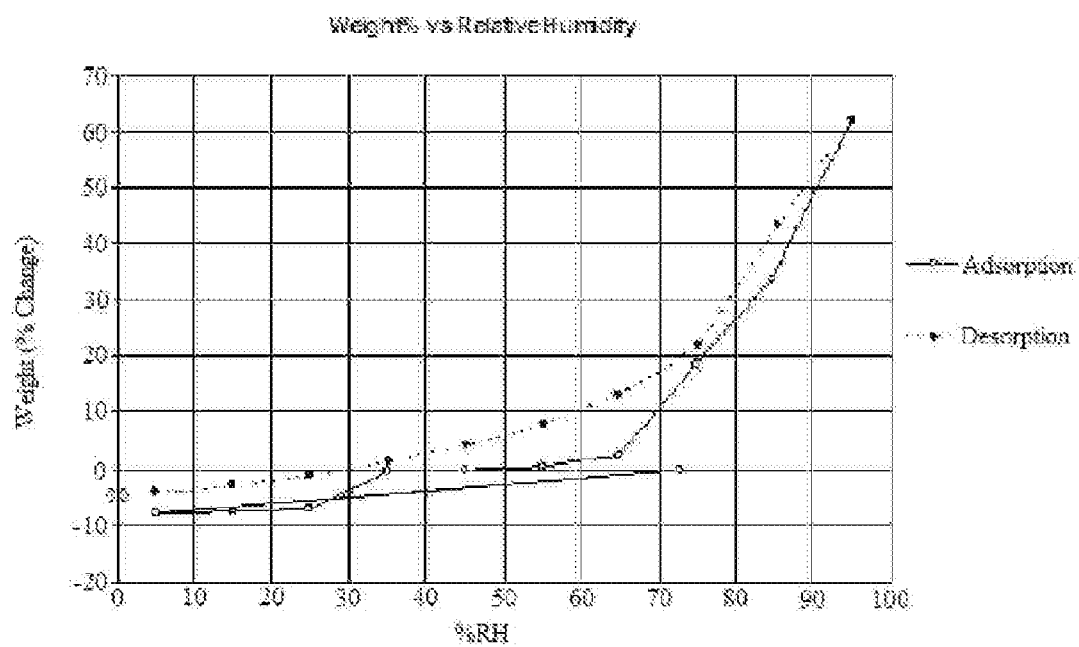
FIG. 5. Dynamic vapor sorption/desorption isotherm of (S)-3'-(OH)-DADFT-PE potassium salt Form B.

The DVS data of the potassium salt Form B (FIG. 5) suggest that Form B is extremely hygroscopic (FIG. 4). The material exhibits a weigh gain of ~70% during the sorption step from 5% to 95% RH, and weigh loss of ~66% during the desorption step from 95% to 5% RH, resulted in deliquesced material. A plateau was observed in the absorption curve between 35 and 65% RH with an average percentage weight gain of ~8%, corresponding to 2 moles of water per API.

Form B appears to be unstable. Form conversion occurred when exposed to low humidity ($P_2O_5$) or elevated temperature (40° C.). Form B converted to a new form, namely Form C, when exposed to $P_2O_5$ for 6 days. It desolvated into a mixture with Form A when exposed to 40° C. for 6 days.

Form C was obtained by exposing Form B in $P_2O_5$ for 6 days. No further characterization data on this form.

EXAMPLE 7

Abbreviated Polymorph Screen of (S)-3'-(OH)-DADFT-PE Potassium Salt

Potassium salt Form A was subjected to a brief polymorph screen. A large scale preparation was conducted to generate salt for an abbreviated polymorph screen. 3'-DADFT-PE.KOH salt was dissolved in any one of acetonitrile, ethyl acetate/water, isopropyl alcohol, methyl ethyl ketone, or tetrahydrofuran, and subjected to solvent evaporation (drying) either at room temperature or in a convection or vacuum oven, at a temperature from room temperature to 80° C., for up to 20 days. The slow evaporation attempt from acetonitrile at 40° C. in a convection oven was the only method that yielded appreciable solids. Results are shown below in Table 12.

TABLE 12

| Starting material | Solvents | Conditions | Description | XRPD Result |
|---|---|---|---|---|
| Potassium salt | ACN | SE, 40° C. convection oven 20 days | Yellow solid | Crystalline (Form A) |
| | EtOAc H$_2$O | SE, 50° C. vacuum oven 20 days | Yellow oil | — |
| | IPA | SE, 60° C. convection oven 20 days | Yellow gel | — |
| | MEK | RT slurry to solution, SE | Yellow tacky gel | — |
| | THF | SE, RT vacuum oven 2 days, 80° C. convection oven 20 days | Yellow gel | — |
| Potassium salt | Simulated gastric fluid | FE at RT | Yellow tacky oil | — |
| | Acetone | Solvent vapor exposure | Tacky yellow chunks and fine birefringent needles | Mixture of Form A (major) & Form B (minor) |
| | ACN | Solvent vapor exposure | Yellow chunks and birefringent specks | Form B |
| | THF | Solvent vapor exposure | Sample deliquesced (Yellow liquid with birefringent particles) | — |

EXAMPLE 8

Figure 6:
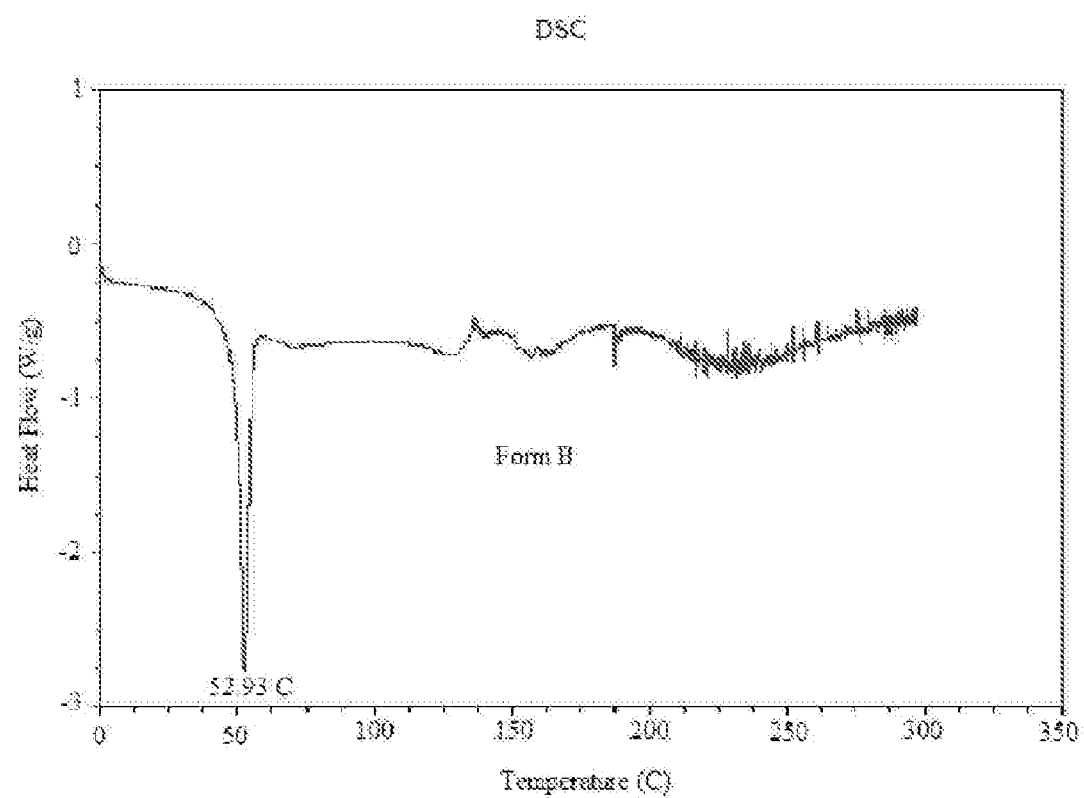
FIG. 6. DSC thermograms of the (S)-3'-(OH)-DADFT-PE Potassium Salt Form B.

Differential Scanning Calorimetry Analysis of (S)-3'-(OH)-DADFT-PE Potassium Salt The thermograms of the potassium salt Form B are displayed in FIG. 6. The DSC curve exhibits a sharp endotherm with a signal maximum at ~53° C., corresponding to a two-step weight loss observed in the TG curve with a total weight loss of ~6.0%. This weight loss is consistent with the 6.7% weight gain observed during form conversion from Form A to Form B.

EXAMPLE 9

Zinc Salt of (S)-3'-(OH)-DADFT-PE

The crystalline zinc salt was generated by mixing equal molar ratio of API solution in methanol with base slurry in MeOH/H$_2$O (8:1, v/v).

The proton NMR spectrum of the zinc salt confirms the integrity of the API. Significant peak shifting was observed for the aromatic protons and protons in the vicinity of the —COOH group, implying salt formation. A sharp peak at ~3.3 ppm was assigned to water. Solvent DMSO was also observed at ~2.5 ppm.

The zinc salt appears to be non-hygroscopic. It remained physically unchanged when exposed to 75% RH for 3 days.

The zinc salt exhibits a low aqueous solubility of ~1 mg/ml.

EXAMPLE 10

Single-crystal X-ray Diffractometric Structural Determination of (S)-3'-(OH)-DADFT-PE Zinc Salt Crystals of a potential Zinc salt of (S)-3'-(OH)-DADFT-PE were prepared at SSCI, Inc. and submitted for single crystal structure analysis. The structure was determined by single crystal X-ray diffraction analysis conducted at the Crystallography Laboratory at Purdue University. The single crystal data collection, structure solution and refinement were not performed according to cGMP specifications.

The quality of the structure obtained is high, as indicated by the R-value of 0.054 (5.4%). Usually R-values in the range of 0.02 to 0.06 are quoted for the most reliably determined structures. The molecule observed in the asymmetric unit of the single crystal structure is consistent with the proposed molecular structure provided in Scheme 1. The asymmetric unit shown in FIG. 3 contains two (S)-3'-(OH)-DADFT-PE molecules, two Zinc anions and two waters of hydration.

The Zinc ion is in the pocket consisting of the phenol, the amine and the acid group (FIG. 3). The acid group is bridging two Zinc molecules and the fifth coordination site is filled by a water molecule.

After a structure is solved the quality of the data should be assessed for its inversion-distinguishing power of the Flack parameter, this is done be an examination of the standard uncertainty (u) of the Flack parameter, which is classified as: strong inversion-distinguishing power. Compound is enantiopure and absolute structure can be assigned directly from the crystal structure.

Therefore, the absolute configuration of the model in FIG. 3 is correct. This structure contains a single chiral centers located at C33 (refer to FIG. 3, ORTEP drawing) which has been assigned as S configuration. This is consistent with the proposed configuration. Additional specifications are given below in Table 13.

TABLE 13

| | |
|---|---|
| Formula | C$_{18}$H$_{25}$NO$_8$SZn |
| formula weight | 480.84 |
| space group | P 1 21 1 (No. 4) |
| a, Å | 11.6979 (7) |
| b, Å | 5.3873 (3) |
| c, Å | 16.2380 (11) |
| b, deg | 90.474 (2) |
| V, Å$^3$ | 1023.29 (11) |
| Z | 2 |
| d$_{calc}$, g cm$^{-3}$ | 1.56 |
| crystal dimensions, mm | 0.50 × 0.10 × 0.05 |
| temperature, K | 150 |
| radiation (wavelength, Å) | Mo K$_a$ (0.71073) |
| Monochromator | graphite |
| linear abs coef, mm$^{-1}$ | 1.369 |
| absorption correction applied | empirical[a] |
| transmission factors: min, max | 0.50, 0.93 |
| Diffractometer | Nonius KappaCCD |
| h, k, l range | −14 to 15 −6 to 6 −21 to 21 |
| 2q range, deg | 4.31-55.00 |
| mosaicity, deg | 1.84 |
| programs used | SHELXTL |
| F$_{000}$ | 500 |
| weighting | 12677 |
| 1/[s$^2$(F$_o^2$) + (0.0597P)$^2$ + 1.1690P where P = (F$_o^2$ + 2F$_c^2$)/3 | |
| data collected: | |
| unique data | 4609 |
| R$_{int}$ | 0.091 |
| data used in refinement | 4609 |
| cutoff used in R-factor calculations | F$_o^2$ > 2.0 s(F$_o^2$) |
| data with I > 2.0 s(I) | 3915 |
| number of variables | 272 |
| largest shift/esd in final cycle | 0 |
| R(F$_o$) | 0.054 |
| R$_w$(F$_o^2$) | 0.117 |
| goodness of fit | 1.054 |
| absolute structure determination | Flack parameter[b] (−0.01(2)) |

EXAMPLE 11

Solubilities of Salts in Various Solvents

Approximate solubilities are calculated based on the total solvent used to give a solution based on visual inspection. Small aliquots of solvent are added to a weighed sample with agitation. Actual solubilities may be greater because of the volume of the solvent portions utilized or a slow rate of dissolution. Solubilities are reported to the nearest mg/mL. Simulated gastric fluid (SGF) was prepared according to the 2008 USP vol. 1, p 817 except without pepsin.

TABLE 14

| Potential Salt of (S)-3'-HO-DADFT | Solvent | Approximate Solubility |
|---|---|---|
| calcium | Water | <2 |
| magnesium | Water | ≧48 |
| zinc | Water | <1 |
| potassium | Water | ≧48 |
| potassium | ACN | >6 |
| potassium | EtOAc/H$_2$O | >70 |
| potassium | IPA | >68 |
| potassium | MEK | <7 |
| potassium | THF | ~5 |
| magnesium | SGF | ≧50 |
| potassium | SGF | ≧230 |
| zinc | SGF | ≧39 |

EXAMPLE 12

Attempts to Produce Salts of (S)-4'-(OH)-DADFT-PE

The results of an initial screen of salts of a representative compound, (S)-4'-(OH)-DADFT-PE, are given below in Table 15. The methods could be applied to find salts of any compound of Formula I. The methods employed may produce the following salts: 1-carboxy-4-guanidinobutan-1-aminium (S)-2-(2-hydroxy-4-(2-(2-(2-methoxyethoxy)ethoxy)ethoxy)phenyl)-4-methyl-4,5-dihydrothiazole-4-carboxylate, calcium bis-[(S)-2-(2-hydroxy-4-(2-(2-(2-methoxyethoxy)ethoxy)ethoxy)phenyl)-4-methyl-4,5-dihydrothiazole-4-carboxylate], calcium (S)-2-(2-hydroxy-4-(2-(2-(2-methoxyethoxy)ethoxy)ethoxy)phenyl)-4-methyl-4,5-dihydrothiazole-4-carboxylate hydroxide, choline (S)-2-(2-hydroxy-4-(2-(2-(2-methoxyethoxy)ethoxy)ethoxy)phenyl)-4-methyl-4,5-dihydrothiazole-4-carboxylate, 2,6-diammoniohexanoate (S)-2-(2-hydroxy-4-(2-(2-(2-methoxyethoxy)ethoxy)ethoxy)phenyl)-4-methyl-4,5-dihydrothiazole-4-carboxylate, 2-hydroxyethanaminium (S)-2-(2-hydroxy-4-(2-(2-(2-methoxyethoxy)ethoxy)ethoxy)phenyl)-4-methyl-4,5-dihydrothiazole-4-carboxylate, 2-aminoethanaminium (S)-2-(2-hydroxy-4-(2-(2-(2-methoxyethoxy)ethoxy)ethoxy)phenyl)-4-methyl-4,5-dihydrothiazole-4-carboxylate, 2-ammonio-3-(1H-imidazol-3-ium-4-yl)propanoate (S)-2-(2-hydroxy-4-(2-(2-(2-methoxyethoxy)ethoxy)ethoxy)phenyl)-4-methyl-4,5-dihydrothiazole-4-carboxylate, 4-(2-hydroxyethyl)morpholin-4-ium (S)-2-(2-hydroxy-4-(2-(2-(2-methoxyethoxy)ethoxy)ethoxy)phenyl)-4-methyl-4,5-dihydrothiazole-4-carboxylate, 1-(2-hydroxyethyl)pyrrolidinium (S)-2-(2-hydroxy-4-(2-(2-(2-methoxyethoxy)ethoxy)ethoxy)phenyl)-4-methyl-4,5-dihydrothiazole-4-carboxylate, 1-(2-hydroxyethyl)piperidinium (S)-2-(2-hydroxy-4-(2-(2-(2-methoxyethoxy)ethoxy)ethoxy)phenyl)-4-methyl-4,5-dihydrothiazole-4-carboxylate, magnesium bis-[(S)-2-(2-hydroxy-4-(2-(2-(2-methoxyethoxy)ethoxy)ethoxy)phenyl)-4-methyl-4,5-dihydrothiazole-4-carboxylate], magnesium (S)-2-(2-hydroxy-4-(2-(2-(2-methoxyethoxy)ethoxy)ethoxy)phenyl)-4-methyl-4,5-dihydrothiazole-4-carboxylate hydroxide, 2,3,4,5,6-pentahydroxy-N-methylhexan-1-aminium (S)-2-(2-hydroxy-4-(2-(2-(2-methoxyethoxy)ethoxy)ethoxy)phenyl)-4-methyl-4,5-dihydrothiazole-4-carboxylate, piperazin-1-ium (S)-2-(2-hydroxy-4-(2-(2-(2-methoxyethoxy)ethoxy)ethoxy)phenyl)-4-methyl-4,5-dihydrothiazole-4-carboxylate, potassium (S)-2-(2-hydroxy-4-(2-(2-(2-methoxyethoxy)ethoxy)ethoxy)phenyl)-4-methyl-4,5-dihydrothiazole-4-carboxylate, potassium (S)-2-(2-hydroxy-4-(2-(2-(2-methoxyethoxy)ethoxy)ethoxy)phenyl)-4-methyl-4,5-dihydrothiazole-4-carboxylate 2-ethylhexanoic acid, sodium (S)-2-(2-hydroxy-4-(2-(2-(2-methoxyethoxy)ethoxy)ethoxy)phenyl)-4-methyl-4,5-dihydrothiazole-4-carboxylate 2-ethylhexanoic acid, sodium (S)-2-(2-hydroxy-4-(2-(2-(2-methoxyethoxy)ethoxy)ethoxy)phenyl)-4-methyl-4,5-dihydrothiazole-4-carboxylate acetic acid, sodium (S)-2-(2-hydroxy-4-(2-(2-(2-methoxyethoxy)ethoxy)ethoxy)phenyl)-4-methyl-4,5-dihydrothiazole-4-carboxylate, 1,3-dihydroxy-2-(hydroxymethyl)propan-2-aminium (S)-2-(2-hydroxy-4-(2-(2-(2-methoxyethoxy)ethoxy)ethoxy)phenyl)-4-methyl-4,5-dihydrothiazole-4-carboxylate, (S)-4-carboxy-2-(2-hydroxy-4-(2-(2-(2-methoxyethoxy)ethoxy)ethoxy)phenyl)-4-methyl-4,5-dihydrothiazol-3-ium 2-sulfoethanesulfonate, (S)-4-carboxy-2-(2-hydroxy-4-(2-(2-(2-methoxyethoxy)ethoxy)ethoxy)phenyl)-4-methyl-4,5-dihydrothiazol-3-ium hydrochloride, (S)-4-carboxy-2-(2-hydroxy-4-(2-(2-(2-methoxyethoxy)ethoxy)ethoxy)phenyl)-4-methyl-4,5-dihydrothiazol-3-ium hydrogen sulfate, (S)-4-carboxy-2-(2-hydroxy-4-(2-(2-(2-methoxyethoxy)ethoxy)ethoxy)phenyl)-4-methyl-4,5-dihydrothiazol-3-ium methanesulfonate, and (S)-4-carboxy-2-(2-hydroxy-4-(2-(2-(2-methoxyethoxy)ethoxy)ethoxy)phenyl)-4,5-dihydrothiazol-3-ium4-methylbenzenesulfonate.

TABLE 15

| Base (Base:API) | Conditions | Observations | XRPD Results |
|---|---|---|---|
| L-arginine (1:1) | Added base to API in TFE (few particles). Addition of TFE (clear), addition of heptane (immiscible). RE, RT to ~40° C. | Yellow film | — |
| | From above, added IPA, sonicated, VF (sticky solids), stored over P2O5 | Unknown morphology, opaque aggregates, some b/e on few particles | Arginine A (1 small low angle peak + halo) |

TABLE 15-continued

| Base (Base:API) | Conditions | Observations | XRPD Results |
|---|---|---|---|
| Ca(OH)$_2$ (1:1) | Added base to API in EtOH (solid present), added water, sonicated for ~10 min (viscous material), added EtOH at ~55° C. (hazy solution, solids present), added water, heated to ~70° C., added EtOH (slightly hazy few particles), hot filtered (hazy solution), SC attempt from ~70° C. to RT | NS | — |
| | From above, FPE attempt (clear), RE, ~60° C. (thin film) | Unknown morphology, no b/e | Calcium B |
| Ca(OH)$_2$ (2:1) | API in ACN:water (4:1), added solid base (solids), sonicated (flocculated solids). Slurry, ~37° C., overnight (flocculated solids), VF (damp small spherical particles), VO, ~54° C. | Unknown morphology, opaque aggregates, no b/e | Calcium A + Ca(OH)2 |
| | Filtrate from above, RE, ~55 to ~80° C. | Film | — |
| | Solids from above, prior VO Added MTBE. Agitation, RT, ~1 day (small droplets, white suspension) followed by VF | Unknown morphology, opaque flakes and aggregates, no b/e | Calcium A + Ca(OH)2 |
| Choline hydroxide (1:1) | Added base in IPA:water (1:1.3) to API in IPA at ~60° C. (slightly hazy). FC attempt from ~60° C. to RT | Hazy, NS | — |
| | From above, VD with IPE (oily material), sonicated and triturated (cloudy, oily material), kept at RT. FPE attempt (clear), added water (hazy), kept at RT (hazy), RE, RT, ~30 min followed by RE, ~60° C. | Sticky material | — |
| | From immediately above, added MeOH, sonicated (clear), added EtOAc with final 1:2 ratio, SE | Oily material | — |
| L-Lysine (1:1) | Added aqueous base to API in EtOH (clear), kept in refrigerator | NS | — |
| | From above, FE | Sticky material | — |
| | From above, Added IPA, sonicated (hazy, sticky gel), heated to ~65° C. (hazy, sticky gel), added IPA (cloudy), VF (few solids), stored over P$_2$O$_5$ | Unknown morphology, no b/e | Lysine A (disordered) |
| Ethanol-amine (1:1) | API in chloroform, added base in chloroform (clear), SE (sticky gel), triturated, SE (oily gel), added EtOAc, triturated. Agitated, RT, ~2 days | Small oily droplets in yellow solution | — |
| | From above, RT | Sticky material | — |
| EDA (1:1) | API in acetone, added base in acetone. SE (sticky gel), triturated, SE (oily gel), added MTBE, triturated. Agitated, RT, ~2 days | Brown oily mass in dark yellow solution | — |
| | From above, solvent decanted, blew N2 | Oily mass | — |
| L-Histidine (1:1) | Added base to API in EtOAc (solids). Slurry a, ~40° C., ~2 days (solids). Heated to ~60° C., added TFE (solids), kept at RT. Added water (solids), heated to ~60° C. (solids), added water (clear), SC (emulsion, no solids). RE, RT, ~30 min (solvent present), RE, ~55° C. | Sticky material | — |
| | From above, added EtOH, sonicated (Ppt), VF | Unknown morphology, opaque aggregates, some b/e on few particles | L-Histidine + peak |

TABLE 15-continued

| Base (Base:API) | Conditions | Observations | XRPD Results |
|---|---|---|---|
| 4-(2-Hydroxy-ethyl morpholine) (~1:1) | Added base to API in EtOH (clear). Stirring, ~4 hr (clear), added heptane (hazy solution). Kept in refrigerator, ~1 day (hazy solution). RE, ~60° C. | Sticky material | — |
| | From above, added THF, sonicated (clear) added heptane (cloudy, oily material). Kept at RT, ~5 days. RE, ~60° C. | Sticky material | — |
| | From immediately above, added EtOAc, sonicated (hazy), triturated (few fine solids), FE | Sticky material | — |
| | From immediately above, added MeOH:water (6:1) (hazy solution). Agitation, RT, ~4 days (clear). Added water, sonicated. Kept at RT, ~1 day (hazy). RE, ~55° C. | Sticky material | — |
| | From immediately above, added IPA, sonicated (cloudy), added more IPA, sonicated (slightly hazy), triturated (slightly hazy). Stirring, RT, ~4 days | Clear solution, NS | — |
| | From immediately above, SE with stirring, RT | Oily material | — |
| 1-(2-Hydroxy-ethyl pyrrolidine) (~1:1) | Added base to API in EtOH at ~60° C. (clear), SC attempt from ~60° C. to RT | NS | — |
| | From above, FE | Sticky material | — |
| | From immediately above, added chloroform, sonicated (clear), added IPE (hazy). Kept at RT, ~2 h (oily material), decanted solvent, added chloroform, sonicated (clear), added decanted solvent (cloudy). Kept in refrigerator, ~15 min, kept in freezer, ~2 days (oily material). RE, ~60° C. | Sticky material | — |
| | From immediately above, added MeOH, sonicated (clear), added EtOAc (clear), kept at RT (few solids, cloudy), FE, added EtOAc, triturated (few fine solids), kept at RT, ~4 days (few fine solids), SE | Oily material | — |
| | From immediately above, added ACN:water (4:1), sonicated (slightly hazy), added more ACN:water (4:1), sonicated (slightly hazy). Agitation, RT, ~11 days (clear). RE, ~65° C. | Oily material | — |
| | Added base to API in EtOAc (clear). Stirring, ~1 hr (clear), VD from EtOAc/IPE (oily material), sonicated and triturated (cloudy, oily material), kept at RT, solvent pipetted off, blew N2 (sticky material), kept at RT, added MTBE, triturated | Hazy, oily material | — |
| | From immediately above, (oily, solvent droplets), blew N2 | Sticky material | — |
| | From immediately above, added IPA, sonicated (NS, some fibers). Agitation, RT, ~4 days | Clear solution, NS | — |
| | From immediately above, SE with stirring, RT, ~1 day | Oily material | — |
| 1-(2-Hydroxy-ethyl)-piperidine (1:1) | Added base to API in EtOAc (clear). Stirring, RT, ~1 hr. VD from EtOAc/IPE (oily material), sonicated, triturated | Slightly hazy, oily material, oily mass | — |
| | From above, decanted solvent, added acetone, sonicated (clear), SE | Oily material | — |
| | From immediately above, added MeOH, sonicated (slightly hazy), added EtOAc, sonicated (hazy, oily droplets, immiscible layer). SE | Oily material | — |

TABLE 15-continued

| Base (Base:API) | Conditions | Observations | XRPD Results |
|---|---|---|---|
| | with stirring (few sticky solids on the wall, clear solution), FPE attempt (reduced solvent, sticky solids), RE, ~65° C. | | |
| Mg(OH)$_2$ (1:1) | Added base to API in EtOH (hazy solution, solids present), added water (hazy solution, solids present), sonicated for ~10 min (hazy solution, fine solids present), VF (no solids), filtrate collected, added water to filtrate (hazy solution, few fine particles) | NS | — |
| | From above, FPE attempt (clear). RE, ~60° C. | Sticky material | — |
| | From immediately above, added IPA (cloudy, solids), added IPE (cloudy, solids). Kept in freezer, ~2 days (solids), VF, blew N2 (solids) | Unknown morphology, no b/e | Magnesium A (1 low angle peak) |
| Mg(OH)$_2$ (2:1) | API in ACN:water (4:1), added base (solids), sonicated (solids). Slurry, ~37° C., overnight (solids), VF solids off | — | — |
| | Filtrate from above RE, ~55 to ~80° C. | Tacky solids and powder. Unknown morphology, red aggregates, some b/e on few particles | Magnesium A (1 low angle peak) |
| NMG (1:1) | Added API in EtOH to base, sonicated (clear). SE (no solvent, sticky material), blew N2 | Sticky material | — |
| | From above, added MeOH, sonicated (clear), added EtOAc (some precipitation). Slurry, ~5.5 hrs (viscous material), washed with EtOAc,VF | Unknown morphology, opaque aggregates, no b/e | NMG A |
| | Added API in IPA to aqueous base (clear), added IPA (clear). Agitation, RT, ~5 days (clear) followed by FE (solids, thin film | Unknown morphology, opaque aggregates, some b/e on few particles a | — |
| Piperazine (1:1) | Added API in EtOH to base (viscous material), shook vial (small pieces of viscous material). Stirring, RT, ~1 hr (clear) followed by FE | Unknown morphology, some b/e | Piperazine A |
| | Added base to API in TFE (clear), addition of toluene (clear), sonicated (clear), RE, RT | Sticky film | — |
| | From above, dissolved film in EtOAc, VD from EtOAc/DEE, ~5 hrs (white solids and orange oily residue), sonicated and triturated (some oily residue remained). Slurry, ~37° C., ~1 day, triturated (orange oily residue persists), VF (white solids deliquesced), stored over P2O5 (orange sticky material), blew N2 (slightly tacky solids), placed back into P2O5 | Unknown morphology, opaque aggregates, some b/e on few particles | Piperazine A |
| KOH (~1:1) | Added aqueous base to API in EtOH (clear), added water (clear solution). Kept at RT, ~1 day (no solids). RE, ~50° C. | Sticky material | — |
| | From above, added acetone, sonicated (few solids), heated to ~50° C. (few solids), added IPE (cloudy). Kept at RT, ~5 days (oily material), sonicated, triturated (hazy solution, oily material), kept at RT (clear solution, oily material), solvent decanted. VO, ~55° C., ~2 days | Sticky material | — |

TABLE 15-continued

| Base (Base:API) | Conditions | Observations | XRPD Results |
|---|---|---|---|
| | API in chloroform, added methanolic base, added hexanes (cloudy). RE, RT | Sticky yellow material | — |
| | From immediately above, dissolved material in EtOAc, sonicated (clear). VD from EtOAc/DEE, ~5 hrs, triturate oily solids, left standing capped | Clear solution, oily material | — |
| | Dissolved API at ~75° C. in EtOAc, added methanolic base (clear). FC to RT (clear), sonicated (clear). VD from EtOAc/IPE, ~4 days (oil), triturated, kept at RT, ~1 day (gel), decanted solvent, blew N2 (sticky). VO, ~54° C., ~2 days | Sticky oil | — |
| | From immediately above, added MeOH, sonicated (clear), added water (clear) with final 4:1 ratio. Stirring, RT, ~3 days (clear, no solids) followed by SE | Oily material | — |
| | Added methanolic base to API, added methanol (clear), sonicated (clear). VD with IPE, ~4 days (oil), triturated, kept at RT, ~1 day (gel), decanted solvent, blew N2 (sticky). VO, ~54° C., ~2 days | Sticky oil | — |
| | From immediately above, added EtOH, sonicated (clear), added MTBE (clear) with final 4:1 ratio. Stirring, RT, ~3 days (clear, no solid) followed by SE | Oily material | — |
| Potassium 2-ethyl-hexanoate (1:1) | Added triethylamine to API in IPA (clear), added base in 1-BuOH:DCM (1:1) (clear). Stirring, RT, overnight (clear), added IPE (cloudy). Agitation, RT, ~3 days | Clear solution | — |
| | From above, added IPA at ~60° C., (small amount of oily material), added IPA (clear), SC from ~60° C. to RT (hazy). Kept at RT (clear), added IPE (cloudy, fine solids), kept at RT (clear, oily material), added heptane (slightly hazy). RE, ~60° C. (sticky material), added EtOAc, triturated | Yellow clear solution, NS | — |
| NaOAc (1:1) | Added aqueous base to API in EtOH (clear solution). Kept in refrigerator, ~4 days | NS | — |
| | From above, FE | Sticky material | — |
| | From immediately above, added THF, sonicated (hazy), heated to ~60° C. (hazy), added heptane (tacky solids), decanted solvent, added THF (slightly hazy), added decanted solvent (cloudy). Kept in refrigerator, ~15 min, kept in freezer, ~2 days (sticky material). RE, ~60° C. | Sticky material | — |
| | From above, added EtOAc, triturated, sonicated (slightly hazy), kept at RT (few solids, cloudy). FE | Unknown morphology, no b/e | Sodium A (1 small peak) |
| Sodium 2-Ethyl-hexanoate (1:1) | Added triethylamine to API in IPA (clear), added base in 1-BuOH:DCM (1:1) (hazy). Stirring, RT, ~2.5 hrs (hazy) followed by IPE addition (cloudy), kept in freezer, ~4 days | Sticky material | — |
| NaOH (~1:1) | Added aqueous base to API in EtOH (clear), added water (no solids). RE, ~55° C. | Sticky material | — |
| | From above, added EtOAc, sonicated (hazy solution, solids), heated to ~60° C. (solids), VF (very few solids), filtrate collected, SE | Sticky material | — |

TABLE 15-continued

| Base (Base:API) | Conditions | Observations | XRPD Results |
|---|---|---|---|
| | API in acetone, added methanolic base (clear), sonicated (clear), added IPE, sonicated (oily aggregates), decanted solution, redissolved oily aggregates in acetone at ~60° C. (clear), added warm decanted solution (cloudy), CCS (dry ice/acetone) from ~60° C. (cloudy). Kept in freezer | Hazy, sticky material | — |
| | API in ACN at ~45° C. Addition of methanolic base followed by FC attempt (clear). ACN and water added in final 9:1 ratio at ~45° C., FC attempt from ~45° C. to RT | Clear yellow-brown solution, NS | — |
| | Base in MeOH. Addition to API, sonicated (clear). Addition of IPE (oily substance). RE, RT (oil) followed by VD from MeOH/DEE | NS | — |
| | API in chloroform, added methanolic base (clear), added IPE (cloudy), sonicated (oily aggregates). VF, blew N2, stored solids over P2O5 | Unknown morphology, opaque aggregates, no b/e | Sodium A (NP) |
| | API in IPA, added methanolic base (hazy solution, few solids), heated to ~60° C., added API in IPA (clear), SC attempt from ~60° C. to RT | — | — |
| | From immediately above, (oily material), blew N2 | Sticky material | — |
| | API in IPA, added methanolic base (hazy solution, few solids), heated to ~60° C., added API in IPA (clear), SC attempt from ~60° C. to RT. Added MeOH:water (7:3) (clear). Stirring, RT, overnight | Clear | — |
| Tromethamine (1:1) | Added API in EtOH to base, (solids present). Stirring, RT, ~3 hr, (clear) followed by FE | Unknown morphology, some b/e | Tromethamine A |
| 1,2-EDSA (1:1) | Added API in EtOH to ethanolic (clear solution), sonicated, (clear solution). Stirring, RT, overnight (clear). Added heptane (hazy, oily mass), sonicated (hazy, oily mass). RE, ~65° C. | Oily material | — |
| | From above, added EtOAc, sonicated, triturated (clear solution, oily mass). Stirring, RT, ~7 days (clear solution) | Oily material | — |
| | From above, added MeOH:water (6:1), sonicated (clear solution). RE, ~60° C., ~20 min (oily material), etched oily material, RE, RT (sticky material). Stored over P2O5 | Thin film, viscous material | — |
| | Added API in acetone to acid in acetone (cloudy, oily mass). Stirring, RT, ~30 min (oily mass, clear) followed by SE, RT | Oily material | — |
| | From immediately above, added MeOH, sonicated (clear solution). SE, RT (oily material), added EtOAc sonicated, triturated (clear solution, oily mass). Stirring, RT, ~5 days (oily material, small amount of solvent). Added MeOH, sonicated (oily material dissolved). RE, ~60° C., ~20 min (oily material), etched. RE, RT, ~15 min | Viscous material | — |
| | From immediately above, added MTBE, sonicated, triturated (clear solution, viscous material), added acetone, sonicated (hazy solution). RE, ~60° C. | Oily material | — |

TABLE 15-continued

| Base (Base:API) | Conditions | Observations | XRPD Results |
|---|---|---|---|
| HCl (1:1) | Added aqueous acid to API in EtOH (clear solution). Agitation, ~2 hrs (clear solution). Heptane addition (oily mass, immiscible layers) followed by RE, ~65° C. | Oily material | — |
| | From above, added EtOAc, sonicated, triturated (oily mass, hazy solution). Stirring, RT, ~7 days (clear solution, oily material). RE, ~60° C. (oily material), etched oily material, RE at RT (tacky solids), stored over P2O5 | Glassy flakes, unknown morphology, no b/ea | — |
| | Added acid to API in acetone (clear solution), sonicated (clear solution. SE, RT | Oily material | — |
| | From above, added IPA, sonicated, triturated, (clear, small amount of oily material). Stirring, RT, ~5 days (clear solution). RE, ~60° C., ~20 min (oily material), etched oily material, RE, RT, ~20 min (sticky solids), stored over P2O5 | Glassy flakes, unknown morphology, no b/eb | HCl A |
| H2SO4 (1:1) | Added aqueous acid to API in EtOH (clear solution). Agitation, RT, ~2 hrs (clear solution). Heptane addition (oily mass in hazy solution) followed by RE, ~65° C. | Oily mass | — |
| | From above, added EtOAc, sonicated, triturated (oily mass, hazy solution), added more EtOAc (oily mass, hazy solution). Stirring, RT, ~7 days (hazy solution, oily material) followed by RE, ~65° C. | Oily material | — |
| | Added acid to API in acetone (clear solution), sonicated (clear solution). SE, RT | Oily material | — |
| | From above, added IPE, sonicated, triturated (hazy, oily mass). Stirring, RT, ~5 days (clear solution, oily material). RE, RT (oily material) followed by VO, RT, ~1 day | Viscous material | — |
| MSA (1:1) | Added ethanolic acid to API in EtOH (clear solution), sonicated (clear solution). Stirring, ~2.5 hrs (clear) followed by RE, ~65° C. (oily). Added EtOH, sonicated (clear), added heptane (hazy). RE, ~65° C. | Oily material | — |
| | Added acid in acetone to API in acetone (clear solution). SE, RT | Oily material | — |
| | From above, added DEE, sonicated, triturated (hazy solution, oily material). Stirring RT for ~2 days (oily material), added MeOH, sonicated (hazy solution), RE at ~60° C. for ~20 min. (oily material), etched oily material. RE, RT | Oily material | — |
| p-TSA mono- hydrate (1:1) | Added API in EtOH to ethanolic acid, sonicated (clear solution). Stirring, ~1.5 hrs (clear solution). Added heptane (hazy, oily mass), sonicated (hazy, oily mass). RE, ~65° C. | Oily material | — |
| | From above, added EtOAc, sonicated, triturated (oily mass hazy solution). Stirring, RT, ~2 days (hazy solution, oily mass) followed by RE, ~65° C. | Oily mass | — |
| | Added API in acetone to acid in acetone (clear solution). Stirring, RT, ~0.5 hrs (clear solution) followed by SE, RT | Oily material | — |

TABLE 15-continued

| Base (Base:API) | Conditions | Observations | XRPD Results |
|---|---|---|---|
| | From above, added MeOH:IPE (1:9), sonicated, triturated (hazy, oily material). Stirring, RT (oily mass, clear). Added more IPE sonicated, triturated (hazy, oily material). Stirring, RT, ~4 days (clear solution, oily material). Added MeOH, sonciated (hazy solution, oily droplets). RE, RT, ~20 min (oily material), RE at ~60° C. for ~15 min. (sticky material), stored over P2O5 | Viscous material | — |

EXAMPLE 13

Calcium Salt of (S)-4'-(OH)-DADFT-PE

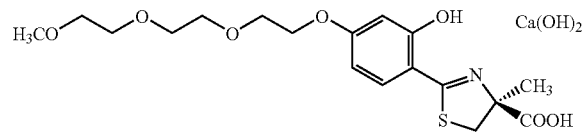

The API was dissolved in ACN:water (4:1), solid base was added, the suspension was sonicated overnight at 37° C. The solids were collected via vacuum filtration and dried in a vacuum oven. The calcium salt is consistent with disordered material with a higher level of order compared to magnesium salt candidate. The material, designated as Calcium A, showed negligible aqueous solubility. No apparent deliquescence was observed upon ~75% RH stress.

XRPD data for the calcium salt exhibited two low angle peaks suggesting a higher level of order compared to magnesium salt candidate (FIG. 13). The salt candidate was prepared utilizing a 1:1 ratio of calcium hydroxide to 4'-(OH)-DADFT-PE. Solution $^1$H NMR data for the potential salt were not acquired due to its low solubility in organic solvents.

EXAMPLE 14

Lysine Salt of (S)-4'-(OH)-DADFT-PE

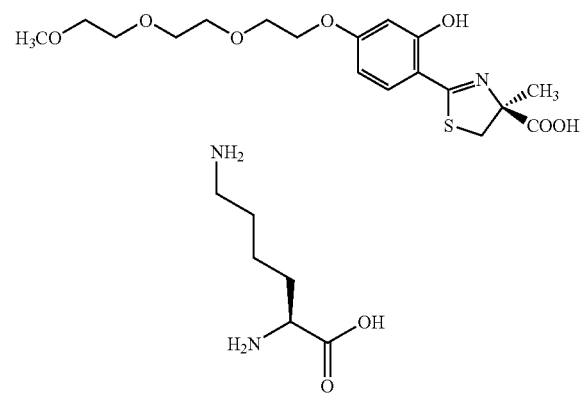

Aqueous base was added to the API in EtOH forming a clear solution, which was kept in a refrigerator. Following fast evaporation, isopropyl alcohol was added, followed by sonication, yielding a hazy, sticky gel. The material was heated to ~65° C. and isopropyl alcohol was added. Vacuum filtration yielded solids which were stored over $P_2O_5$. Lysine salt candidate is consistent with crystalline somewhat disordered lysine salt of 4'-(OH)-DADFT-PE with ~1:1 ratio of lysine to API. The material showed negligible aqueous solubility. No apparent deliquescence was observed upon ~75% relative humidity stress however the salt became oily suggesting its hygroscopicity.

The lysine salt candidate was characterized by XRPD and solution $^1$H NMR spectroscopy. Overall, the data for the material are consistent with crystalline, somewhat disordered lysine salt of 4'-(OH)-DADFT-PE with ~1:1 ratio of lysine to API. XRPD pattern exhibited resolution of peaks indicative of crystalline material with some disorder consistent with Lysine A salt of 4'-(OH)-DADFT-PE (FIG. 13).

Solution $^1$H-NMR data are consistent with lysine salt of 4'-(OH)-DADFT-PE based on peak centered at ~8.0 ppm, peaks at ~3.2 ppm and ~2.7 ppm and in the range of ~1.8-1.3 ppm attributable to lysine. The integral values suggest that the salt contains approximately one mole of lysine per one mole of 4'-(OH)-DADFT-PE. Peak at ~2.50 ppm is associated with partially deuterated DMSO.

EXAMPLE 15

Magnesium Salt of (S)-4'-(OH)-DADFT-PE

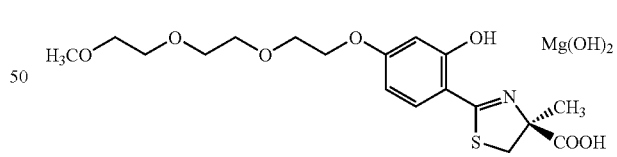

The API was dissolved in ACN:water (4:1), solid base was added, the resulting slurry was sonicated overnight at 37° C. Solids were collected via vacuum filtration, and the filtrate was reduced via rotary evaporation between ~55 and ~80° C. The resulting magnesium salt candidate is consistent with amorphous or mesophasic monohydrate of 4'-(OH)-DADFT-PE salt. The material exhibited substantial aqueous solubility (~60 mg/mL). No apparent deliquescence was observed upon ~75% RH stress however the salt showed a significant water uptake (~42.7 wt %) upon increasing relative humidity from ~5% to ~95% RH suggesting its hygroscopicity.

The magnesium salt candidate was prepared using a 1:1 ratio of magnesium hydroxide to 4'-(OH)-DADFT-PE. It was characterized by XRPD, thermogravimetry (TG), differential scanning calorimetry (DSC), moisture sorption analysis and ¹H NMR spectroscopy. Overall, the data for the material are consistent with amorphous or mesophasic salt of 4'-(OH)-DADFT-PE possibly hydrated or containing water. The salt showed a significant water uptake (~42.7 wt %) upon increasing relative humidity from ~5% to ~95% RH suggesting its hygroscopicity.

XRPD data demonstrated a disordered pattern consistent with Magnesium A salt. The pattern exhibited single low angle peak suggesting amorphous or mesophasic material.

Solution ¹H NMR data are consistent with formation of 4'-(OH)-DADFT-PE salt based on significant changes throughout the spectrum. Considerable peak shifts were observed in ~8-6 ppm, ~4.2-3.0 ppm, and ~1.6-1.3 ppm ranges while no peaks were detected in ~14-12 ppm range compared to free 4'-(OH)-DADFT-PE. Additional small peaks (~6.6 ppm, ~2.3 ppm, ~1.9 ppm and ~1.6-1.5 ppm.) were observed, likely due to unidentified impurities. The spectrum also exhibited peak at ~3.34 ppm associated with water. Peak at ~2.50 ppm is associated with partially deuterated DMSO. Small peak at ~2.54 ppm was observed due to undeuterated DMSO.

Thermal data are consistent with solvated material or the material containing solvent. TG data demonstrated a ~4.0% weight loss between ~36 and ~137° C. The weight loss is likely attributable to a loss of approximately 1 mole of water per mole of API based on the preparation conditions and ¹H NMR data. The ¹H NMR spectrum of the material prepared in ethanol:water (1:1) mixture did not exhibit peaks associated with ethanol, while peak attributable to water was detected. A smaller ~1.6% loss between ~137° C. and ~195° C. followed by a sharp weight loss at ~280° C. (onset) were observed likely due to decomposition.

Figure 15:
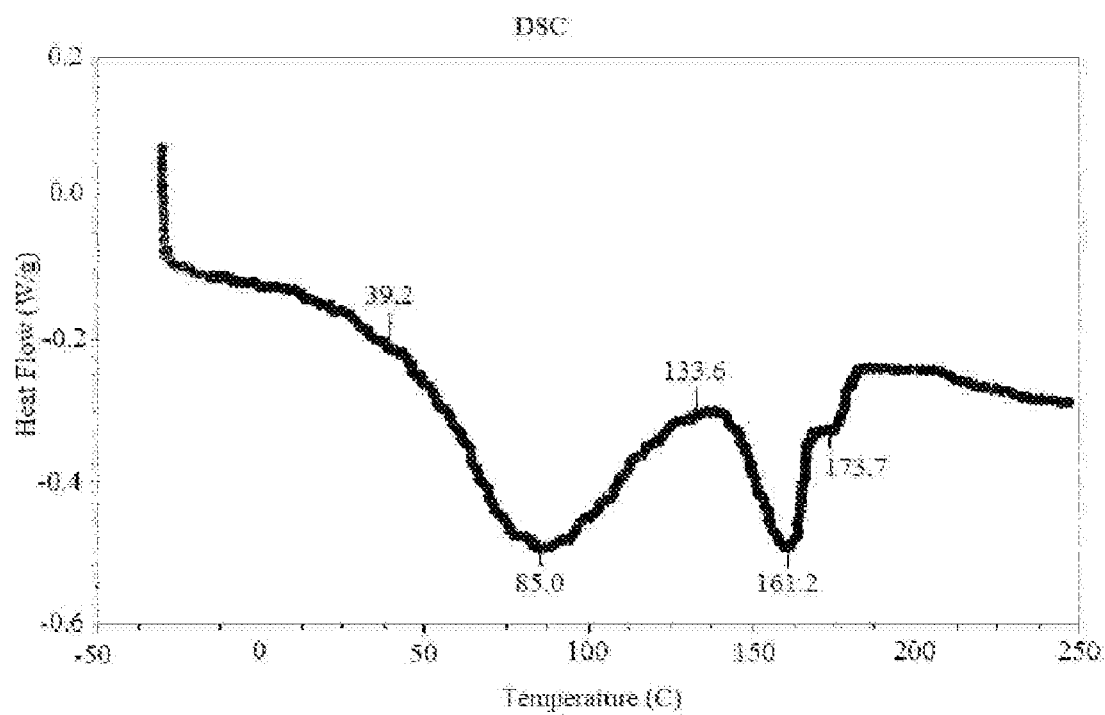
FIG. 15. DSC spectrum of (S)-4'-(OH)-DADFT-PE magnesium salt.
Figure 16:
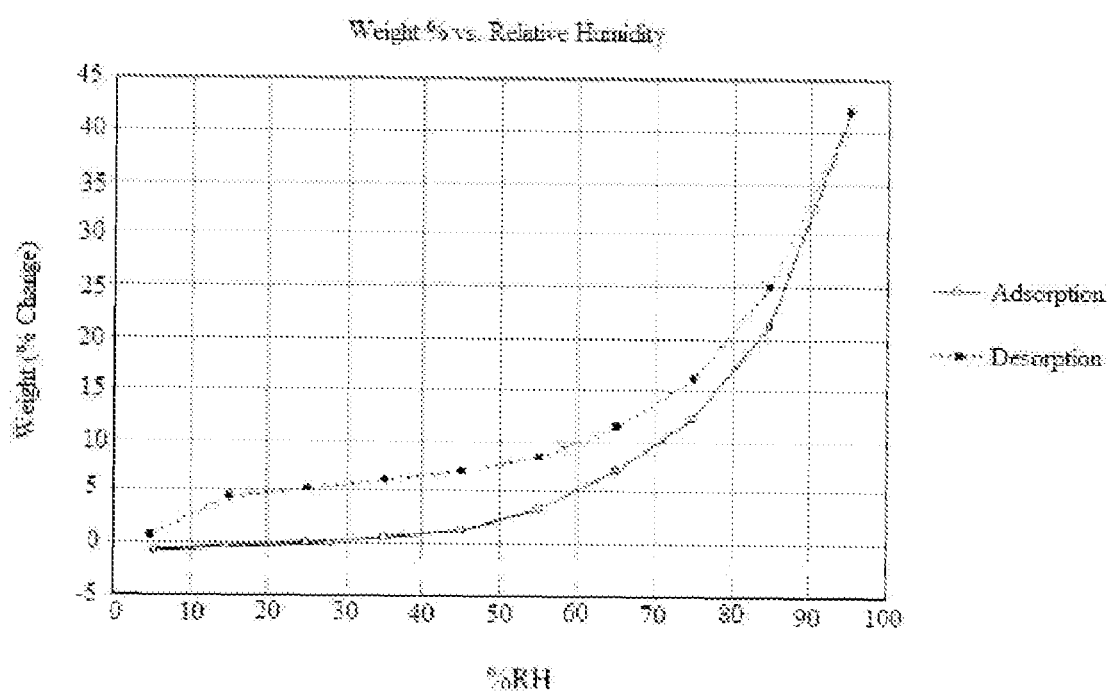
FIG. 16. Dynamic vapor sorption/desorption isotherm of (S)-4'-(OH)-DADFT-PE magnesium salt.

The differential scanning calorimetry (DSC) curve demonstrated a broad endotherm between ~39.2° C. and ~133.6° C. with a peak maximum at ~85.0° C. The event was observed concurrently with the ~4.0% TG loss and is likely associated with desolvation. Broadened endotherm at ~161.2° C. followed by a small endothermic event at ~173.7° C. (peak maxima) was detected possibly due to melting accompanied by decomposition of the material (FIG. 15).

Moisture sorption data showed ~0.7 wt % loss upon equilibration at ~5% RH. A significant ~22.0 wt % gain was observed below ~85% RH, above which the material gained additional ~20.2 wt % with a total gain of ~42.7 wt %. The equilibration was not reached between ~85% and ~95% RH indicating that even higher moisture uptake is possible. Partial desorption occurred with a small hysteresis upon decreasing relative humidity to ~5% (~41.2 wt % loss between ~95% and ~5% RH).

EXAMPLE 16

N-methyl-D-glucamine (NMG) Salt of (S)-4'-(OH)-DADFT-PE

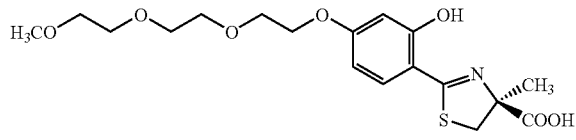

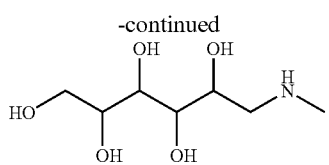

An ethanolic solution of the API was added to the base, then sonicated giving a clear solution. Slow evaporation yielded a sticky material, which was dried by blowing N₂(g) across it. MeOH was added. Following sonication, the addition of EtOAc yielded some precipitation. Slurry for ~5.5 hrs afforded viscous material, which was washed with EtOAc, and isolated via vacuum filtration. NMG salt candidate is consistent with disordered unsolvated NMG salt of 4'-(OH)-DADFT-PE with ~1:1 ratio of NMG to API. The material exhibited substantial aqueous solubility (~60 mg/mL). No apparent deliquescence was observed upon ~75% RH stress however the salt became oily. The salt also showed a significant water uptake (~61.7 wt %) upon increasing relative humidity from ~5% to ~95% RH suggesting its hygroscopicity.

The material contained small amount of free N-methyl-D-glucamine. The salt was characterized by X-ray powder diffraction (XRPD), thermogravimetry (TG), differential scanning calorimetry (DSC), moisture sorption analysis and ¹H NMR spectroscopy. The salt showed a significant water uptake (~61.7 wt %) upon increasing relative humidity from ~5% to ~95% RH suggesting its hygroscopicity.

XRPD patterns exhibited resolution of peaks indicative of a disordered material consistent with NMG A salt of 4'-(OH)-DADFT-PE (FIG. 13). The XRPD pattern of the sample also displayed additional peak associated with free NMG.

¹H-NMR data are consistent with NMG salt of 4'-(OH)-DADFT-PE based on peaks in ~3.9-3.8 ppm and ~3.0-2.8 ppm ranges, peak centered at ~4.7 ppm and peaks at ~3.10 ppm and ~2.48 ppm attributable to NMG. The integral values suggest that the salt contains approximately one mole of N-methyl-D-glucamine per one mole of 4'-(OH)-DADFT-PE. Additional small peak at ~1.9 ppm was observed, likely due to unidentified impurity. Peak at ~2.50 ppm is associated with partially deuterated DMSO.

Figure 17:
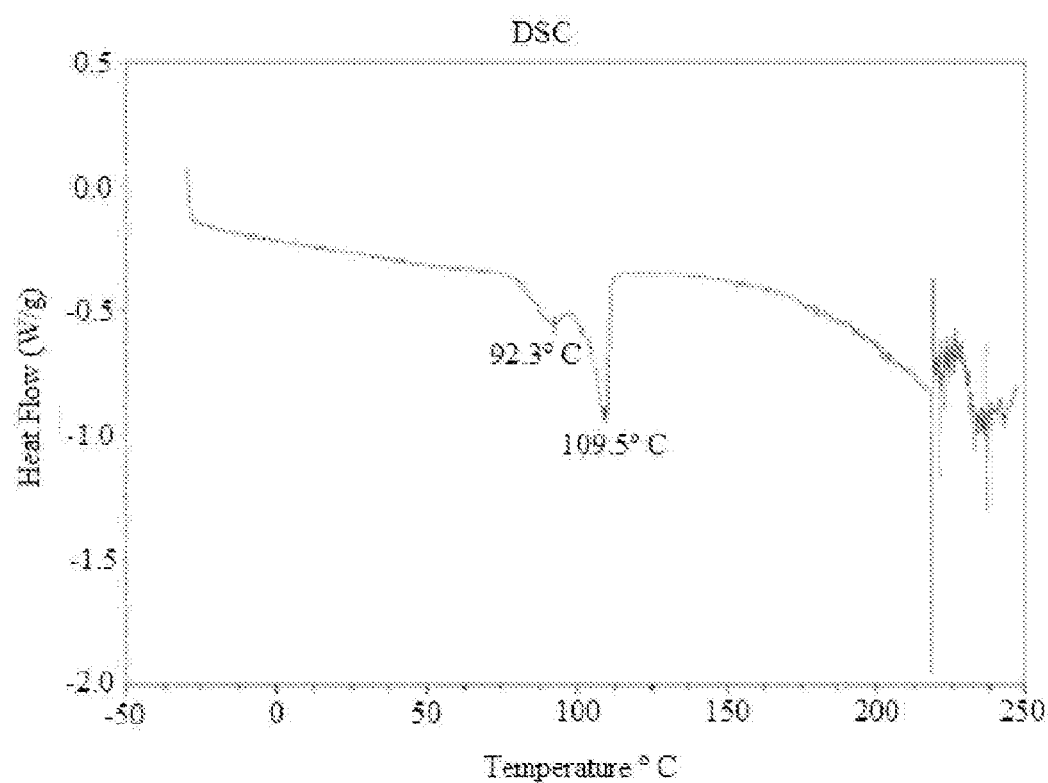
FIG. 17. DSC spectrum of (S)-4'-(OH)-DADFT-PE NMG salt.
Figure 18:
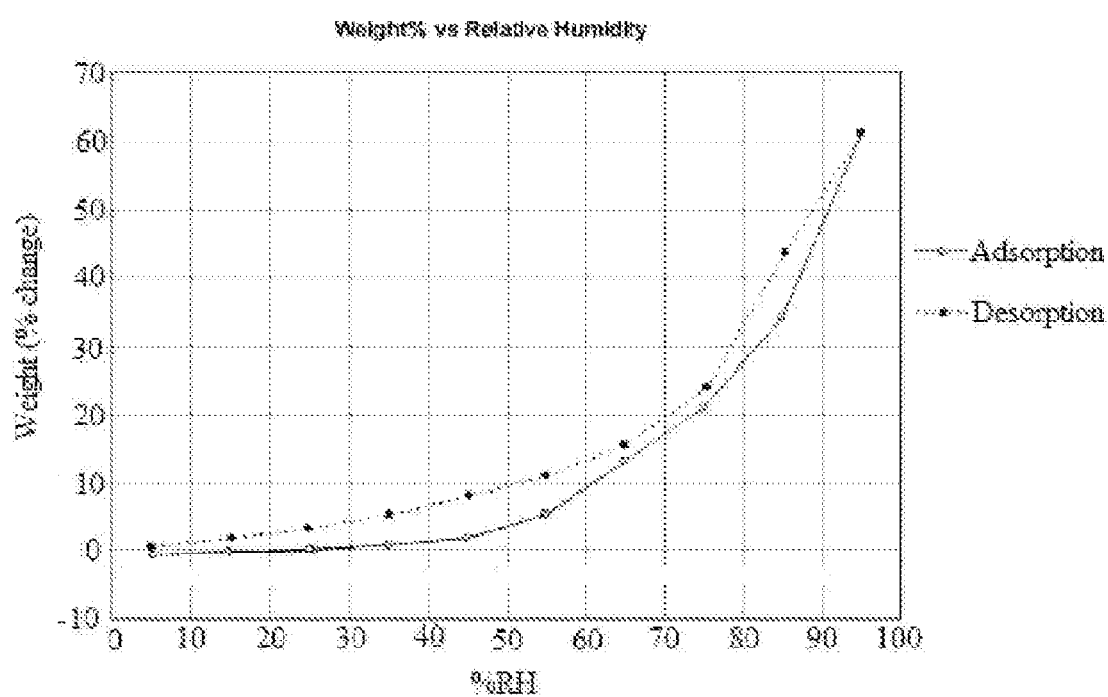
FIG. 18. Dynamic vapor sorption/desorption isotherm of (S)-4'-(OH)-DADFT-PE NMG salt.

Thermal data are consistent with unsolvated material. TG data demonstrated negligible weight loss above ~222° C. Sharp weight loss at ~222° C. (onset) was observed likely due to decomposition. The DSC curve exhibited a small endotherm at ~92.3° C. followed by an endotherm at ~109.5° C. (peak maxima). The two consecutive events could be associated with melting of the salt instantaneously followed by a melting and/or possible recrystallization with melting of free N-methyl-D-glucamine present in the salt. Heat fluctuations beginning at ~180° C. were observed likely due to decomposition (FIG. 17).

Moisture sorption data showed ~0.5 wt % loss upon equilibration at ~5% RH. A significant ~34.7 wt % gain was observed below ~85% RH, above which the material gained additional ~27.0 wt % with a total gain of ~61.7 wt %. The equilibration was not reached between ~65% and ~95% RH indicating that even higher moisture uptake is possible. Partial desorption occurred with a small hysteresis upon decreasing relative humidity to ~5% (~60.6 wt % loss between ~95% and ~5% RH).

EXAMPLE 17

Tromethamine Salt of (S)-4'-(OH)-DADFT-PE

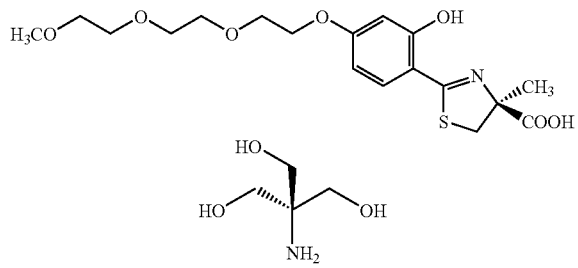

Base was added to an ethanolic solution of the API. A clear solution was obtained by stirring at room temperature for ~3 hr. Fast evaporation of the solution yielded the tromethamine salt of the API. Tromethamine salt candidate is consistent with crystalline unsolvated tromethamine salt of 4'-(OH)-DADFT-PE with ~1:1 ratio of tromethamine to API. The salt exhibited significant aqueous solubility (above ~124 mg/mL) and showed no apparent deliquescence upon ~75% RH stress. The salt showed a small water uptake (~1.5 wt %) below ~65% RH above which it gained ~50.3 wt % indicating lower hygroscopicity compared to magnesium and NMG salt candidates.

The salt was characterized by X-ray powder diffraction (XRPD), thermogravimetry (TG), differential scanning calorimetry (DSC), moisture sorption analysis and $^1$H NMR spectroscopy. XRPD patterns of the two samples exhibited resolution of peaks indicative of crystalline material consistent with Tromethamine A salt of 4'-(OH)-DADFT-PE.

$^1$H-NMR data are consistent with tromethamine salt of 4'-(OH)-DADFT-PE based on additional peak centered at ~3.42 ppm attributable to tromethamine. The integral values suggest that the salt contains approximately one mole of tromethamine per one mole of API. Additional small peak at ~1.9 ppm was observed, likely due to unidentified impurities. The spectrum also exhibited peaks at ~3.33 ppm and ~2.50 ppm attributable to water and partially deuterated DMSO, respectively.

Thermal data are consistent with unsolvated material. The DSC curve demonstrated a sharp asymmetrical endotherm at ~110.1° C. (peak maximum) with a small shoulder prior the endotherm possibly due to melting. Broad endotherm at ~203.5° C. is likely associated with decomposition of the material (FIG. 19).

Moisture sorption data showed a small loss of ~0.7 wt % upon equilibration at ~5% RH. A small ~1.5 wt % gain was observed below ~65% RH, above which the material gained ~50.3 wt % with a total gain of ~51.8 wt %. The equilibration was not reached above ~75% RH indicating that higher moisture uptake is possible. Partial desorption occurred with a small hysteresis upon decreasing relative humidity to ~5% (~48.4 wt % loss between ~95% and ~5% RH).

In the attempt to prepare a hydrated form of tromethamine salt additional experiment was performed. Tromethamine A salt candidate was subjected to a one day relative humidity stress. It was shown to become oily upon ~75% RH stress at elevated temperature. However one hour drying over a desiccant resulted in crystalline material consistent with Tromethamine A salt.

EXAMPLE 18

Solubilities of Salts in Various Solvents

Approximate solubilities are calculated based on the total solvent used to give a solution based on visual inspection. Small aliquots of solvent are added to a weighed sample with agitation. Actual solubilities may be greater because of the volume of the solvent portions utilized or a slow rate of dissolution. Solubilities are reported in Table 16 to the nearest mg/mL.

TABLE 16

| Potential Salt of (S)-4'-OH-DADFT | Solvent | Solubility |
|---|---|---|
| Calcium A | Water | <0.5 |
|  | 0.1 N HCl in Water | 3 |
| Lysine A | Water | <0.5 |
| Magnesium A | Water | 60 |
| NMG A | Water | 60 |
| Tromethamine A | Water | >24 |
|  | Water | >124 |

EXAMPLE 19

Iron Clearing Efficiency of Salts of DADFT Polyethers

*Cebus apella* monkeys were obtained from World Wide Primates (Miami, Fla.). Male Sprague-Dawley rats were procured from Harlan Sprague-Dawley (Indianapolis, Ind.). Ultrapure salts were obtained from Johnson Matthey Electronics (Royston, UK). All hematological and biochemical studies were performed by Antech Diagnostics (Tampa, Fla.).

Cannulation of Bile Duct in Non-Iron-Overloaded Rats. The cannulation has been described previously in Bergeron, R J et al., *Blood* 1993, 81, 2166-2173 and Bergeron, R J et al., *Ann. N.Y Acad. Sci.* 1990, 612, 378-393. Bile samples were collected from male Sprague-Dawley rats (400-450 g) at 3 h intervals for 24 h. The urine sample was taken at 24 h. Sample collection and handling are as previously described. 57'58

Drug Preparation and Administration. In the iron clearing experiments the rats were given a single 50, 150, or 300 mol/kg dose of the drugs po and/or sc. The compounds were administered as a solution in water, 300 mol/kg dose only or (2) as the monosodium salt of the compound of interest (prepared by addition of the free acid to 1 equivalent of NaOH). The chelators were given to the monkeys po and sc at a dose of 150 µmol/kg. The drugs were prepared as for the rats; 2 was given po and sc as a solution in water.

Calculation of Iron Chelator Efficiency. ICE is calculated by dividing the actual amount of iron cleared by a given compound by the theoretical amount that should be cleared. The theoretical iron outputs of the chelators were generated on the basis of a 2:1 ligand:iron complex. The efficiencies in the rats and monkeys were calculated as set forth in Bergeron, R J et al., *J. Med. Chem.* 1999, 42, 2432-2440. Data are presented as the mean+the standard error of the mean; p-values were generated via a one-tailed Student's 1-test in which the inequality of variances was assumed; and a p-value of <0.05 was considered significant.

Chelator-Induced Iron Clearance and Iron Clearing Efficiency in Non-Iron-Overloaded Rodents Dose Response Studies. Because there is a limited amount of chelatable iron available in an animal at any given time, the iron clearance, and therefore iron-clearing efficiency of a ligand, is saturable. The key to managing this phenomenon can be found in the ferrokinetics and the dose-response properties of the ligand. In this regard, the dose-response along with the corresponding ferrokinetics of each compound given po were evaluated in the non-iron-overloaded, bile duct-cannulated rodent model. Results are shown below in Table 17.

TABLE 17

| Compound | Number Animals | Dose, μmol/kg | Iron-Clearing Efficiency (%) |
|---|---|---|---|
| Deferitrin | 8 | 300 | 1.1 ± 0.8 |
| Deferitrin | 5 | 150 | 1.5 + 1.7 |
| (S)-4'-HO-DADFT | 5 | 300 | 5.5 ± 1.9 |
| (S)-4'-HO-DADFT | 4 | 150 | 11.2 ± 4.2 |
| (S)-4'-HO-DADFT | 3 | 50 | 21.7 ± 3.5 |
| (S)-3'-HO-DADFT | 4 | 300 | 10.6 + 4.4 |
| (S)-3'-HO-DADFT | 4 | 150 | 18.7 ± 2.9 |
| (S)-3'-HO-DADFT | 3 | 50 | 20.7 ± 4.4 |

Iron-Clearing Efficiency in Non-Iron-Overloaded Rodents and Iron-Loaded Primates: Oral versus Subcutaneous Administration. A similar protocol was carried out to confirm consistence of results and compare the effects of the compounds across species. *Cebus apella* monkeys and male Sprague-Dawley rats were used, 3-8 per group. Results are shown below in Table 18.

TABLE 18

| Compound | Route | Rodent ICE @ 300 μmol/kg | Primate ICE @ 150 μmol/kg |
|---|---|---|---|
| Deferitrin | po | 1.1 ± 0.8% | 16.8 ± 7.2% |
| Deferitrin | sc | 1.1 ± 0.6% | 15.9 ± 2.7% |
| (S)-4'-HO-DADFT | po | 5.5 ± 1.9% | 25.4 ± 74% |
| (S)-4'-HO-DADFT | sc | 8.7 ± 2.6% | 30.4 ± 7.2% |
| (S)-3'-HO-DADFT | po | 10.6 ± 4.4% | 23.0 ± 4.1% |
| (S)-3'-HO-DADFT | sc | 13.4 ± 4.5% | 21.5 ± 3.2% |

The above protocols and data are taken from Bergeron, R J et al., "Design, Synthesis, and Testing of Non-Nephrotoxic Desazadesferrithiocin Polyether Analogues," *J Med. Chem.* 2008, 51(13), 3913-23. Additional data pertaining to tissue distribution, toxicity, and pharmacokinetics can be found in this publication.

EXAMPLE 20

Salts of DADFT Polyethers as Lanthanide and Actinide Chelating Agents

The protocol employed in Rao L, Choppin G R, and Bergeron R J, *Radiochim. Acta.* 88, 851-856 (2000) could be used, optionally with adaptations clear to those of skill in the art, to ascertain the activity of compounds according to the present invention as chelators of lanthanides and actinides. Salts and polymorphs of Formula I are expected to show efficacy in this assay.

The following compounds can generally be made using the methods known in the art and described above. It is expected that these compounds when made will have activity similar to those that have been made in the examples above.

The notation below is intentionally free of assignment of ionic character; salt are shown as acid compounds paired with bases. In this manner, each structure is intended to represent the corresponding ions that would be formed under a given set of conditions, such as, for example, in aqueous solution.

Typically, a base will ionically bond with the carboxyl group(s) of one or more compounds and release one or more molar equivalents of water. Under certain circumstances, a nitrogen may be a site of acid salt formation. As those of skill in the art will recognize, different ratios of counterions may form stable arrangements and solid forms, including 1:1, 2:1, and 3:1 based on preferred oxidation states of each ion, salt formation conditions (including solvent), etc. All such forms are contemplated here.

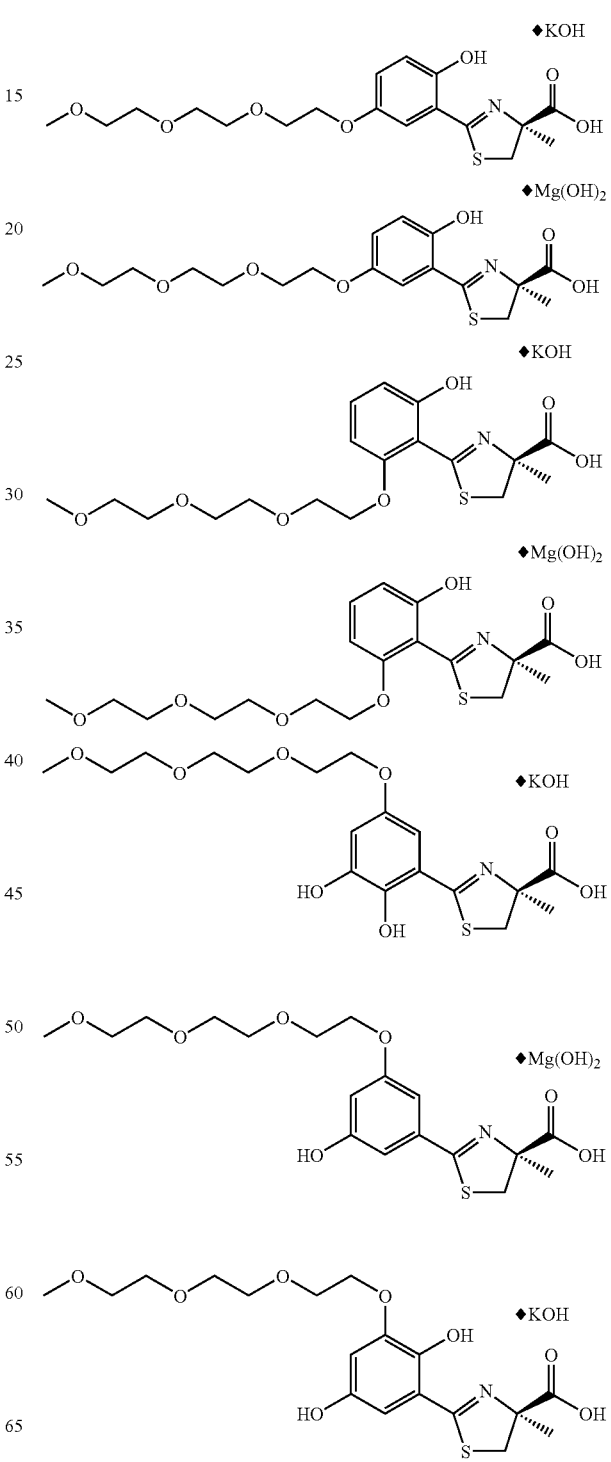

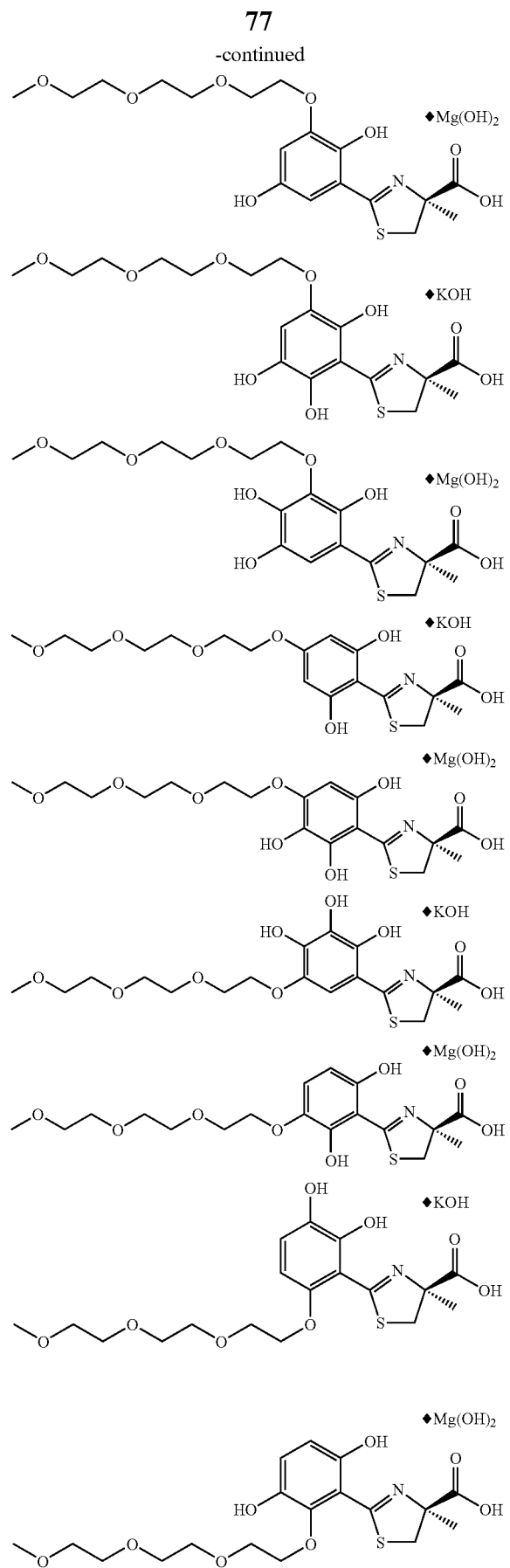
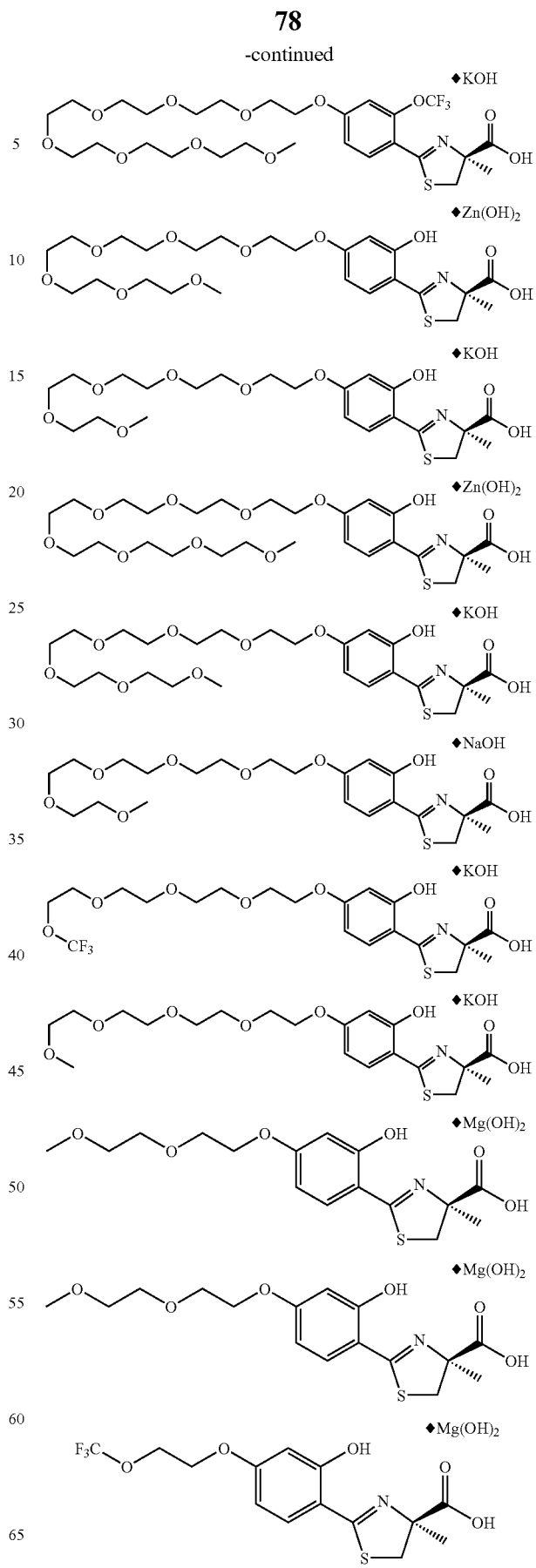

-continued
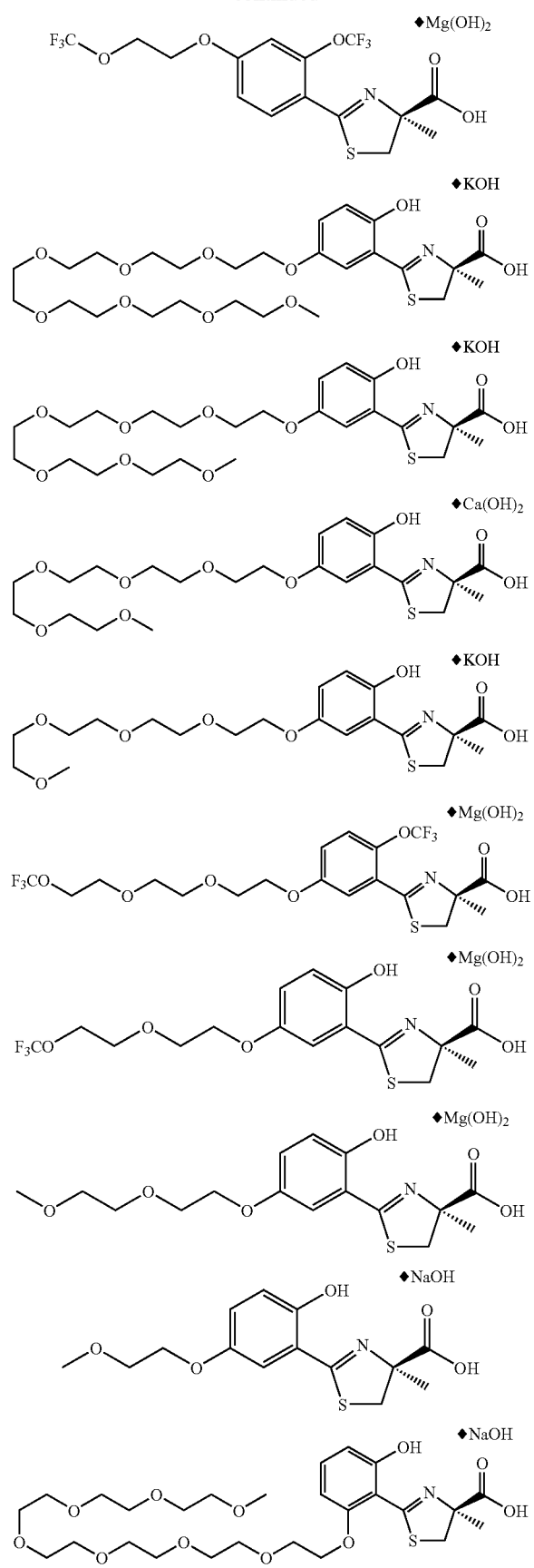
-continued
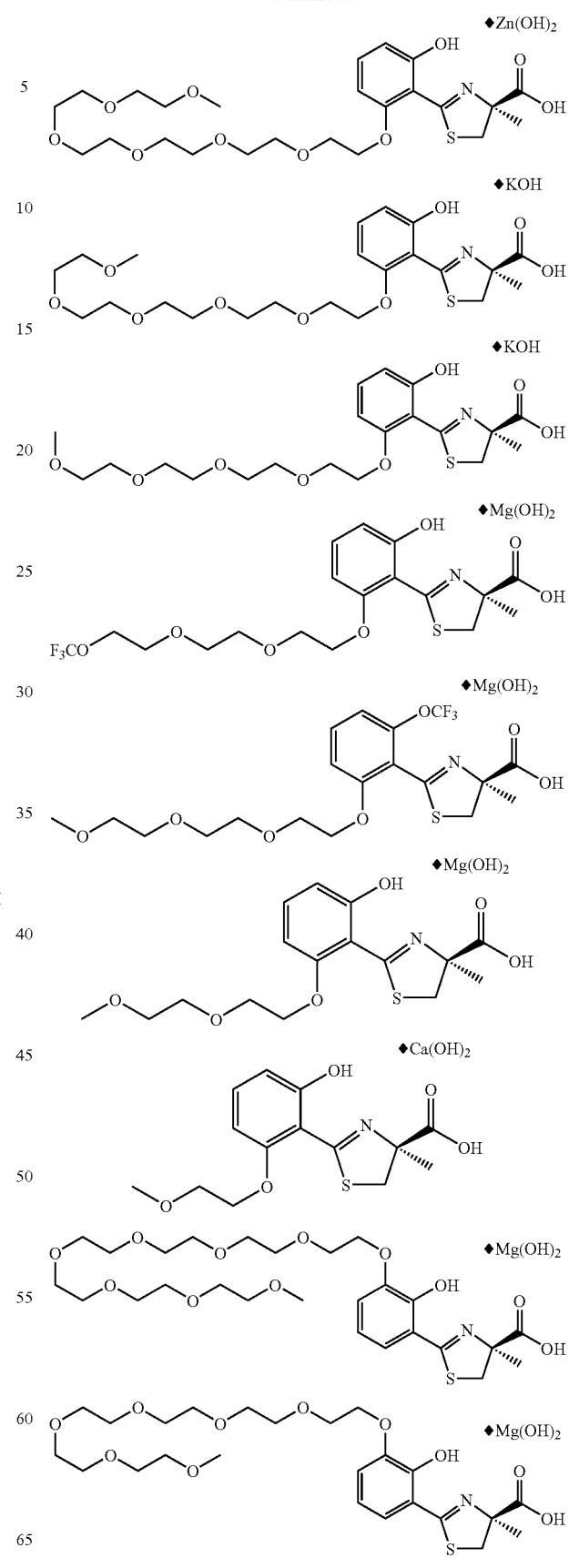

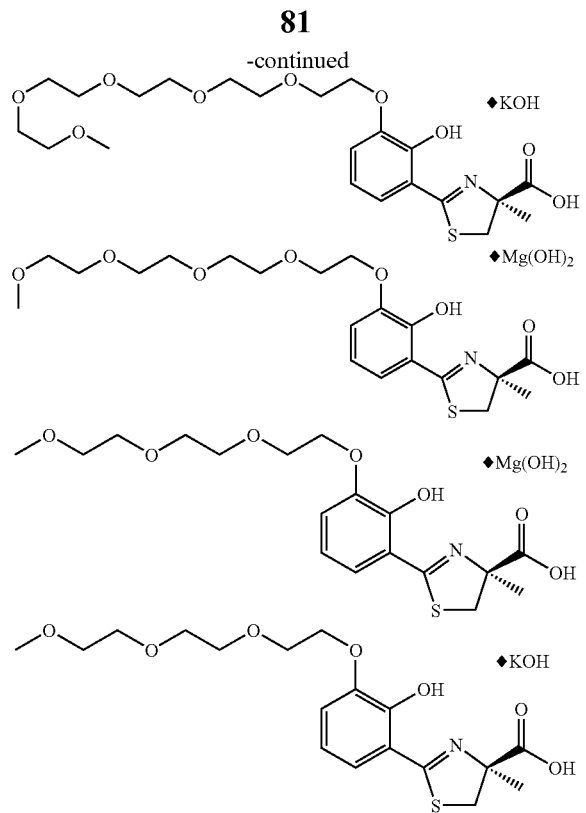

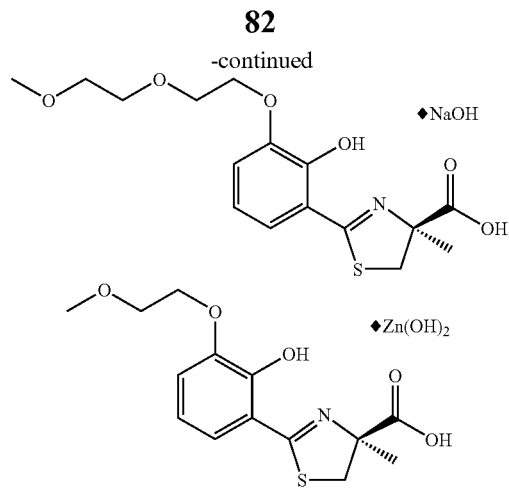

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Magnesium (S)-2-(2-hydroxy-3-(2-(2-(2-methoxyethoxy)ethoxy)ethoxy)phenyl)-4-methyl-4,5-dihydrothiazole-4-carboxylate hydroxide polymorph form A.

* * * * *